(12) United States Patent
Nishikori et al.

(10) Patent No.: US 11,609,495 B2
(45) Date of Patent: Mar. 21, 2023

(54) RADIATION-SENSITIVE RESIN COMPOSITION AND RESIST PATTERN-FORMING METHOD

(71) Applicant: JSR CORPORATION, Tokyo (JP)

(72) Inventors: Katsuaki Nishikori, Tokyo (JP); Kazuya Kiriyama, Tokyo (JP); Takuhiro Taniguchi, Tokyo (JP); Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 239 days.

(21) Appl. No.: 17/081,000

(22) Filed: Oct. 27, 2020

(65) Prior Publication Data

US 2021/0124263 A1 Apr. 29, 2021
US 2021/0389667 A9 Dec. 16, 2021

(30) Foreign Application Priority Data

Oct. 28, 2019 (JP) .............................. JP2019-195559
Oct. 14, 2020 (JP) .............................. JP2020-173561

(51) Int. Cl.
| | | |
|---|---|---|
| G03F 7/004 | (2006.01) | |
| G03F 7/039 | (2006.01) | |
| C08F 220/18 | (2006.01) | |
| C07D 317/70 | (2006.01) | |
| C07C 381/12 | (2006.01) | |
| C07C 309/17 | (2006.01) | |
| C07D 327/04 | (2006.01) | |
| C07C 309/12 | (2006.01) | |
| C07C 65/10 | (2006.01) | |

(Continued)

(52) U.S. Cl.
CPC .......... *G03F 7/0045* (2013.01); *C07C 59/115* (2013.01); *C07C 65/05* (2013.01); *C07C 65/10* (2013.01); *C07C 69/63* (2013.01); *C07C 309/12* (2013.01); *C07C 309/17* (2013.01); *C07C 381/12* (2013.01); *C07D 317/70* (2013.01); *C07D 327/04* (2013.01); *C08F 220/1805* (2020.02); *C08F 220/1806* (2020.02); *C08F 220/1807* (2020.02); *C08F 220/1808* (2020.02); *C08F 220/1809* (2020.02); *C08F 220/1812* (2020.02); *G03F 7/0392* (2013.01); *G03F 7/0397* (2013.01); *C07C 2601/08* (2017.05); *C07C 2603/74* (2017.05)

(58) Field of Classification Search
CPC ................. G03F 7/0392; G03F 7/0397; C08F 220/1807; C08F 220/1806; C08F 220/1805; C08F 220/1809; C08F 220/1812; C08F 220/1808
See application file for complete search history.

(56) References Cited

U.S. PATENT DOCUMENTS 4,910,122 A 3/1990 Arnold et al.
10,120,278 B2 * 11/2018 Fukushima ............... G03F 7/11
(Continued)

FOREIGN PATENT DOCUMENTS

JP 5993448 A 5/1984
JP 0612452 A 1/1994
(Continued)

*Primary Examiner* — Amanda C. Walke
(74) *Attorney, Agent, or Firm* — Element IP, PLC

(57) ABSTRACT

A radiation-sensitive resin composition includes a polymer including a phenolic hydroxyl group, a compound represented by formula (1-1) or formula (1-2), and a compound represented by formula (2). In the formula (1-1), a sum of a, b, and c is no less than 1; at least one of $R^1$, $R^2$, and $R^3$ represents a fluorine atom or the like; and $R^4$ and $R^5$ each independently represent a hydrogen atom, a fluorine atom, or the like. In the formula (1-2), in a case in which d is 1, $R^6$ represents a fluorine atom or the like, and in a case in which d is no less than 2, at least one of the plurality of $R^6$s represents a fluorine atom or the like; and $R^8$ represents a single bond or a divalent organic group having 1 to 20 carbon atoms.

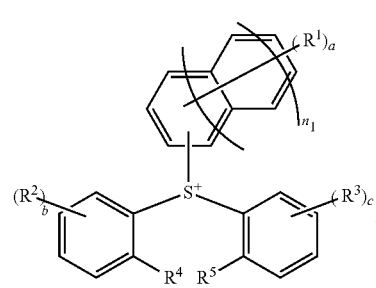

(1-1)

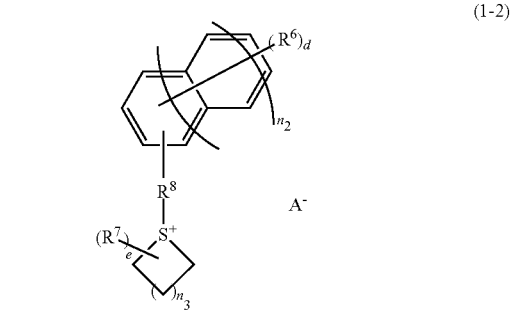

(1-2)

$R^9$—COO⁻ X⁺ (2)

18 Claims, No Drawings

(51) Int. Cl.
   *C07C 59/115*   (2006.01)
   *C07C 69/63*    (2006.01)
   *C07C 65/05*    (2006.01)

(56)            References Cited

U.S. PATENT DOCUMENTS

| | | | |
|---|---|---|---|
| 10,948,822 B2* | 3/2021 | Hatakeyama | C08F 212/20 |
| 11,320,735 B2* | 5/2022 | Nishikori | G03F 7/039 |
| 2017/0008982 A1* | 1/2017 | Hasegawa | C07D 307/00 |
| 2017/0315442 A1* | 11/2017 | Fukushima | C07C 271/24 |
| 2020/0089112 A1* | 3/2020 | Hatakeyama | C07C 309/19 |
| 2020/0393761 A1* | 12/2020 | Nishikori | C09D 125/18 |
| 2021/0318613 A9* | 10/2021 | Nishikori | G03F 7/2004 |

FOREIGN PATENT DOCUMENTS

| | | | |
|---|---|---|---|
| JP | 2010134279 A | 6/2010 | |
| JP | 2014224984 A | 12/2014 | |
| JP | 2016047815 A | 4/2016 | |

* cited by examiner

RADIATION-SENSITIVE RESIN COMPOSITION AND RESIST PATTERN-FORMING METHOD

CROSS-REFERENCE TO RELATED APPLICATIONS

The present application claims priority to Japanese Patent Application No. 2019-195559, filed Oct. 28, 2019, and to Japanese Patent Application No. 2020-173561, filed Oct. 14, 2020. The contents of these applications are incorporated herein by reference in their entirety.

BACKGROUND OF THE INVENTION

Field of the Invention

The present invention relates to a radiation-sensitive resin composition and a resist pattern-forming method.

Description of the Related Art

A radiation-sensitive resin composition for use in microfabrication by lithography generates an acid at a light-exposed region upon an irradiation with a radioactive ray, e.g., an electromagnetic wave such as a far ultraviolet ray such as an ArF excimer laser beam (wavelength of 193 nm), a KrF excimer laser beam (wavelength of 248 nm), etc. or an extreme ultraviolet ray (EUV) (wavelength of 13.5 nm), or a charged particle ray such as an electron beam. A chemical reaction in which the acid serves as a catalyst causes a difference in rates of dissolution in a developer solution between light-exposed regions and light-unexposed regions, whereby a resist pattern is formed on a substrate.

Such a radiation-sensitive resin composition is required not only to have favorable sensitivity to exposure light such as an extreme ultraviolet ray and an electron beam, but also to have superiority with regard to LWR (Line Width Roughness) performance, which indicates line width uniformity, and to resolution.

To meet these requirements, types, molecular structures, and the like of polymers, acid generating agents, and other components which may be used in radiation-sensitive resin compositions have been investigated, and combinations thereof have been further investigated in detail (see Japanese Unexamined Patent Applications, Publication Nos. 2010-134279, 2014-224984, and 2016-047815).

SUMMARY OF THE INVENTION

According to an aspect of the present invention, a radiation-sensitive resin composition includes: a polymer comprising a first structural unit comprising a phenolic hydroxyl group; a compound represented by formula (1-1) or formula (1-2); and a compound represented by formula (2).

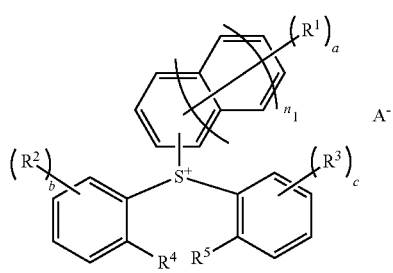

(1-1)

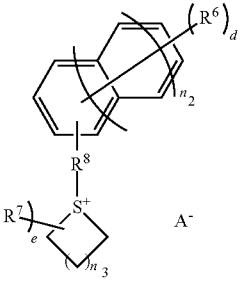

(1-2)

In each of the formula (1-1) and the formula (1-2), $A^-$ represents a monovalent sulfonic acid anion, in the formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^1$, $R^2$, and $R^3$ represents a fluorine atom or a monovalent fluorinated hydrocarbon group having 1 to 10 carbon atoms, in a case in which a is no less than 2, a plurality of $R^4$s are identical or different, in a case in which b is no less than 2, a plurality of $R^2$s are identical or different, and in a case in which c is no less than 2, a plurality of $R^3$s are identical or different; m is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond. In the formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; $n_2$ is 0 or 1; and $n_3$ is an integer of 0 to 3.

$$R^9\text{—COO}^-X^+ \quad (2)$$

In the formula (2), $R^9$ represents a monovalent organic group having 1 to 30 carbon atoms; and $X^+$ represents a monovalent radiation-sensitive onium cation.

According to another aspect of the present invention, a resist pattern-forming method includes: applying a radiation-sensitive resin composition directly or indirectly on a substrate to form a resist film; exposing the resist film; and developing the resist film exposed. The radiation-sensitive resin composition includes: a polymer including a first structural unit including a phenolic hydroxyl group; a compound represented by formula (1-1) or formula (1-2); and a compound represented by formula (2).

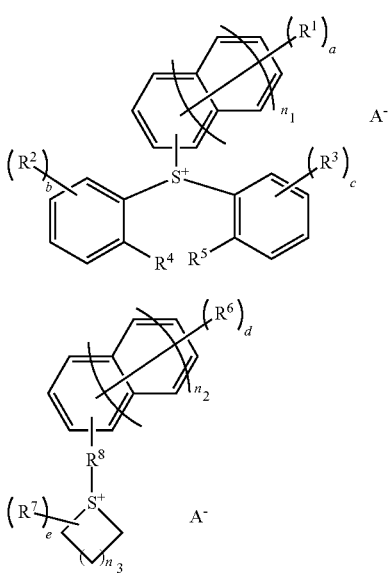

(1-1)

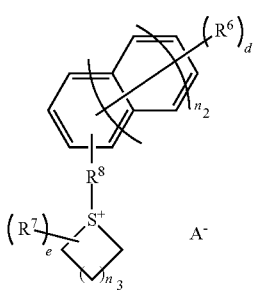

(1-2)

In each of the formula (1-1) and the formula (1-2), A⁻ represents a monovalent sulfonic acid anion, in the formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^1$, $R^2$, and $R^3$ represents a fluorine atom or a monovalent fluorinated hydrocarbon group having 1 to 10 carbon atoms, in a case in which a is no less than 2, a plurality of $R^4$s are identical or different, in a case in which b is no less than 2, a plurality of $R^2$s are identical or different, and in a case in which c is no less than 2, a plurality of $R^3$s are identical or different; m is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond. In the formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; $n_2$ is 0 or 1; and $n_3$ is an integer of 0 to 3.

$$R^9\text{—COO}^-X^+ \qquad (2)$$

In the formula (2), $R^9$ represents a monovalent organic group having 1 to 30 carbon atoms; and $X^+$ represents a monovalent radiation-sensitive onium cation.

DESCRIPTION OF THE EMBODIMENTS

Under current circumstances in which miniaturization of resist patterns has proceeded to a level in which line widths are 40 nm or lower, required levels for the aforementioned types of performance are further elevated.

An embodiment of the invention is a radiation-sensitive resin composition containing:

a polymer (hereinafter, may be also referred to as "(A) polymer" or "polymer (A)") having a first structural unit including a phenolic hydroxyl group;

a compound (hereinafter, may be also referred to as "(B) acid generating agent" or "acid generating agent (B)") represented by the following formula (1-1) or the following formula (1-2); and a compound (hereinafter, may be also referred to as "(C) acid diffusion control agent" or "acid diffusion control agent (C)") represented by the following formula (2),

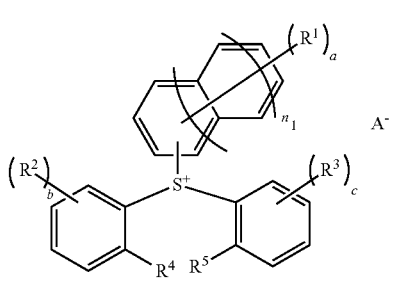

(1-1)

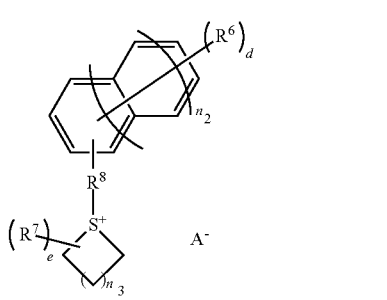

(1-2)

wherein in each of the formula (1-1) and the formula (1-2), A⁻ represents a monovalent sulfonic acid anion, in the formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^1$, $R^2$, and $R^3$ represents a fluorine atom or a monovalent fluorinated hydrocarbon group having 1 to 10 carbon atoms, in a case in which a is no less than 2, a plurality of $R^4$s are identical or different, in a case in which b is no less than 2, a plurality of $R^2$s are identical or different, and in a case in which c is no less than 2, a plurality of $R^3$s are identical or different; m is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond, in the formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; $n_2$ is 0 or 1; and $n_3$ is an integer of 0 to 3, and $$R^9\text{—COO}^-X^+ \qquad (2)$$

in the formula (2), $R^9$ represents a monovalent organic group having 1 to 30 carbon atoms; and $X^+$ represents a monovalent radiation-sensitive onium cation.

According to another embodiment of the invention, a resist pattern-forming method includes: applying the radiation-sensitive resin composition of the embodiment of the invention directly or indirectly on a substrate; exposing a resist film formed by the applying; and developing the resist film exposed.

The radiation-sensitive resin composition and the resist pattern-forming method of the embodiments of the present invention enable a resist pattern to be formed with favorable sensitivity to exposure light, and superiority with regard to each of the LWR performance and the resolution. Therefore, these can be suitably used in working processes of semiconductor devices, in which further progress of miniaturization is expected in the future.

Hereinafter, the radiation-sensitive resin composition and the rest pattern-forming method of embodiments of the present invention will be described in detail.

Radiation-Sensitive Resin Composition

The radiation-sensitive resin composition of one embodiment of the present invention contains the polymer (A), the acid generating agent (B), and the acid diffusion control agent (C). The radiation-sensitive resin composition typically contains an organic solvent (hereinafter, may be also referred to as "(D) organic solvent" or "organic solvent (D)"). The radiation-sensitive resin composition may contain, within a range not leading to impairment of the effects of the present invention, other optional component(s).

Due to the polymer (A), the acid generating agent (B), and the acid diffusion control agent (C) being contained, the radiation-sensitive resin composition enables a resist pattern to be formed with favorable sensitivity to exposure light and superiority with regard to each of the LWR performance and the resolution. Although not necessarily clarified and without wishing to be bound by any theory, the reason for achieving the aforementioned effects by the radiation-sensitive resin composition due to involving such a constitution may be presumed, for example, as in the following. It is believed that due to the acid generating agent (B) being contained in the radiation-sensitive resin composition and having a cation with a specific structure, exposure light is absorbed more easily and acid generating efficiency by exposure improves, and as a result, the radiation-sensitive resin composition enables a resist pattern to be formed with favorable sensitivity to exposure light and superiority with regard to each of the LWR performance and the resolution.

Each component contained in the radiation-sensitive resin composition will be described below.

(A) Polymer

The polymer (A) has the structural unit (hereinafter, may be also referred to as "structural unit (I)" or "first structural unit") including the phenolic hydroxyl group.

The polymer (A) preferably further has a structural unit (hereinafter, may be also referred to as "structural unit (II)" or "second structural unit") including an acid-labile group which is dissociated by an action of an acid to give a carboxy group. The polymer (A) preferably further has a structural unit (hereinafter, may be also referred to as "structural unit (III)" or "third structural unit") which includes a partial structure represented by the following formula (5), described below. The polymer (A) may further have other structural unit(s) (hereinafter, may be also referred to as simply "other structural unit(s)") aside from the structural units (I) to (III). The radiation-sensitive resin composition may contain one, or two or more types of the polymer (A).

Each structural unit contained in the polymer (A) will be described below.

Structural Unit (I)

The structural unit (I) includes a phenolic hydroxyl group. The "phenolic hydroxyl group" as referred to herein is not limited to a hydroxy group directly bonding to a benzene ring, and means any hydroxy group directly bonding to an aromatic ring in general.

In the case of exposure to KrF, exposure to EUV, or exposure to an electron beam, the sensitivity of the radiation-sensitive resin composition to exposure light can be further improved due to the polymer (A) having the structural unit (I). Accordingly, the radiation-sensitive resin composition can be suitably used as a radiation-sensitive resin composition intended for exposure to KrF, exposure to EUV, or exposure to an electron beam.

Examples of the structural unit (I) include structural units (hereinafter, may be also referred to as "structural units (I-1) to (I-14)") represented by the following formulae (I-1) to (I-14), and the like.

(I-1)

(I-2)

(I-3)

(I-4) 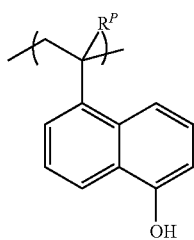

(I-5) 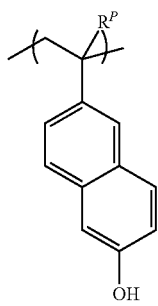

(I-6) 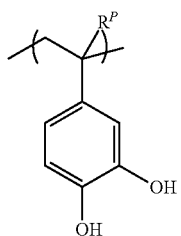

(I-7) 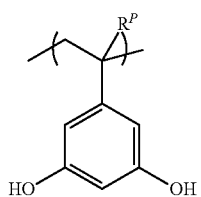

(I-8) 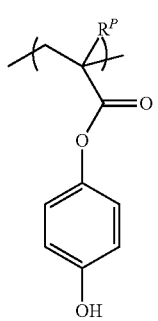

(I-9) 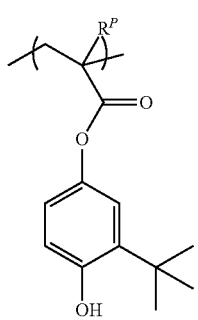

(I-10) 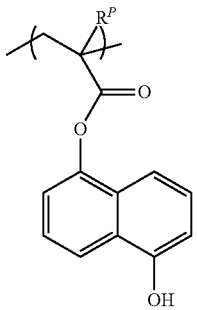

(I-11) 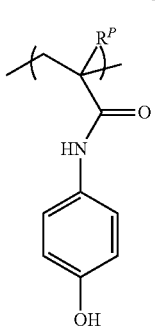

(I-12) 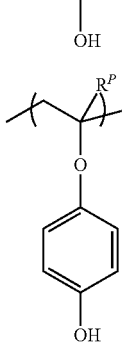

(I-13) 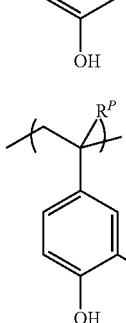

(I-14) 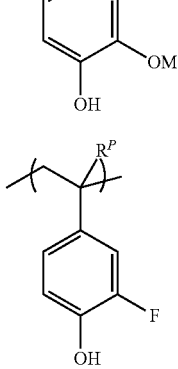

In each of the above formulae (I-1) to (I-14), $R^P$ represents a hydrogen atom, a fluorine atom, a methyl group, or a trifluoromethyl group.

In light of a degree of copolymerization of a monomer that gives the structural unit (I), $R^P$ represents preferably a hydrogen atom or a methyl group, and more preferably a hydrogen atom.

The structural unit (I) is preferably the structural unit (I-1), the structural unit (I-2), or a combination thereof.

In the polymer (A), the lower limit of a proportion of the structural unit (I) contained with respect to total structural units constituting the polymer (A) is preferably 10 mol %, more preferably 20 mol %, and still more preferably 25 mol %. The upper limit of the proportion is preferably 80 mol %, more preferably 60 mol %, and still more preferably 50 mol %. When the proportion of the structural unit (I) falls within the above range, the sensitivity to exposure light, the LWR performance, and the resolution of the radiation-sensitive resin composition can be further improved.

Structural Unit (II)

The structural unit (II) includes an acid-labile group (hereinafter, may be also referred to as "acid-labile group (α)") which is dissociated by an action of an acid to give a carboxy group. The acid-labile group (α) is a group that substitutes for a hydrogen atom of a carboxy group, and is dissociated by an action of an acid to give a carboxy group. The acid-labile group (α) is dissociated by an action of an acid generated from the acid generating agent (B) upon exposure, creating a difference in solubility in a developer solution of the polymer (A) between a light-exposed region and a light-unexposed region; accordingly, a resist pattern can be formed.

Examples of the structural unit (II) include structural units (hereinafter, may be also referred to as "structural units (II-1) to (II-3)") represented by the following formulae (4-1) to (4-3), and the like. It is to be noted that in the following formula (4-1), —C($R^X$)($R^Y$)($R^Z$) bonding to an oxy-oxygen atom derived from the carboxy group corresponds to the acid-labile group (a).

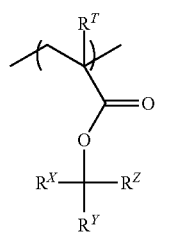

(4-1)

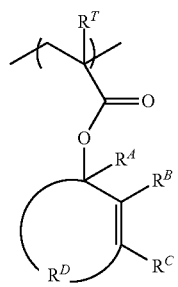

(4-2)

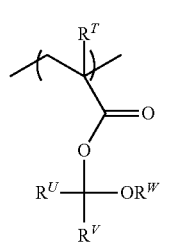

(4-3)

In each of the above formulae (4-1), (4-2), and (4-3), each $R^X$ independently represents a hydrogen atom, a fluorine atom, a methyl group, or a trifluoromethyl group.

In the above formula (4-1), each $R^X$ independently represents a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent an alicyclic structure having 3 to 20 ring atoms, together with the carbon atom to which $R^Y$ and $R^Z$ bond.

In the above formula (4-2), $R^A$ represents a hydrogen atom; $R^B$ and $R^C$ each independently represent a hydrogen atom or a monovalent hydrocarbon group having 1 to 20 carbon atoms; and $R^D$ represents a divalent hydrocarbon group having 1 to 20 carbon atoms constituting an unsaturated alicyclic structure having 4 to 20 ring atoms together with the carbon atom to which each of $R^A$, $R^B$, and $R^C$ bonds.

In the above formula (4-3), $R^U$ and $R^V$ each independently represent a hydrogen atom or a monovalent hydrocarbon group having 1 to 20 carbon atoms, and each $R^W$ independently represents a monovalent hydrocarbon group having 1 to 20 carbon atoms, or $R^U$ and $R^V$ taken together represent an alicyclic structure having 3 to 20 ring atoms, together with the carbon atom to which $R^U$ and $R^V$ bond, or $R^U$ and $R^W$ taken together represent an aliphatic heterocyclic structure having 5 to 20 ring atoms, together with the carbon atom to which $R^U$ bonds and the oxygen atom to which $R^W$ bonds.

The "hydrocarbon group" as referred to herein may be exemplified by a chain hydrocarbon group, an alicyclic hydrocarbon group, and an aromatic hydrocarbon group. The "hydrocarbon group" may be either a saturated hydrocarbon group or an unsaturated hydrocarbon group. The "chain hydrocarbon group" as referred to herein means a hydrocarbon group not including a cyclic structure but being constituted with only a chain structure, and may be exemplified by a linear hydrocarbon group and a branched hydrocarbon group. The "alicyclic hydrocarbon group" as referred to herein means a hydrocarbon group that includes, as a ring structure, not an aromatic ring structure but an alicyclic structure alone, and may be exemplified by a monocyclic alicyclic hydrocarbon group and a polycyclic alicyclic hydrocarbon group. With regard to this point, it is not necessary for the alicyclic hydrocarbon group to be constituted with only an alicyclic structure; it may include a chain structure in a part thereof. The "aromatic hydrocarbon group" as referred to herein means a hydrocarbon group that includes an aromatic ring structure as a ring structure. With regard to this point, it is not necessary for the aromatic hydrocarbon group to be constituted with only an aromatic ring structure; it may include a chain structure or an alicyclic structure in a part thereof.

The monovalent hydrocarbon group having 1 to 20 carbon atoms which may be represented by $R^X$, $R^Y$, $R^Z$, $R^B$, $R^C$, $R^U$, $R^V$, or $R^W$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, an n-propyl group, an i-propyl group, an n-butyl group, a sec-butyl group, an iso-butyl group, and a tert-butyl group;

alkenyl groups such as an ethenyl group, a propenyl group, and a butenyl group;

alkynyl groups such as an ethynyl group, a propynyl group, and a butynyl group; and the like.

Examples of the monovalent alicyclic hydrocarbon group having 3 to 20 carbon atoms include:

alicyclic saturated hydrocarbon groups such as a cyclopentyl group, a cyclohexyl group, a norbornyl group, an adamantyl group, a tricyclodecyl group, and a tetracyclodecyl group;

alicyclic unsaturated hydrocarbon groups such as a cyclopentenyl group, a cyclohexenyl group, a norbornenyl group, a tricyclodecenyl group, and a tetracyclodecenyl group; and the like.

Examples of the monovalent aromatic hydrocarbon group having 6 to 20 carbon atoms include:

aryl groups such as a phenyl group, a tolyl group, a xylyl group, a naphthyl group, and an anthryl group;

aralkyl groups such as a benzyl group, a phenethyl group, a naphthylmethyl group, and an anthrylmethyl group; and the like.

Examples of the alicyclic structure having 3 to 20 ring atoms which may be represented by $R^Y$ and $R^Z$ taken together, together with the carbon atom to which $R^Y$ and $R^Z$ bond include:

monocyclic saturated alicyclic structures such as a cyclopropane structure, a cyclobutane structure, a cyclopentane structure, and a cyclohexane structure; polycyclic saturated alicyclic structures such as a norbornane structure and an adamantane structure;

monocyclic unsaturated alicyclic structures such as a cyclopropene structure, a cyclobutene structure, a cyclopentene structure, and a cyclohexene structure; polycyclic unsaturated alicyclic structures such as a nobornene structure; and the like.

Examples of the divalent hydrocarbon group having 1 to 20 carbon atoms which is represented by $R^D$ include groups obtained by removing one hydrogen atom from the groups exemplified as the monovalent hydrocarbon group having 1 to 20 carbon atoms which may be represented by $R^X$, $R^Y$, $R^Z$, $R^B$, $R^C$, $R^U$, $R^V$, or $R^W$; and the like.

Examples of the unsaturated alicyclic structure having 4 to 20 ring atoms which is represented by $R^D$, together with the carbon atom to which each of $R^A$, $R^B$, and $R^C$ bonds include:

monocyclic unsaturated alicyclic structures such as a cyclobutene structure, a cyclopentene structure, and a cyclohexene structure;

polycyclic unsaturated alicyclic structures such as a nobornene structure; and the like.

Examples of the alicyclic structure having 3 to 20 ring atoms which may be represented by $R^U$ and $R^V$ taken together, together with the carbon atom to which $R^U$ and $R^V$ bond, include structures similar to the structures exemplified as the alicyclic structure having 3 to 20 ring atoms which may be represented by $R^Y$ and $R^Z$ taken together, together with the carbon atom to which $R^Y$ and $R^Z$ bond; and the like.

Examples of the aliphatic heterocyclic structure having 5 to 20 ring atoms which may be represented by $R^U$ and $R^W$ taken together, together with the carbon atom to which $R^U$ bonds and the oxygen atom to which $R^W$ bonds, include:

saturated oxygen-containing heterocyclic structures such as an oxacyclobutane structure, an oxacyclopentane structure, and an oxacyclohexane structure; unsaturated oxygen-containing heterocyclic structures such as an oxacyclobutene structure, an oxacyclopentene structure, and an oxacyclohexene structure; and the like.

In light of a degree of copolymerization of a monomer that gives the structural unit (I), $R^X$ represents preferably a hydrogen atom or a methyl group.

$R^X$ represents preferably the chain hydrocarbon group or the aromatic hydrocarbon group, more preferably the alkyl group or the aryl group, and still more preferably a methyl group, an ethyl group, an i-propyl group, a tert-butyl group, or a phenyl group.

$R^Y$ and $R^Z$ taken together preferably represent the alicyclic structure having 3 to 20 ring atoms, together with the carbon atom to which $R^Y$ and $R^Z$ bond. The alicyclic structure is preferably the saturated alicyclic structure, more preferably the monocyclic saturated alicyclic structure, and still more preferably a cyclopentane structure or a cyclohexane structure. In the case in which $R^Y$ and $R^Z$ taken together represent the alicyclic structure having 3 to 20 ring atoms, together with the carbon atom to which $R^Y$ and $R^Z$ bond, $R^X$ represents preferably the alkyl group, an ethenyl group, or a phenyl group. In particular, in a case in which the alicyclic structure includes a norbornane skeleton, $R^X$ represents preferably the alkyl group, and more preferably an ethyl group.

Examples of the alicyclic structure having 3 to 20 ring atoms and including a norbornane skeleton which may be represented in the above formula (4-1) by $R^Y$ and $R^Z$ taken together, together with the carbon atom to which $R^Y$ and $R^Z$ bond include structures represented by the following formulae. In each of the following formulae, $R^X$ is as defined above, and * represents an atomic bond.

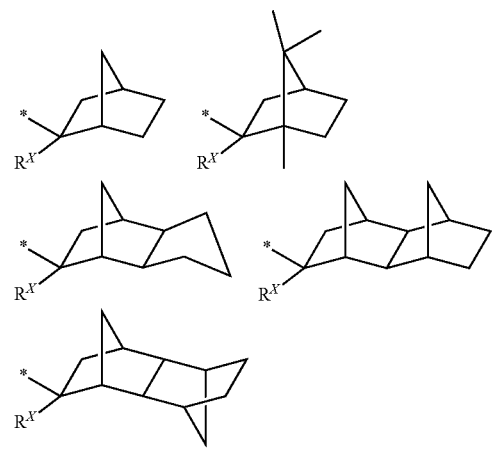

$R^B$ represents preferably a hydrogen atom.

$R^C$ represents preferably a hydrogen atom or the chain hydrocarbon group, more preferably a hydrogen atom or the alkyl group, and still more preferably a hydrogen atom or a methyl group.

The unsaturated alicyclic structure having 4 to 20 ring atoms represented by $R^D$, together with the carbon atom to which each of $R^A$, $R^B$, and $R^C$ bonds is preferably a monocyclic unsaturated alicyclic structure, and more preferably a cyclopentane structure or a cyclohexene structure.

The structural unit (II) is preferably the structural unit (II-1) or the structural unit (II-2).

The structural unit (II-1) is preferably exemplified by structural units (hereinafter, may be also referred to as "structural units (II-1-1) to (II-1-5)") represented by the following formulae (II-1-1) to (II-1-5).

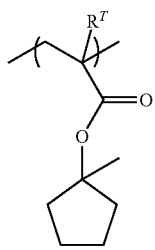
(II-1-1)

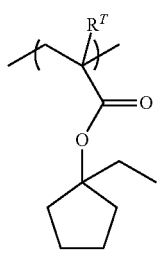
(II-1-2)

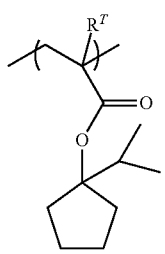
(II-1-3)

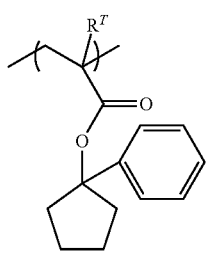
(II-1-4)

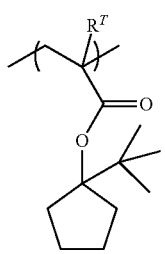
(II-1-5)

In the above formulae (II-1-1) to (II-1-5), $R^T$ is as defined in the above formula (4-1).

The structural unit (II-2) is preferably exemplified by structural units (hereinafter, may be also referred to as "structural units (II-2-1) and (II-2-2)") represented by the following formulae (II-2-1) to (II-2-2).

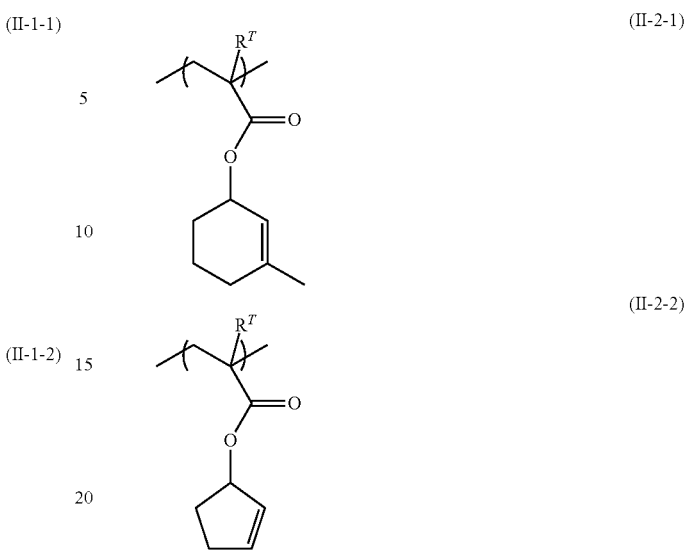

In the above formulae (II-2-1) and (II-2-2), $R^T$ is as defined in the above formula (4-2).

In the structural unit (II), the acid-labile group (α) is preferably at least five atoms away, in terms of a number of atoms, from a main chain of the polymer. "Main chain of the polymer" as referred to herein means the longest atomic chain among atomic chains constituting the polymer. A structural unit including a partial structure represented by —CO—O—J—CO—O— between the main chain of the polymer and the acid-labile group (α) is preferred as the case in which the acid-labile group (α) is at least five atoms away, in terms of the number of atoms, from the main chain of the polymer. Herein, J represents a divalent organic group having 1 to 20 carbon atoms, wherein a carbon atom of the carbonyl group bonds to the main chain of the polymer, and the ethereal oxygen atom bonds to the acid-labile group (α). Examples of the divalent organic group having 1 to 20 carbon atoms include groups similar to those exemplified as the divalent organic group having 1 to 20 carbon atoms which may be represented by $R^8$. In a case in which J in the partial structure represents, for example, a methylene group, the acid-labile group (α) is five atoms away, in terms of the number of atoms, from the main chain of the polymer. J represents preferably an alkanediyl group having 1 to 10 carbon atoms, more preferably an alkanediyl group having 1 to 6 carbon atoms, still more preferably an alkanediyl group having 1 to 3 carbon atoms, and particularly preferably a methylene group or a 1,2-ethanediyl group.

In the case in which the polymer (A) has the structural unit (II), the lower limit of a proportion of the structural unit (II) in the polymer (A) with respect to total structural units constituting the polymer (A) is preferably 30 mol %, more preferably 40 mol %, and still more preferably 50 mol %. The upper limit of the proportion is preferably 90 mol %, more preferably 80 mol %, and still more preferably 70 mol %. When the proportion of the structural unit (II) falls within the above range, the sensitivity to exposure light, the LWR performance, and the resolution of the radiation-sensitive resin composition can be further improved.

Structural Unit (III)

The structural unit (III) is a structural unit including a group represented by the following formula (5). When the polymer (A) further has the structural unit (III), the sensitivity to exposure light, the LWR performance, and the resolution of the radiation-sensitive resin composition can be further improved.

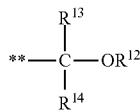

(5)

In the above formula (5), $R^{12}$ represents a hydrogen atom or a monovalent organic group having 1 to 20 carbon atoms; $R^{13}$ and $R^{14}$ each independently represent a fluorine atom or a monovalent fluorinated hydrocarbon group having 1 to 10 carbon atoms; and ** denotes a binding site to a part other than the group represented by the above formula (5) in the third structural unit.

The "organic group" as referred to herein means a group having at least one carbon atom.

The monovalent organic group having 1 to 20 carbon atoms which may be represented by $R^{12}$ is exemplified by: a monovalent hydrocarbon group having 1 to 20 carbon atoms; a group (hereinafter, may be also referred to as "group (α)") that includes a divalent hetero atom-containing group between two adjacent carbon atoms of the hydrocarbon group having 1 to 20 carbon atoms; a group (hereinafter, may be also referred to as "group (β)") obtained by substituting with a monovalent hetero atom-containing group, a part or all of hydrogen atoms included in the hydrocarbon group having 1 to 20 carbon atoms; a group (hereinafter, may be also referred to as "group (γ)") obtained by substituting with a monovalent hetero atom-containing group, a part or all of hydrogen atoms included in the group (α); and the like.

The monovalent fluorinated hydrocarbon group having 1 to 10 carbon atoms which may be represented by $R^{13}$ or $R^{14}$ is exemplified by a group obtained by substituting with a fluorine atom at least one hydrogen atom included in the monovalent hydrocarbon group having 1 to 10 carbon atoms, and the like. Specific examples include partially fluorinated alkyl groups such as a fluoromethyl group, a difluoromethyl group, a difluoroethyl group, a trifluoroethyl group, and a trifluoropropyl group; perfluoroalkyl groups such as a trifluoromethyl group, a pentafluoroethyl group, and a hexafluoropropyl group; and the like.

$R^{12}$ represents preferably a hydrogen atom.

$R^{13}$ and $R^{14}$ each represent preferably the monovalent fluorinated hydrocarbon group having 1 to 10 carbon atoms, more preferably a monovalent perfluoroalkyl group having 1 to carbon atoms, and still more preferably a trifluoromethyl group.

The group represented by the above formula (5) is preferably a hydroxybis(perfluoroalkyl)methyl group, and more preferably a hydroxybis(trifluoromethyl)methyl group.

Examples of the structural unit (III) include structural units (hereinafter, may be also referred to as "structural units (III-1) and (III-2)") represented by the following formulae (III-1) and (III-2), and the like.

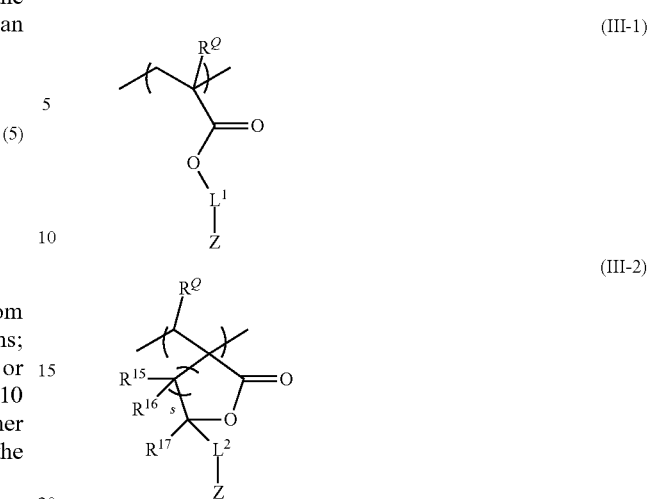

In the above formulae (III-1) and (III-2), $R^Q$ represents a hydrogen atom, a fluorine atom, a methyl group, or a trifluoromethyl group; and Z represents the group represented by the above formula (5).

In the above formula (III-1), $L^1$ represents a single bond or a divalent organic group having 1 to 20 carbon atoms.

In the above formula (III-2), $L^2$ represents a single bond or a divalent organic group having 1 to 20 carbon atoms; $R^{15}$, $R^{16}$, and $R^{17}$ each independently represent a hydrogen atom or a monovalent organic group having 1 to 20 carbon atoms; and s is an integer of 1 to 4, wherein in a case in which s is no less than 2, a plurality of $R^{15}$s are identical or different, a plurality of $R^{16}$s are identical or different, and a plurality of $R^{17}$s are identical or different.

Examples of the divalent organic group having 1 to 20 carbon atoms which may be represented by $L^1$ or $L^2$ include groups obtained by removing one hydrogen atom from the groups exemplified as the monovalent organic group having 1 to 20 carbon atoms which may be represented by $R^{12}$ in the above formula (5).

Examples of the monovalent organic group having 1 to 20 carbon atoms which may be represented by $R^{15}$, $R^{16}$, or $R^{17}$ include groups similar to those exemplified as the monovalent organic group having 1 to 20 carbon atoms which may be represented by $R^{12}$ in the above formula (5), and the like.

$R^Q$ in the above formula (III-1) represents preferably a hydrogen atom or a methyl group, and more preferably a methyl group.

$R^Q$ in the above formula (III-2) represents preferably a hydrogen atom.

$L^1$ represents preferably the divalent hydrocarbon group having 1 to 20 carbon atoms, and more preferably a divalent alicyclic hydrocarbon group having 3 to 20 carbon atoms.

$L^2$ represents preferably the divalent hydrocarbon group having 1 to 20 carbon atoms, and more preferably a divalent chain hydrocarbon group having 1 to 20 carbon atoms.

$R^{15}$ and $R^{16}$ each represent preferably a hydrogen atom.

$R^{17}$ represents preferably the monovalent hydrocarbon group having 1 to 20 carbon atoms, and more preferably a monovalent aromatic hydrocarbon group having 6 to 20 carbon atoms.

s is preferably 1.

The structural unit (III-1) is preferably a structural unit (hereinafter, may be also referred to as "structural unit (III-1-1)") represented by the following formula (III-1-1), and the structural unit (III-2) is preferably a structural unit (hereinafter, may be also referred to as "structural unit (III-2-1)") represented by the following formula (III-2-1).

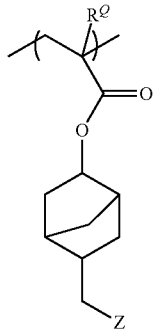

(III-1-1)

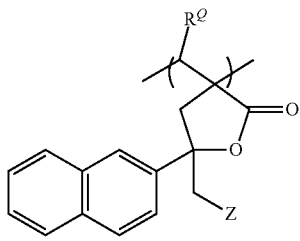

(III-2-1)

In each of the above formulae (III-1-1) and (III-2-1), $R^Q$ and Z are each as defined in the above formulae (III-1) and (III-2).

In the case in which the polymer (A) has the structural unit (III), the lower limit of a proportion of the structural unit (III) in the polymer (A) with respect to total structural units constituting the polymer (A) is preferably 1 mol %, and more preferably 5 mol %. The upper limit of the proportion is preferably 30 mol %, and more preferably 20 mol %. When the proportion of the structural unit (III) falls within the above range, the sensitivity to exposure light, the LWR performance, and the resolution of the radiation-sensitive resin composition can be even further improved.

Structural Unit (IV)

The structural unit (IV) is a structural unit including a partial structure which generates a sulfonic acid upon irradiation. When the polymer (A) further has the structural unit (IV), the sensitivity to exposure light, the LWR performance, and the resolution of the radiation-sensitive resin composition can be further improved. Examples of a monomer which gives such a structural unit include monomers represented by the following formulae. It is to be noted that $R^A$ in each of the following formulae represents a hydrogen atom or a methyl group.

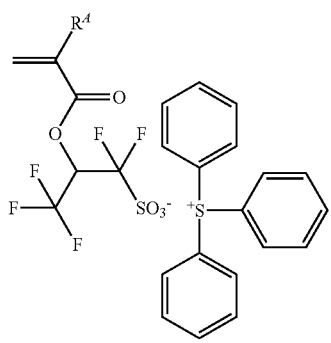

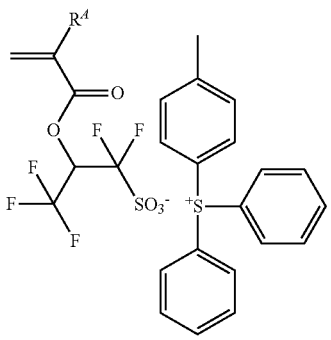

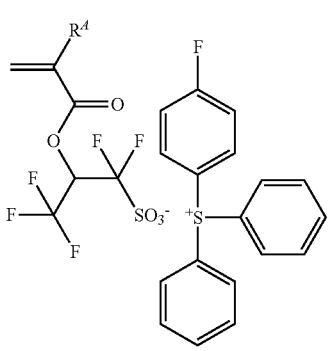

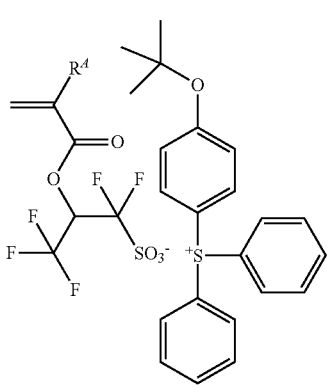

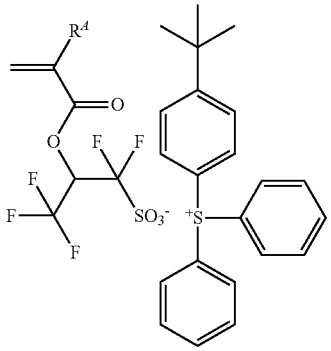

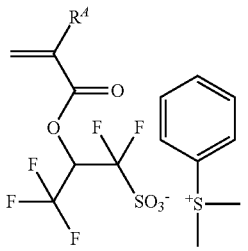

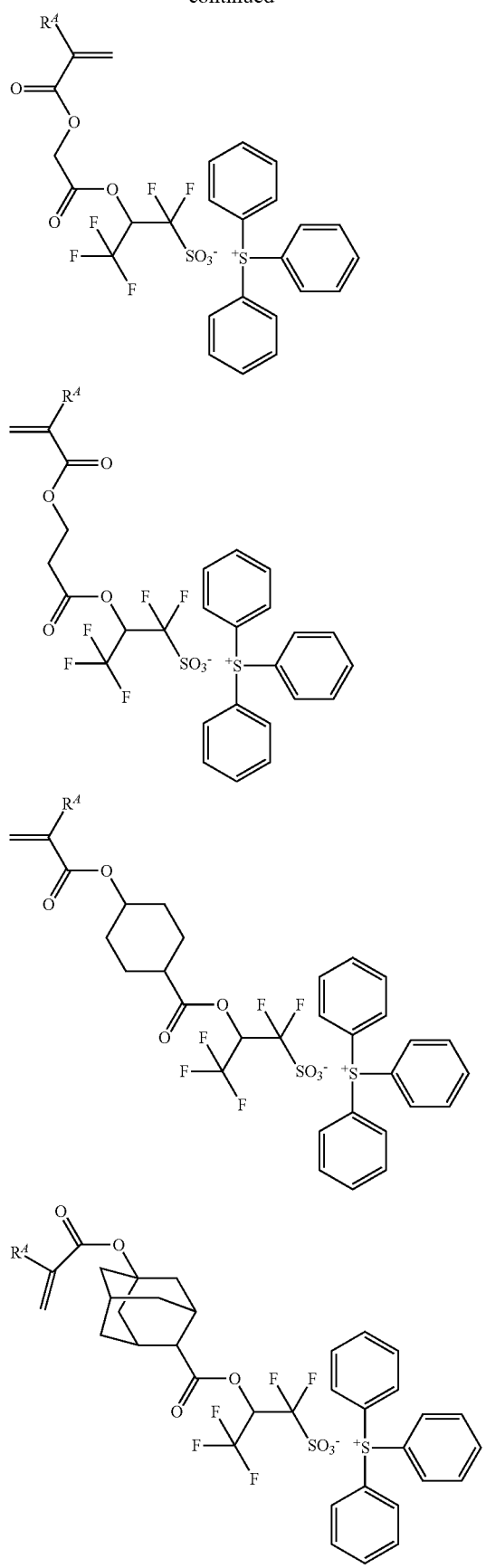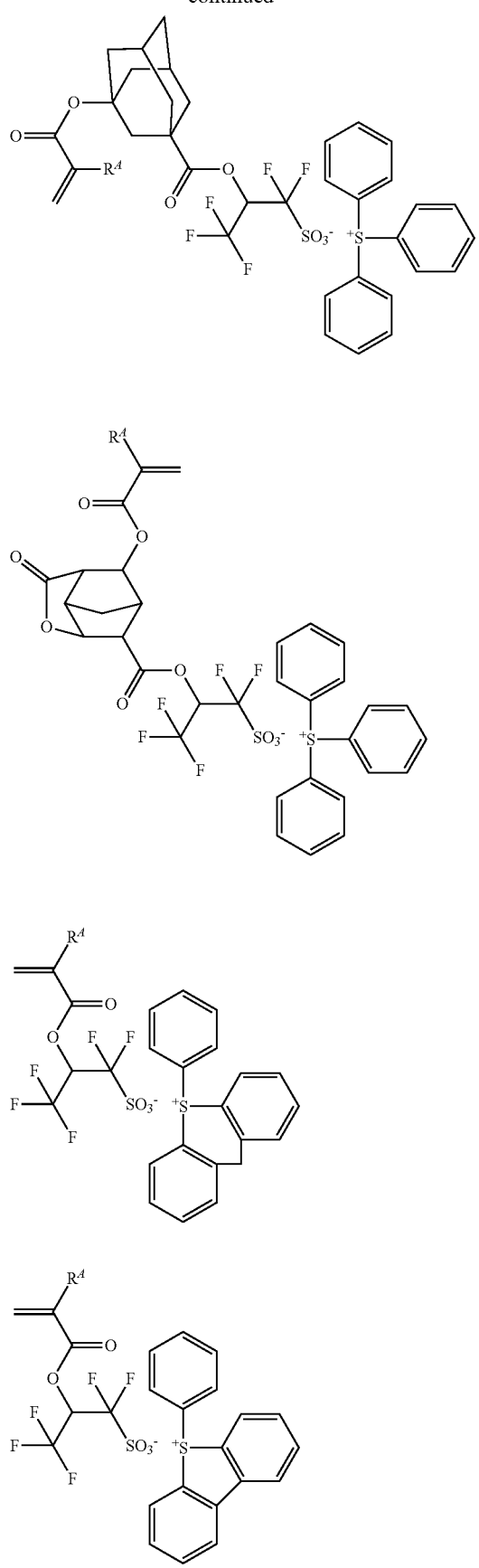

-continued
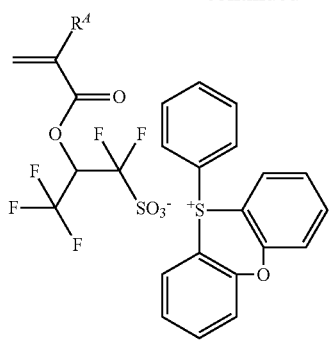
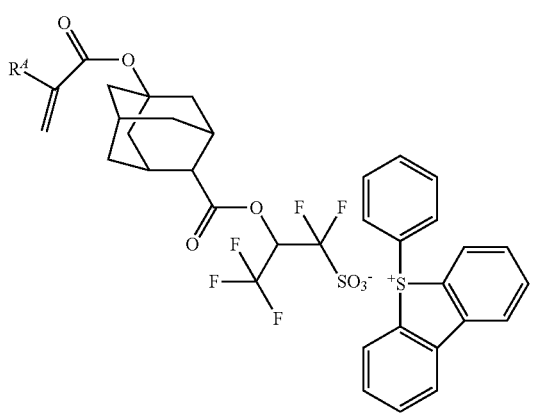
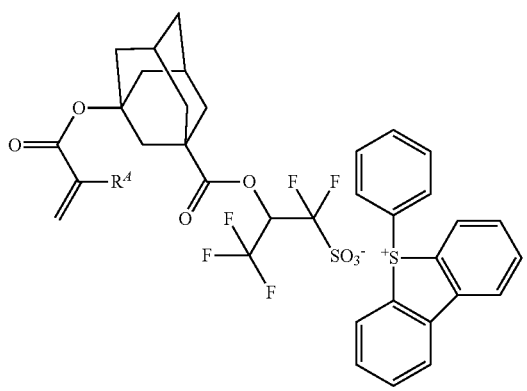
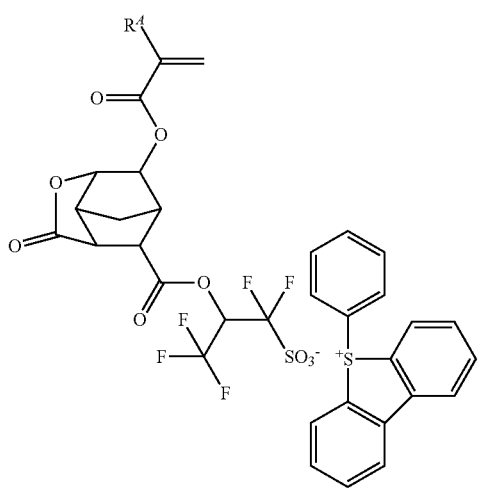
-continued
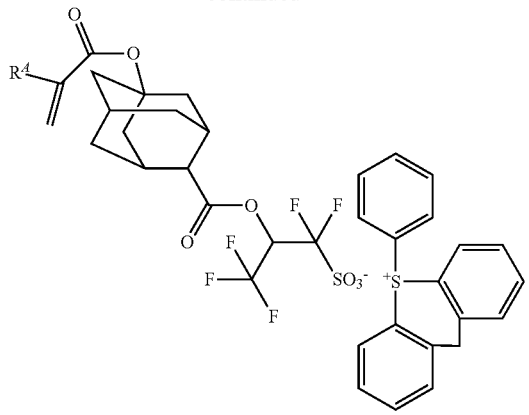
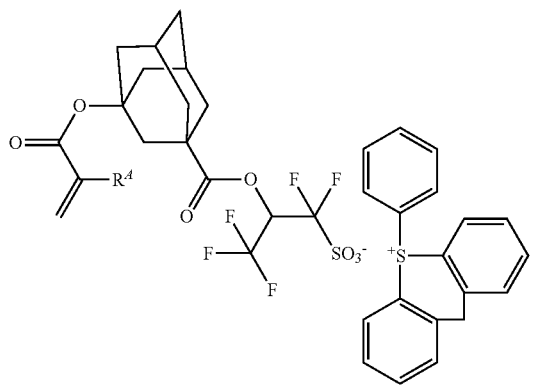
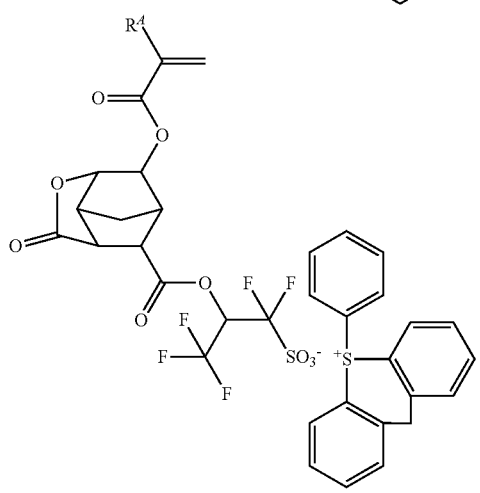
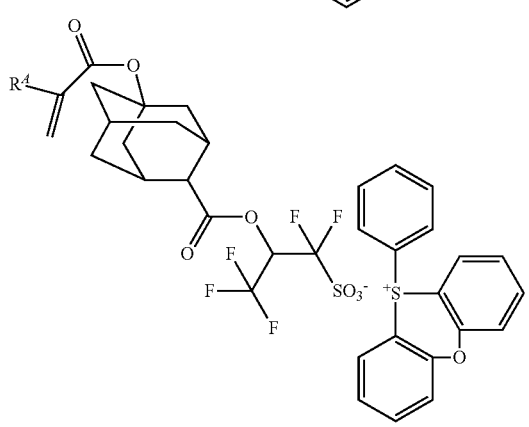

-continued
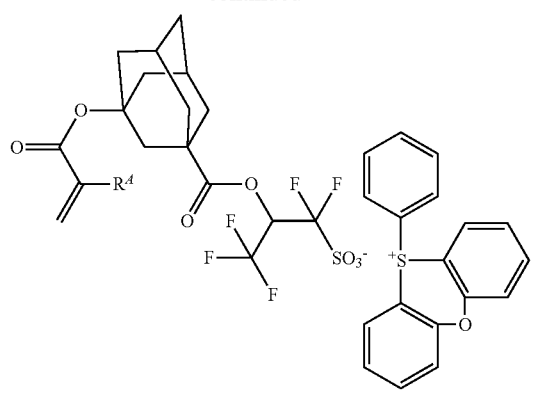
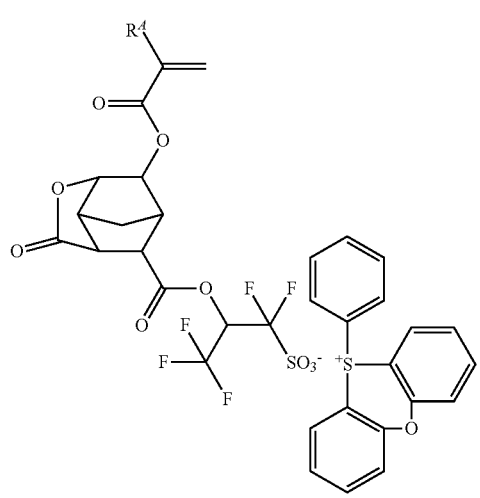
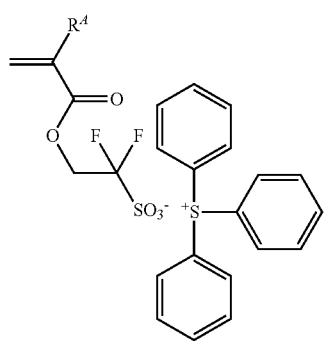
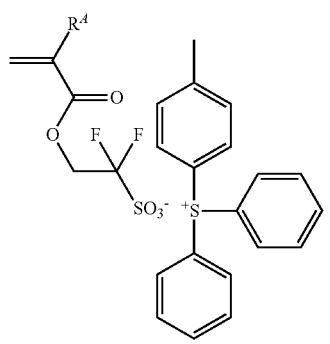
-continued
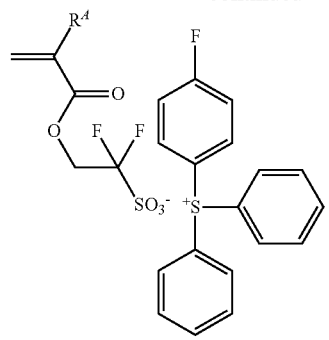
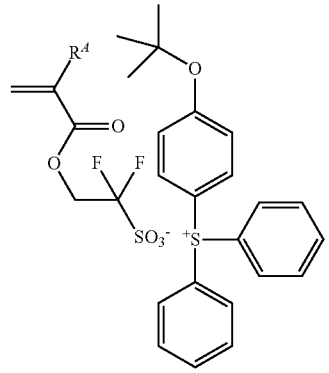
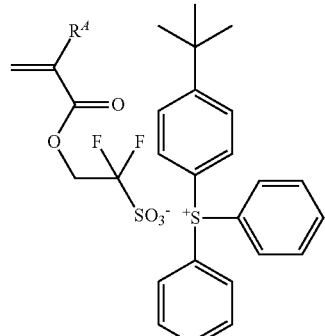
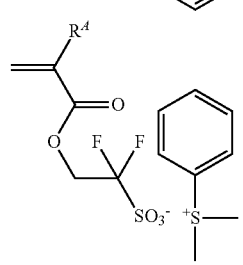
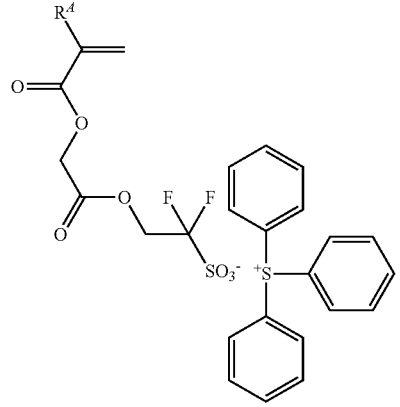

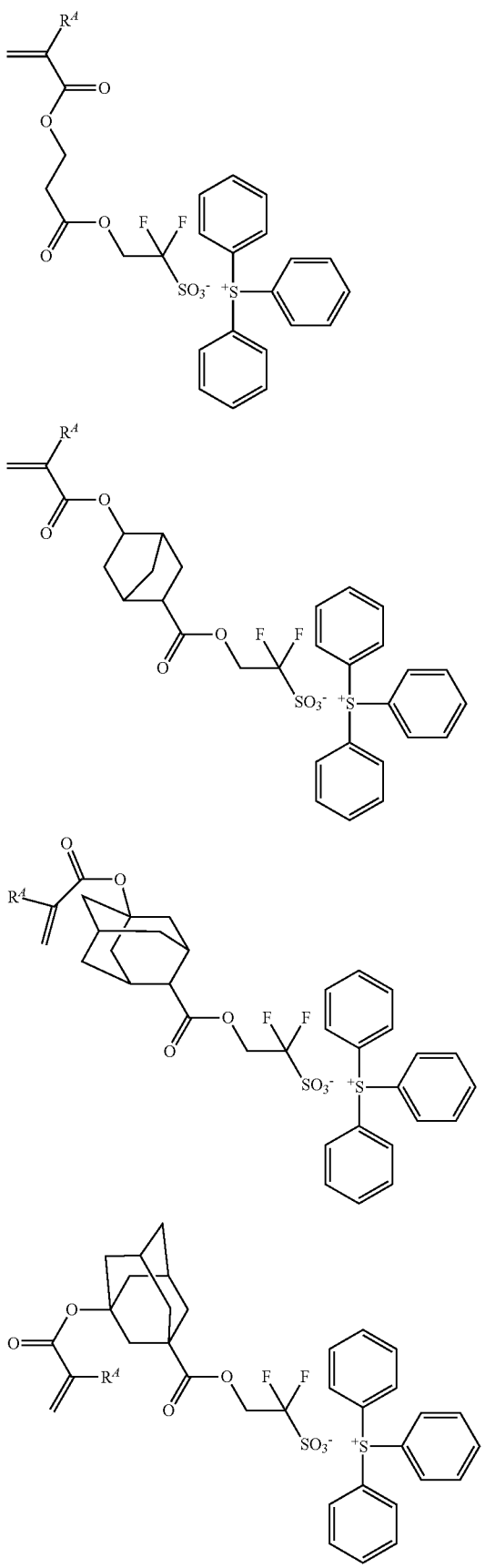
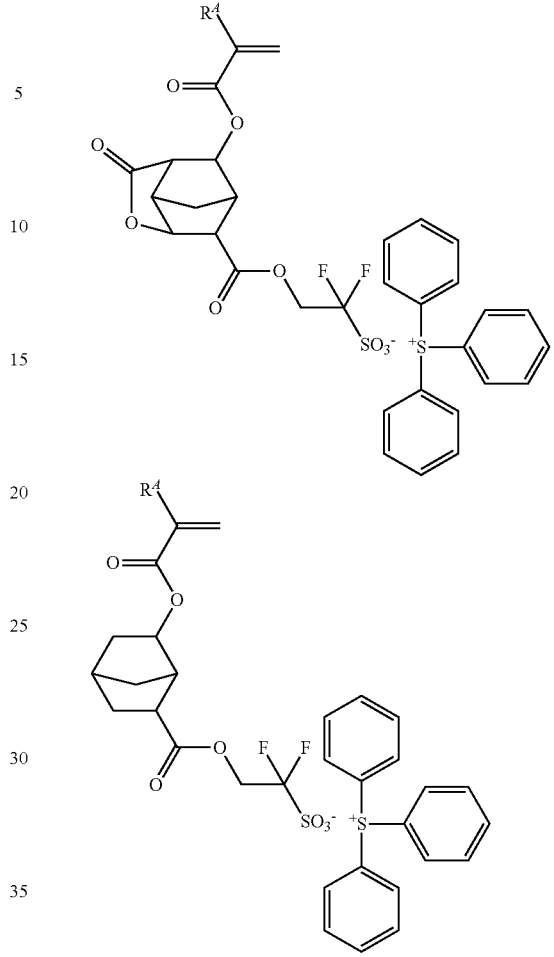

Other Structural Unit(s)

The other structural unit(s) may be exemplified by a structural unit including an alcoholic hydroxyl group, other than the above structural unit (III); a structural unit including a lactone structure, a cyclic carbonate structure, a sultone structure, or a combination thereof; and the like.

In the case in which the polymer (A) has the other structural unit(s), the upper limit of a proportion of the other structural unit(s) contained with respect to total structural units constituting the polymer (A) is preferably 20 mol %, and more preferably 10 mol %.

The lower limit of a proportion of the polymer (A) in the radiation-sensitive resin composition with respect to total components other than the organic solvent (D) of the radiation-sensitive resin composition is preferably 50% by mass, more preferably 70% by mass, and still more preferably 80% by mass. The upper limit of the proportion is preferably 99 mol %, and more preferably 95 mol %.

The lower limit of a polystyrene equivalent weight average molecular weight (Mw) of the polymer (A) as determined by gel permeation chromatography (GPC) is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (A) falls within the above range, the coating characteristics of the radiation-sensitive resin composition can be improved, and as a result, the sensitivity to exposure light, the LWR performance, and the resolution of the radiation-sensitive resin composition can be further improved.

The upper limit of a ratio (hereinafter, may be also referred to as "dispersity index" or "Mw/Mn") of the Mw to a polystyrene-equivalent number average molecular weight (Mn) of the polymer (A) as determined by GPC is preferably 5, more preferably 3, still more preferably 2, and particularly preferably 1.8. The lower limit of the ratio is typically 1.0, and preferably 1.1.

The Mw and Mn of the polymer herein are values determined using gel permeation chromatography (GPC) under the following conditions:

GPC columns: "G2000 HXL"×2, "G3000 HXL"×1, and "G4000 HXL"×1, available from Tosoh Corporation
column temperature: 40° C.
elution solvent: tetrahydrofuran
flow rate: 1.0 mL/min
sample concentration: 1.0% by mass
amount of injected sample: 100 uL
detector: differential refractometer
standard substance: mono-dispersed polystyrene (B) Acid Generating Agent The acid generating agent (B) is a compound (hereinafter, may be also referred to as "compound (B1)" or "compound (B2)," both being generally referred to as "compound (B)") represented by the following formula (1-1) or the following formula (1-2), each described later. The compound (B) is a compound which generates an acid by irradiation with a radioactive ray. The radioactive ray may be exemplified by radioactive rays similar to those exemplified as the exposure light in the exposing in the resist pattern-forming method of an other embodiment of the present invention, described later. The acid-labile group (α) included in the structural unit (II) which may be contained in the polymer (A), or the like is dissociated by an action of an acid generated from the compound (B) by irradiation with a radioactive ray, generating a carboxy group and creating a difference in solubility in the developer solution of the resist film between a light-exposed region and a light-unexposed region; accordingly, a resist pattern can be formed.

The lower limit of a temperature at which the acid generated from the compound (B) dissociates the acid-labile group (α) included in the structural unit (II), which may be contained in the polymer (A), is preferably 80° C., more preferably 90° C., and still more preferably 100° C. The upper limit of the temperature is preferably 130° C., more preferably 120° C., and still more preferably 110° C. The lower limit of a time period for the acid to dissociate the acid-labile group (α) is preferably 10 sec, and more preferably 1 min. The upper limit of the time period is preferably 10 min, and more preferably 2 min.

Herein, a part represented by A⁻ in the compound (B) represented by the following formula (1-1) or the following formula (1-2) is referred to as a "sulfonic acid anion," and a part other than the part represented by A⁻ is referred to as a "radiation-sensitive onium cation"; of the radiation-sensitive onium cations, the radiation-sensitive onium cation in the following formula (1-1) may be referred to as "radiation-sensitive onium cation (1-1)," and the radiation-sensitive onium cation in the following formula (1-2) may be referred to as "radiation-sensitive onium cation (1-2)."

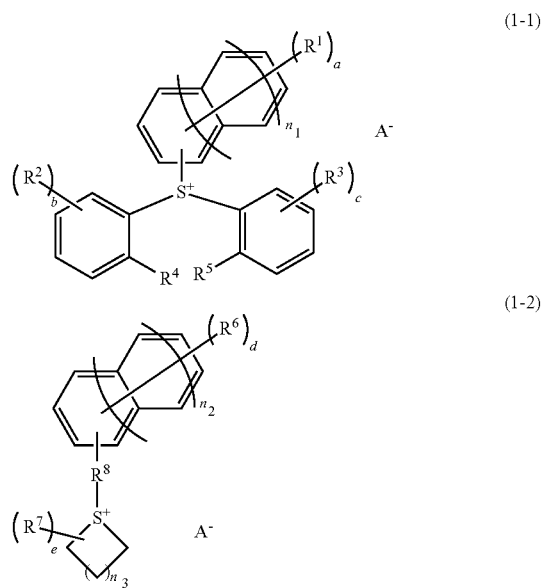

In each of the above formulae (1-1) and (1-2), A⁻ represents a monovalent sulfonic acid anion.

In the above formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^1$, $R^2$, and $R^3$ represents a fluorine atom or a monovalent fluorinated hydrocarbon group having 1 to 10 carbon atoms, in a case in which a is no less than 2, a plurality of $R^4$s are identical or different, in a case in which b is no less than 2, a plurality of $R^2$s are identical or different, and in a case in which c is no less than 2, a plurality of $R^3$s are identical or different; m is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond.

In the above formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; $n_2$ is 0 or 1; and $n_3$ is an integer of 0 to 3.

Examples of the monovalent organic group having 1 to 20 carbon atoms which may be represented by $R^1$, $R^2$, $R^3$, $R^6$, or $R^7$ include groups similar to those exemplified as the monovalent organic group having 1 to 20 carbon atoms which may be exemplified as $R^{12}$ in the above formula (5), and the like.

Examples of the halogen atom which may be represented by $R^1$, $R^2$, $R^3$, $R^6$, or $R^7$ include a fluorine atom, a chlorine atom, a bromine atom, and an iodine atom.

Examples of the monovalent fluorinated hydrogen group having 1 to 10 carbon atoms which may be represented by $R^1$, $R^2$, $R^3$, $R^4$, $R^5$, $R^6$, or $R^7$ include groups similar to those exemplified as the monovalent fluorinated hydrocarbon group having 1 to 10 carbon atoms which may be represented by $R^{13}$ or $R^{14}$ in the above formula (5).

Examples of the divalent organic group having 1 to 20 carbon atoms which may be represented by $R^8$ include groups obtained by removing one hydrogen atom from the groups exemplified as the monovalent organic group having 1 to 20 carbon atoms which may be represented by $R^{12}$ in the above formula (5).

In light of enabling further improvement in sensitivity to exposure light, $n^1$ and $n^2$ are each preferably 0.

$R^1$, $R^2$, $R^3$, $R^6$, and $R^7$ each represent preferably a fluorine atom or a monovalent perfluoroalkyl group having 1 to 10 carbon atoms, and more preferably a fluorine atom or a trifluoromethyl group. Furthermore, in light of enabling further improvement in the sensitivity to exposure light and the LWR performance, there are cases in which $R^1$, $R^2$, $R^3$, $R^6$, and $R^7$ are each preferably a trifluoromethyl group rather than a fluorine atom.

a is preferably 0 to 4, more preferably 0 to 3, and still more preferably 0 to 2; b is preferably 0 to 4, more preferably 0 to 3, and still more preferably 0 to 2; c is preferably 0 to 4, more preferably 0 to 3, and still more preferably 0 to 2; and a sum of a, b, and c is preferably 1 to 6, and more preferably 1 to 3. Furthermore, there are cases in which the sensitivity to exposure light is improved as the sum of a, b, and c increases, in the order of 1 to 3. In the case in which the sum of a, b, and c is 2, it is preferable that a is 0 and each of b and c is 1. In the case in which the sum of a, b, and c is 3, it is preferable that each of a, b, and c is 1, or that a is 3 and each of b and c is 0. In the case in which the sum of a, b, and c is 4, it is preferable that a is 0 and each of b and c is 2. In the case in which the sum of a, b, and c is 5, it is preferable that a is 1 and each of b and c is 2, or that a is 5 and each of b and c is 0. In the case in which the sum of a, b, and c is 6, it is preferable that each of a, b, and c is 2, or that a is 0 and each of b and c is 3. In the case in which the sum of a, b, and c is no less than 7, it is preferable that a, b, and c are all no less than 1.

It is preferable that at least one of $R^1$, $R^2$, and $R^3$ is in a para position with respect to a sulfonium cation ($S^+$).

It is preferable that $R^4$ and $R^5$ each represent a hydrogen atom, or that $R^4$ and $R^5$ taken together represent a single bond.

The radiation-sensitive onion cation is preferably the radiation-sensitive onium cation (1-1).

The radiation-sensitive onium cation (1-1) may be exemplified by radiation-sensitive onium cations (hereinafter, may be also referred to as "radiation-sensitive cations (1-1-1) to (1-1-14)") represented by the following formulae (1-1-1) to (1-1-14).

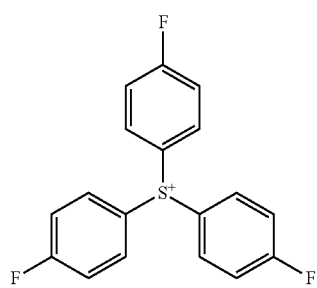

(1-1-1)

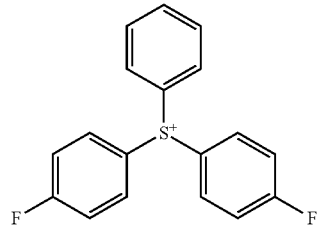

(1-1-2)

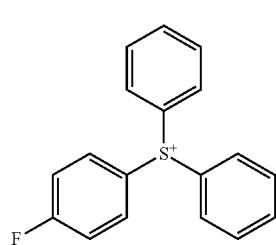

(1-1-3)

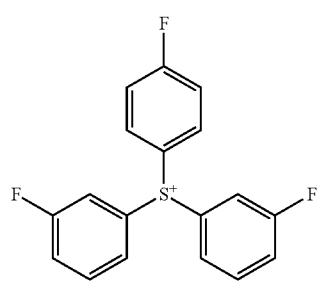

(1-1-4)

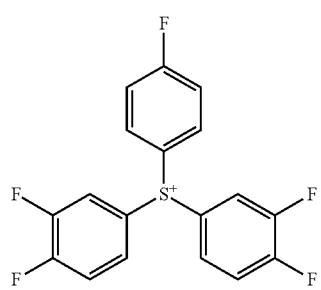

(1-1-5)

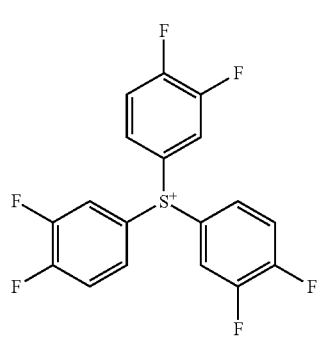

(1-1-6)

(1-1-7)
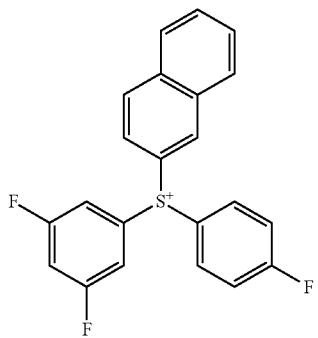

(1-1-8)
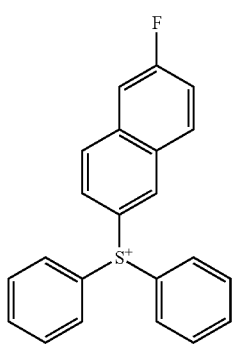

(1-1-9)
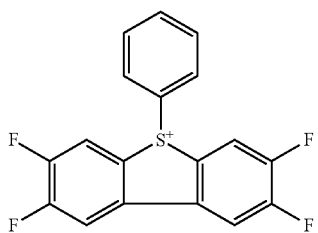

(1-1-10)
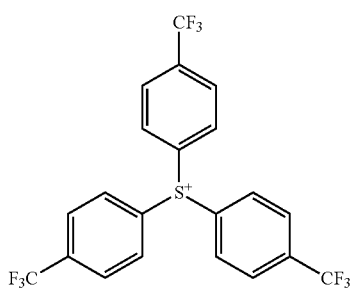

(1-1-11)
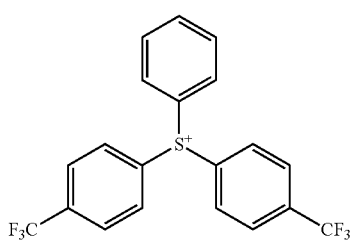

(1-1-12)
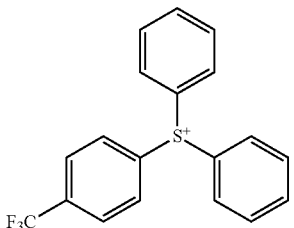

(1-1-13)
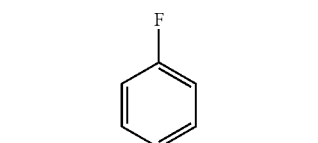

(1-1-14)
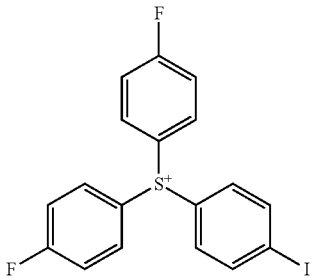

The monovalent sulfonic acid anion represented by A⁻ preferably includes a ring structure. When the sulfonic acid anion includes a ring structure, the LWR performance can be further improved.

The ring structure can be exemplified by an alicyclic structure, an aliphatic heterocyclic structure, and the like. Of these, the ring structure is preferably an adamantane structure, a norbornane structure, or a sultone structure, and more preferably a norbornane structure.

Furthermore, the monovalent sulfonic acid anion represented by A⁻ preferably includes a partial structure represented by the following formula (3). When the sulfonic acid anion includes the partial structure represented by the following formula (3), the sensitivity to exposure light, the LWR performance, and the resolution can be further improved.

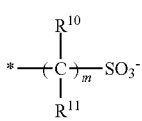

(3)

In the above formula (3), $R^{10}$ and $R^{11}$ each independently represent a hydrogen atom, a fluorine atom, a monovalent hydrocarbon group having 1 to 20 carbon atoms, or a monovalent fluorinated hydrocarbon group having 1 to 20 carbon atoms, wherein at least one of $R^{10}$ and $R^{11}$ is a fluorine atom or a monovalent fluorinated hydrocarbon group having 1 to carbon atoms; m is an integer of 1 to 10, wherein in a case in which m is no less than 2, a plurality of $R^{10}$s are identical or different and a plurality of $R^{11}$s are identical or different; and * denotes a binding site to a part other than the structure represented by the formula (3) in the sulfonic acid anion.

Examples of the monovalent hydrocarbon group having 1 to 20 carbon atoms which may be represented by $R^{10}$ or $R^{11}$ include groups similar to those exemplified as the monovalent hydrocarbon group having 1 to 20 carbon atoms which may be represented by $R^X$, $R^Y$, $R^Z$, $R^B$, $R^C$, $R^U$, $R^V$, or $R^W$ in the above formulae (4-1) to (4-3); and the like.

Examples of the monovalent fluorinated hydrocarbon group having 1 to 20 carbon atoms which may be represented by $R^{10}$ or $R^{11}$ include groups obtained by substituting with a fluorine atom at least one hydrogen atom contained in the groups exemplified as the monovalent hydrocarbon group having 1 to 20 carbon atoms which may be represented by $R^X$, $R^Y$, $R^Z$, $R^B$, $R^C$, $R^U$, $R^V$, or $R^W$ in the above formulae (4-1) to (4-3); and the like.

Furthermore, the sulfonic acid anion preferably further includes a cyclic acetal structure. When the sulfonic acid anion includes a cyclic acetal structure, the sensitivity to exposure light and the LWR performance can be further improved.

Examples of the sulfonic acid anion include sulfonic acid anions (hereinafter, may be also referred to as "sulfonic acid anions (A1) to (A13)" represented by the following formulae (A1) to (A13), and the like.

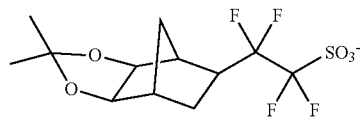

(A1)

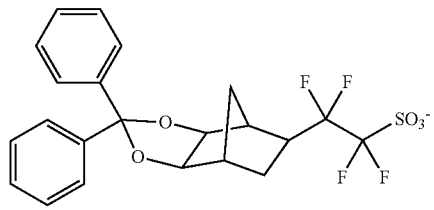

(A2)

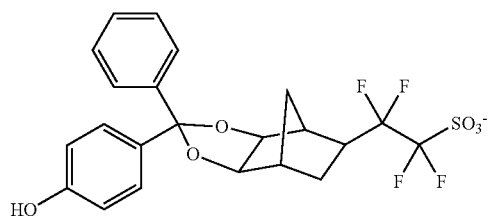

(A3)

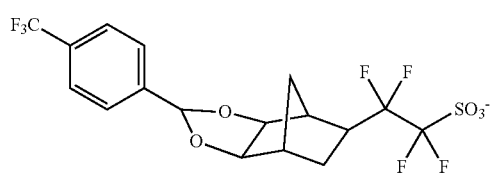

(A4)

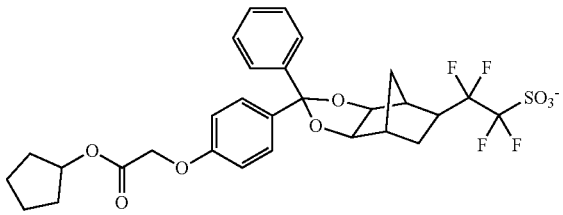

(A5)

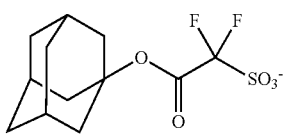

(A6)

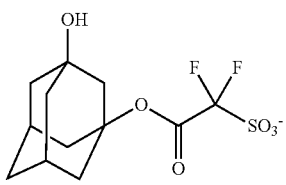

(A7)

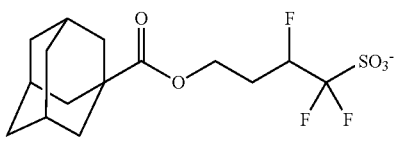

(A8)

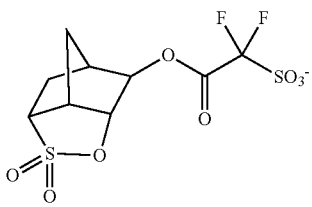

(A9)

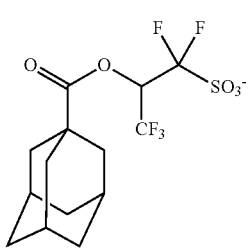

(A10)

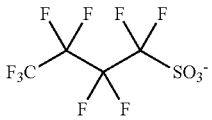

(A11)

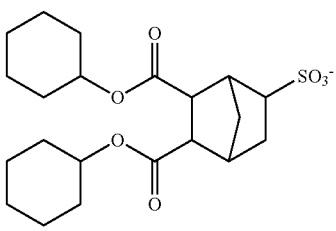

(A12)

(A13)

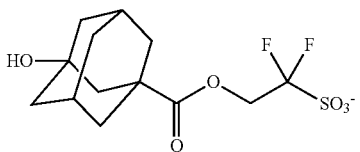

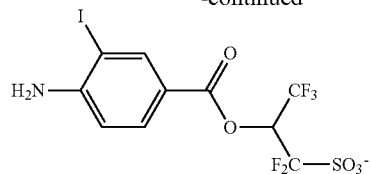

The sulfonic acid anion is preferably one of the sulfonic acid anions (A1) to (A10) or the sulfonic acid anion (A13), and more preferably one of the sulfonic acid anions (A1) to (A5).

Furthermore, the ring structure included in the sulfonic acid anion may also be preferably an aromatic ring structure having at least one iodine atom as a substituent. The aromatic ring has as a substituent, preferably 1 to 4 iodine atoms, more preferably 1 to 3 iodine atoms, and still more preferably 2 to 3 iodine atoms. The aromatic ring structure is preferably a benzene ring or a naphthalene ring, and more preferably a benzene ring.

Examples of the sulfonic acid anion including the aromatic ring structure having at least one iodine atom as a substituent include sulfonic acid anions represented by the following formulae, and the like.

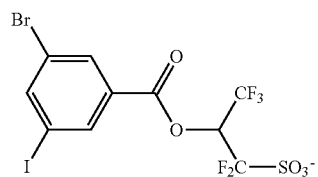

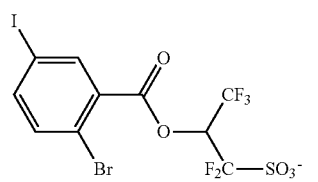

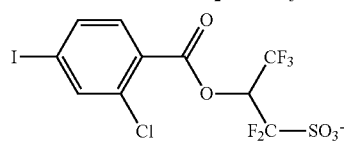

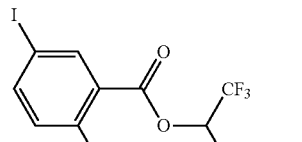

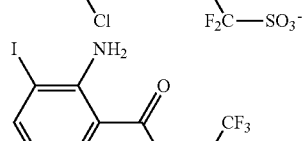

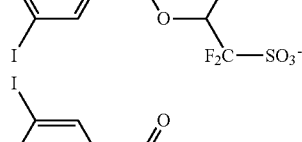

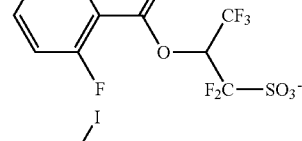

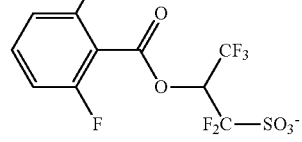

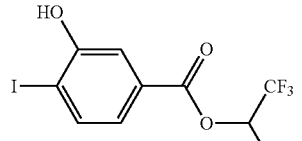

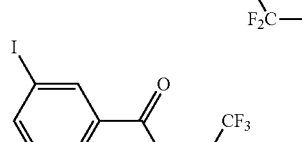

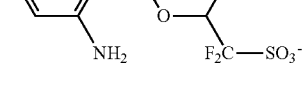

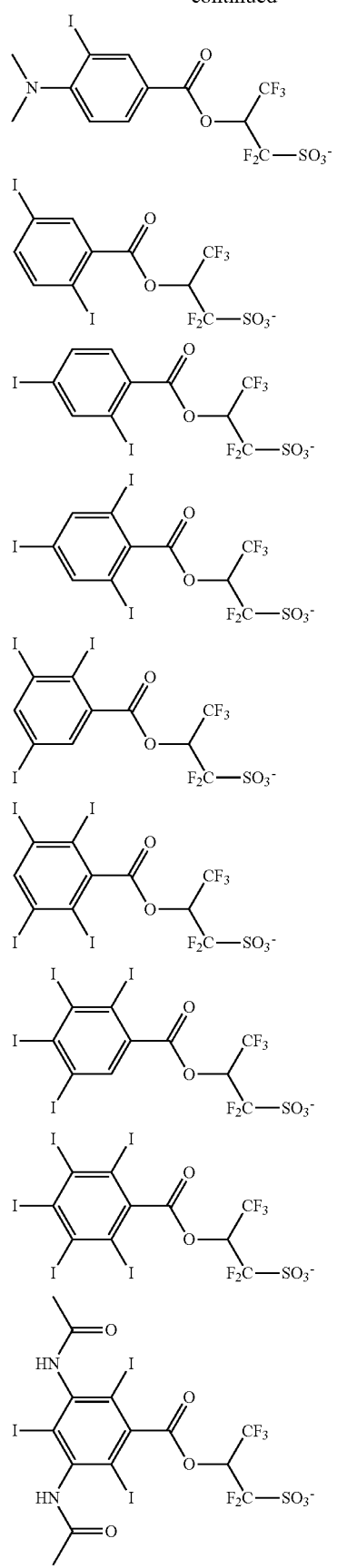
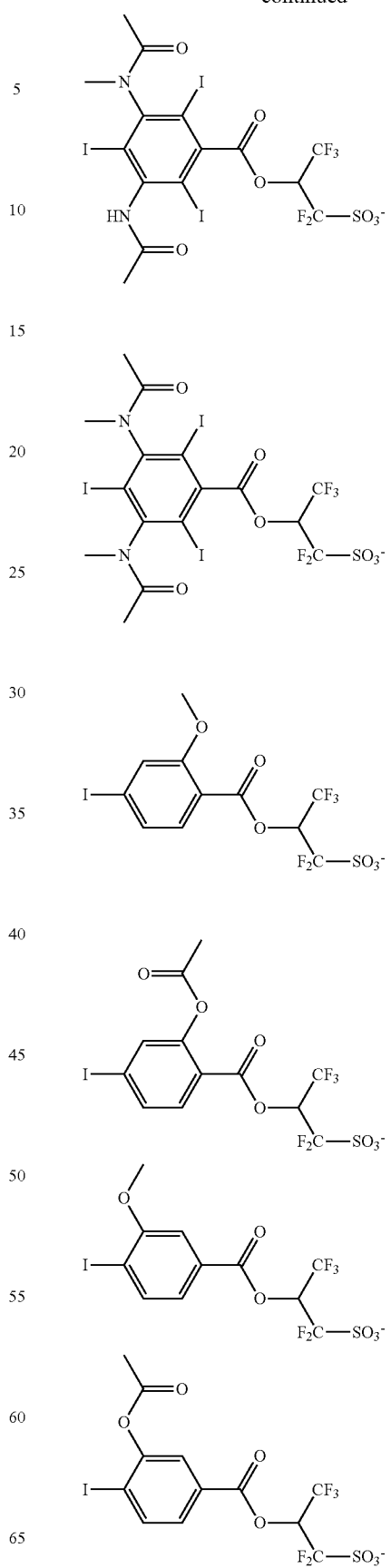

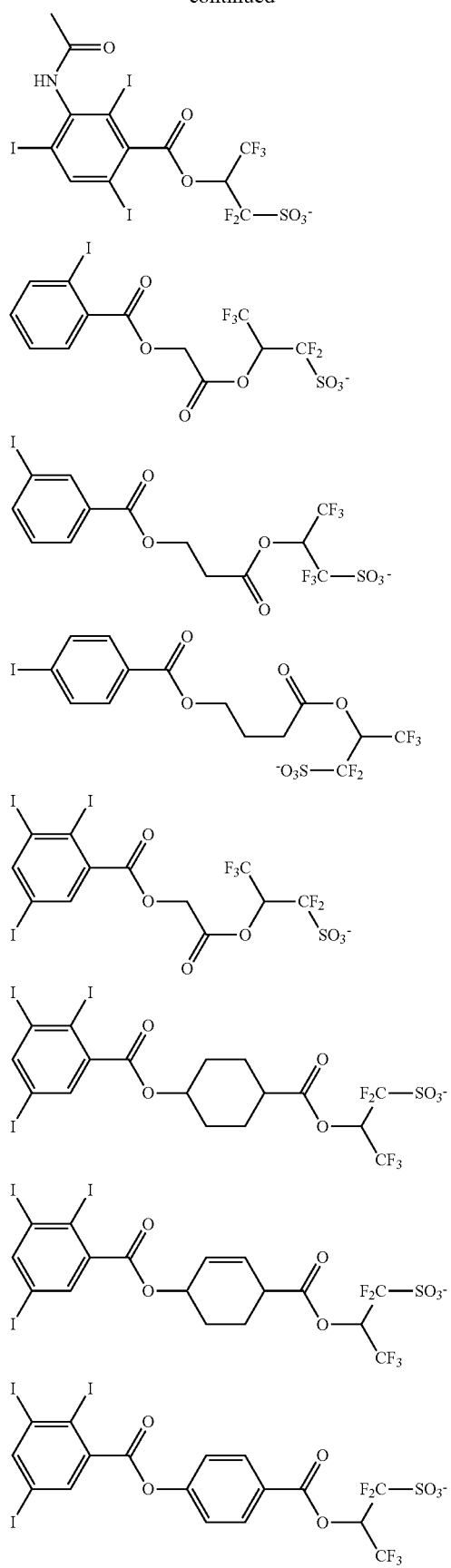
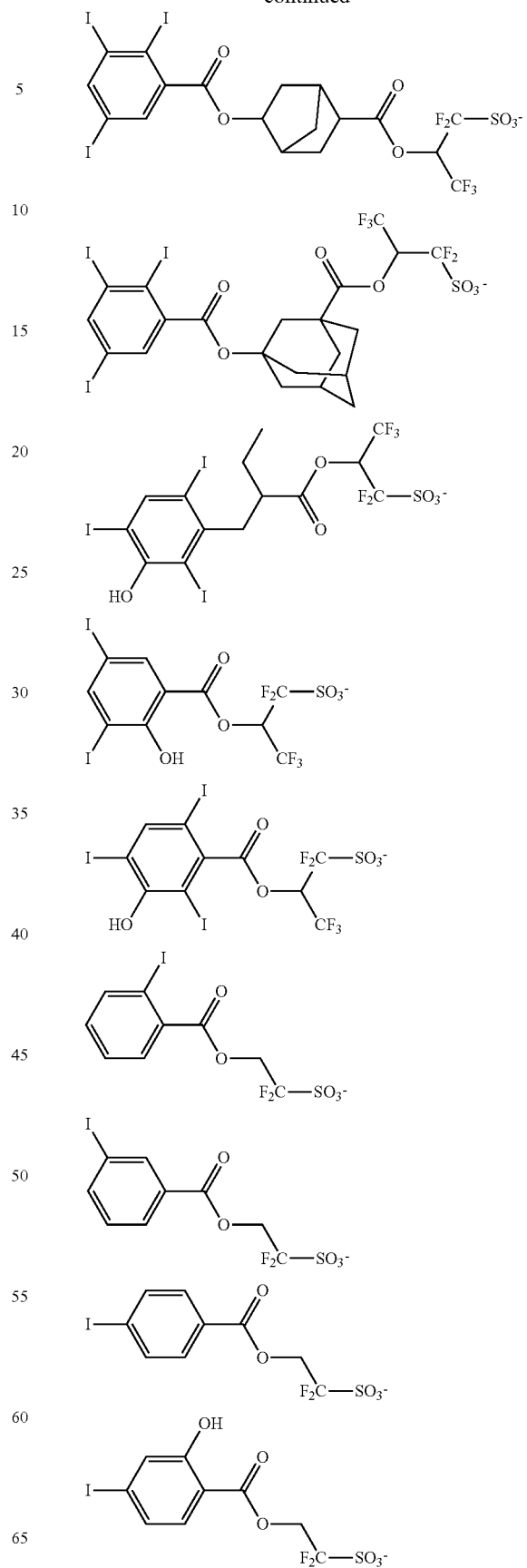

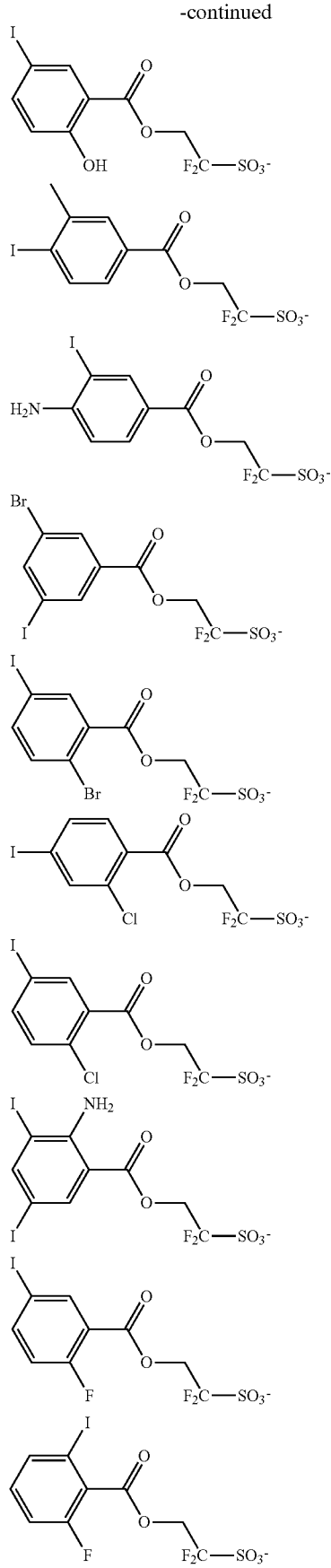
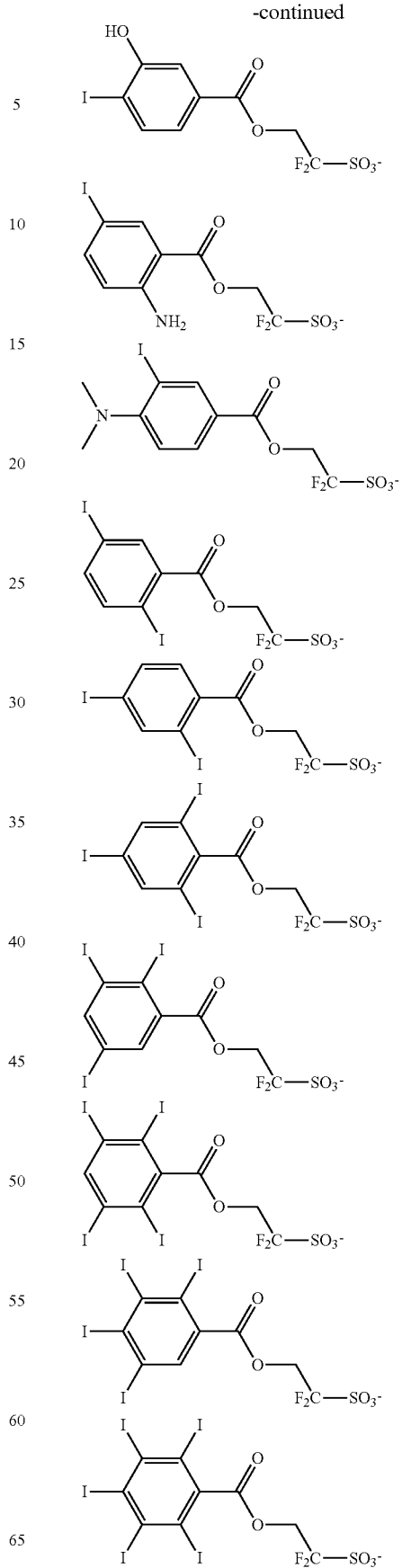

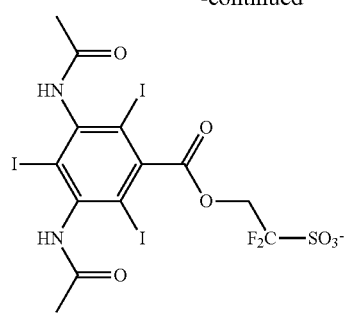
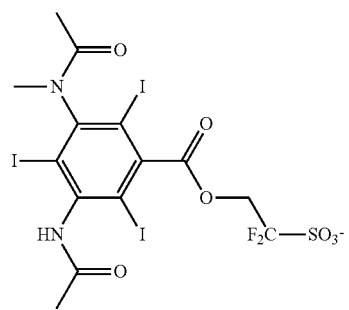
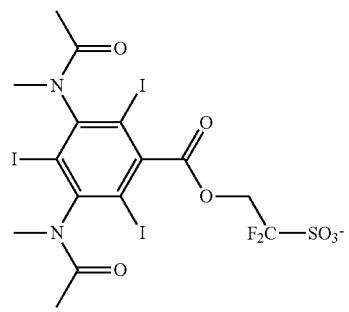
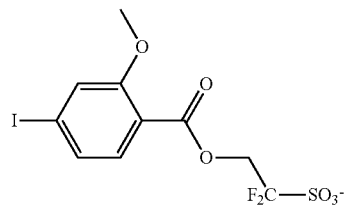
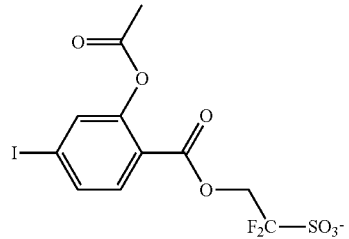
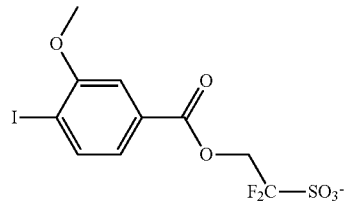
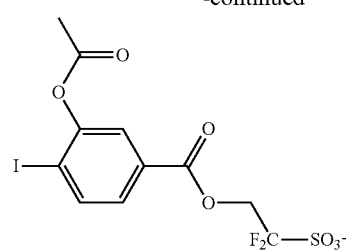
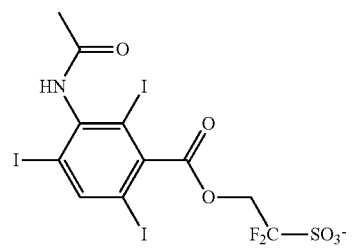
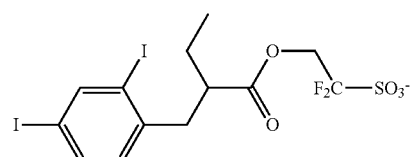
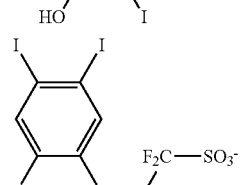
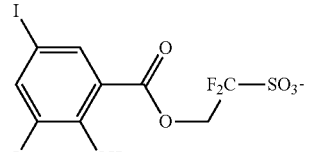
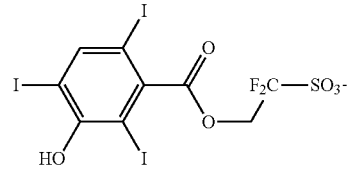
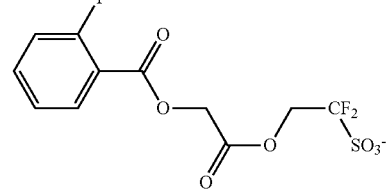
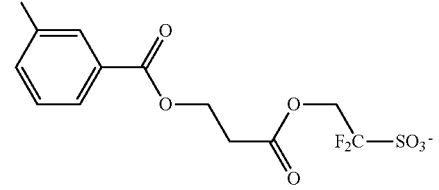

-continued
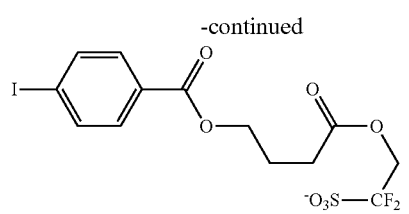
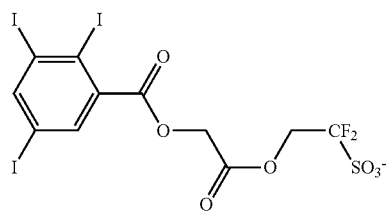
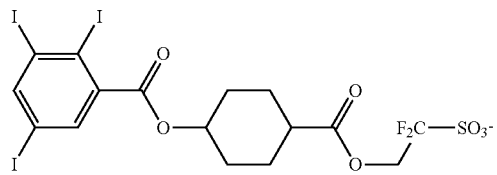
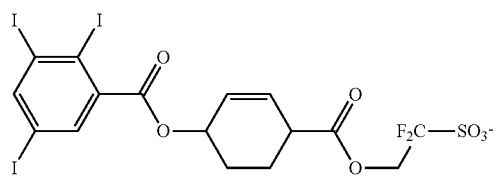
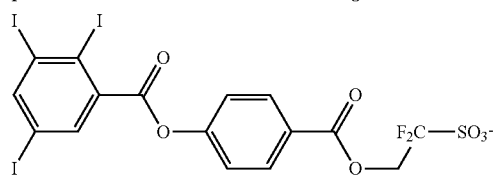
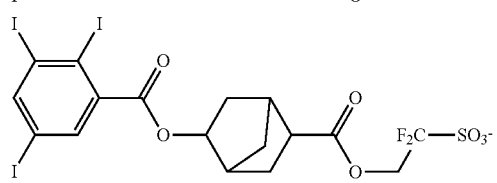
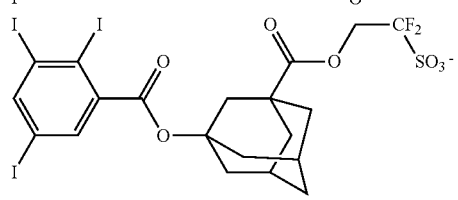
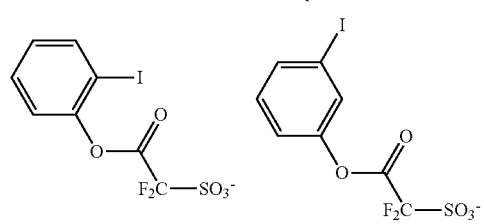
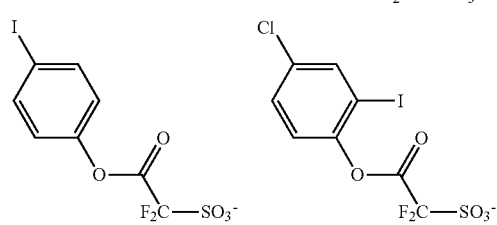
-continued
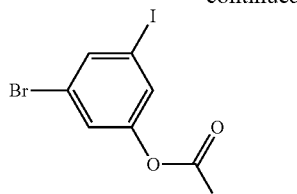
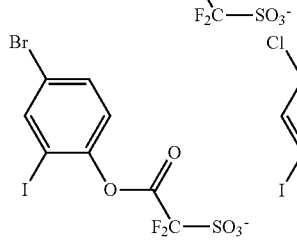
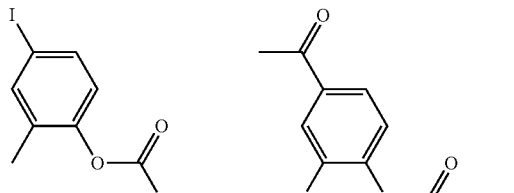
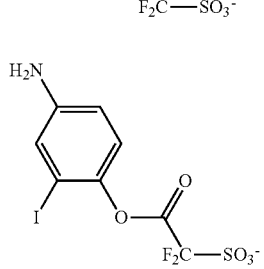
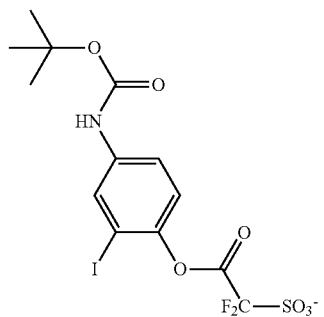
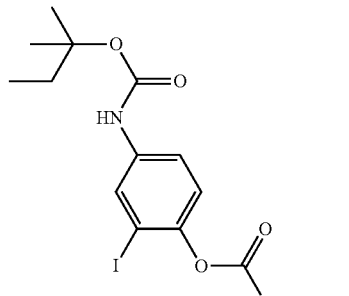
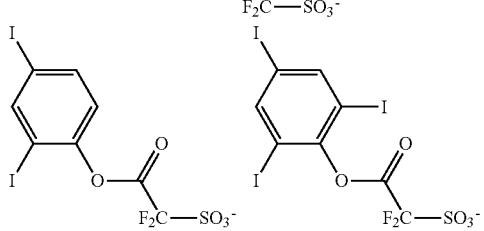

-continued
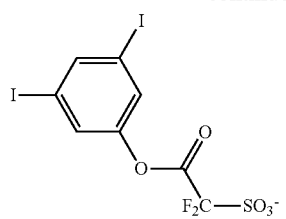
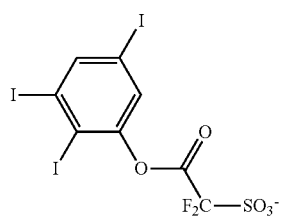
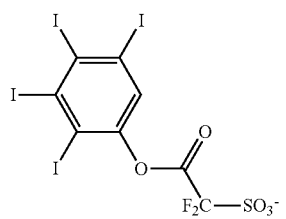
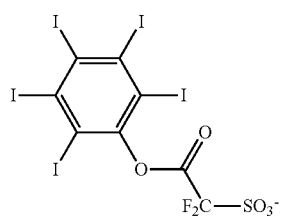
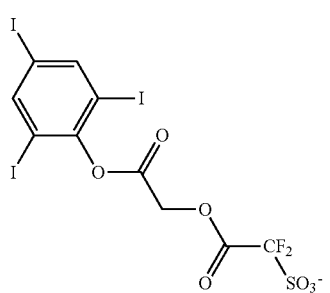
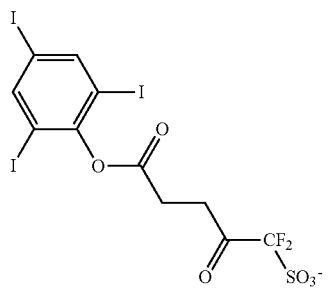
-continued
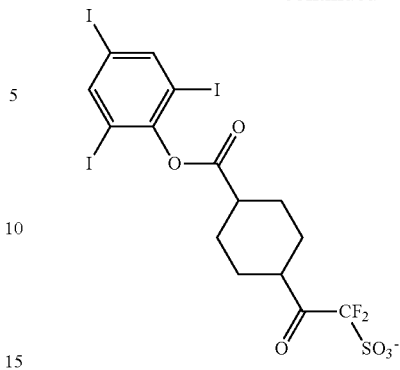
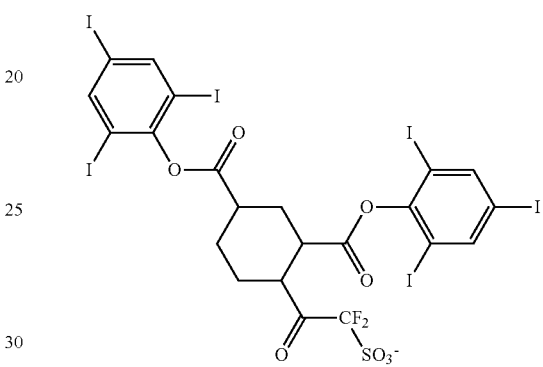
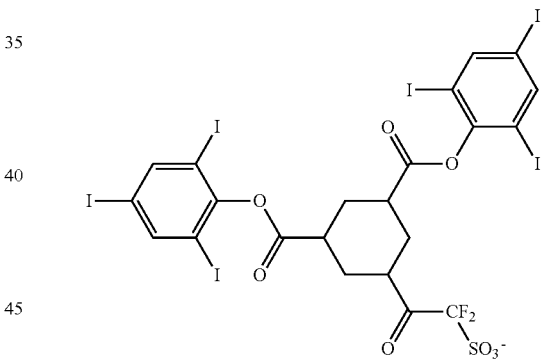
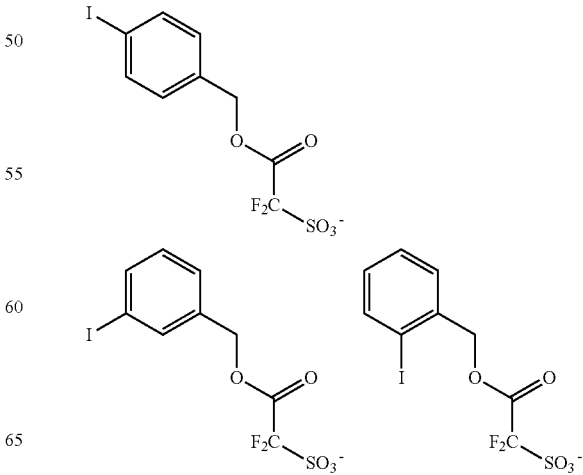

-continued
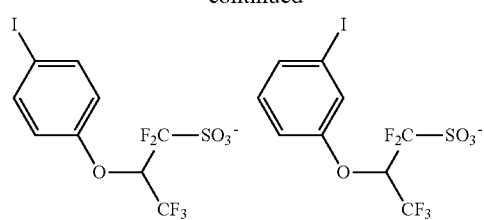
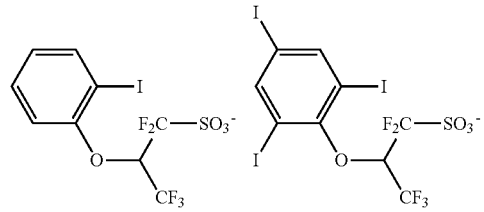
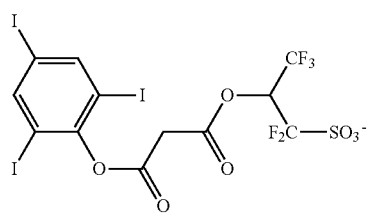
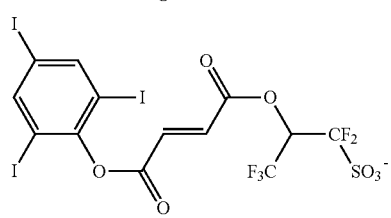
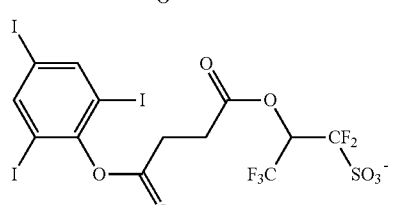
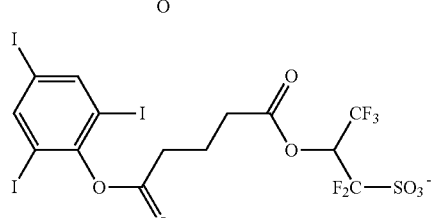
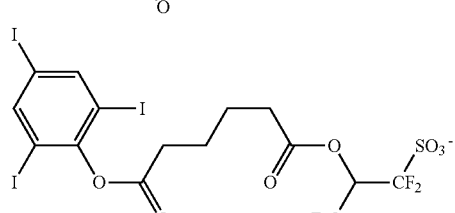
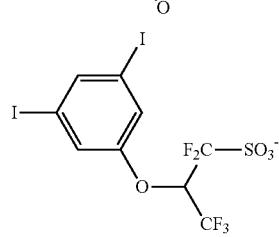
-continued
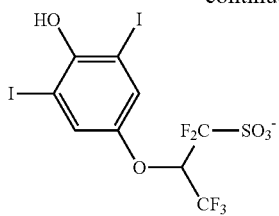
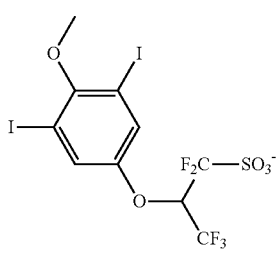
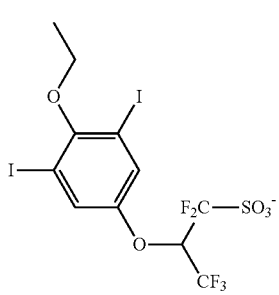
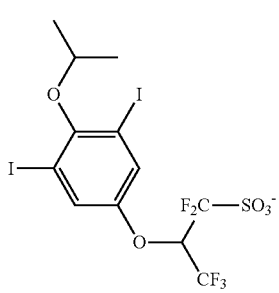
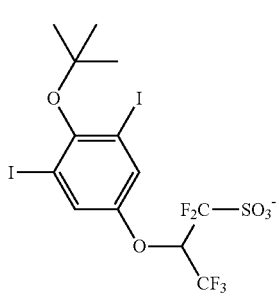
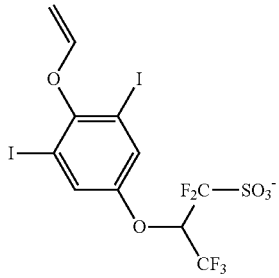

-continued

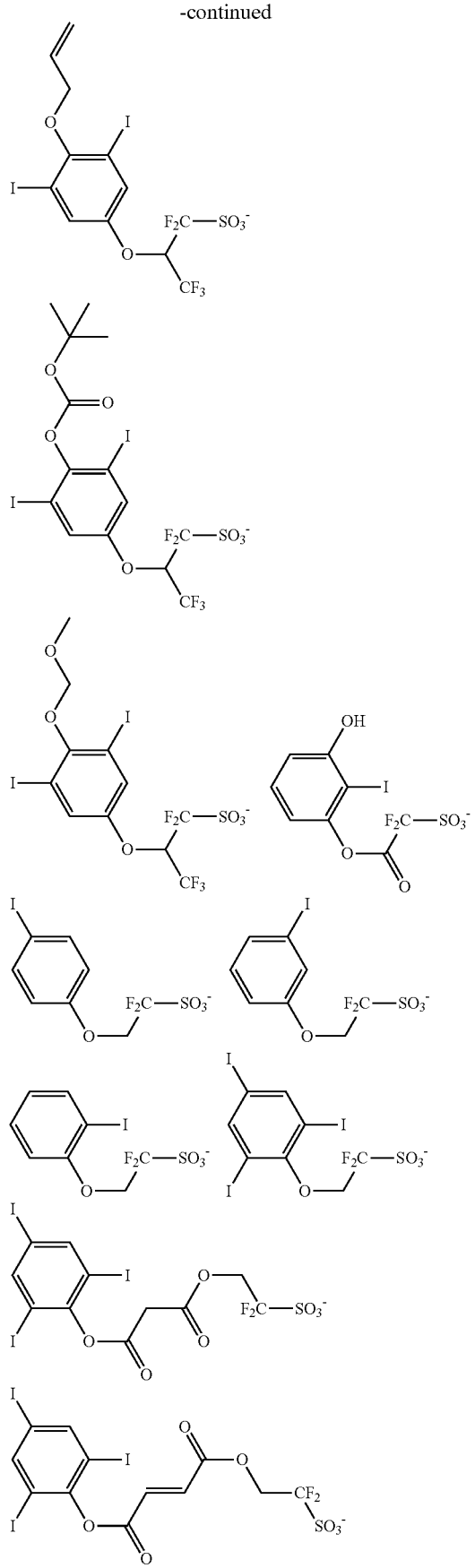

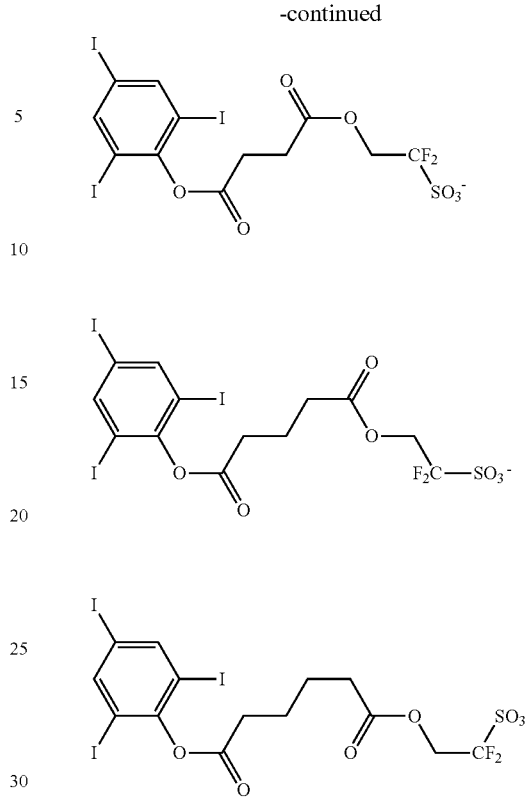

Furthermore, the ring structure included in the sulfonic acid anion preferably contains a steroid skeleton or a 9,10-ethanoanthracene skeleton.

"Steroid skeleton" as referred to herein means a ring structure represented by the following formula (St), in which three 6-membered rings and one 4-membered ring have been condensed.

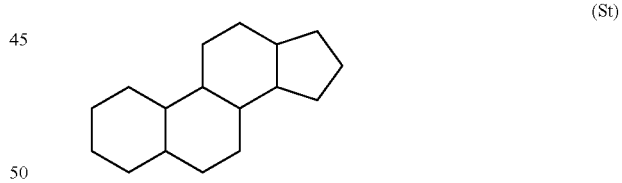

(St)

"9,10-ethanoanthracene skeleton" as referred to herein means a ring structure represented by the following formula.

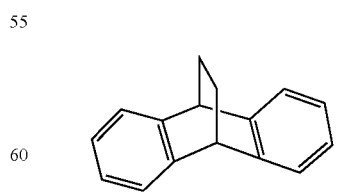

Examples of the sulfonic acid anion containing the steroid skeleton include sulfonic acid anions represented by the following formulae, and the like. In each of the following formulae, k is an integer of 1 to 5.

-continued
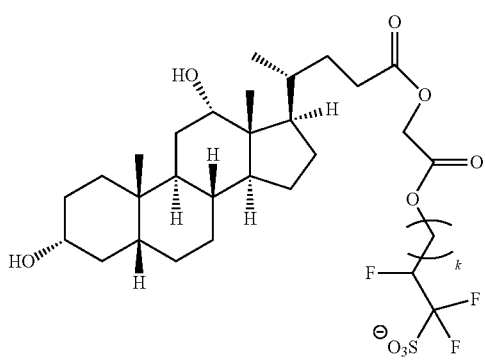
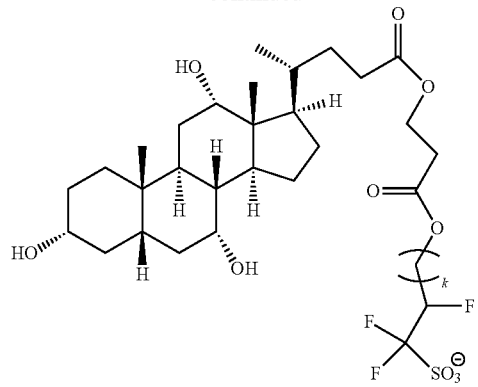
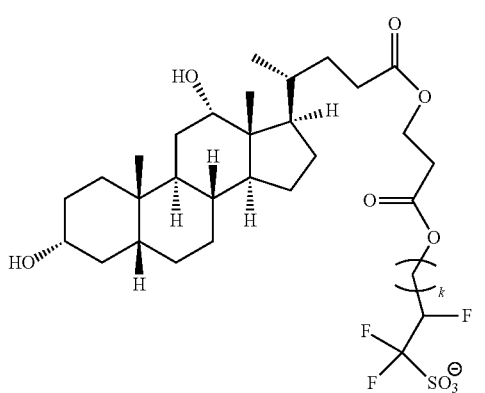
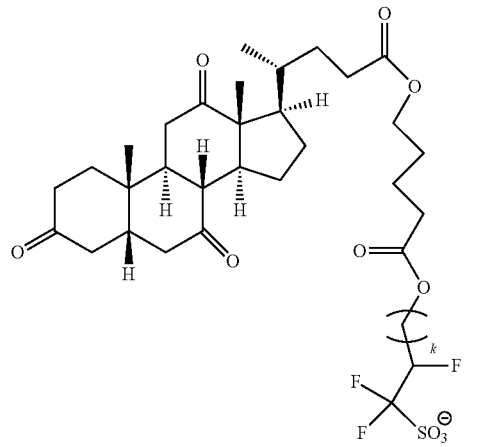
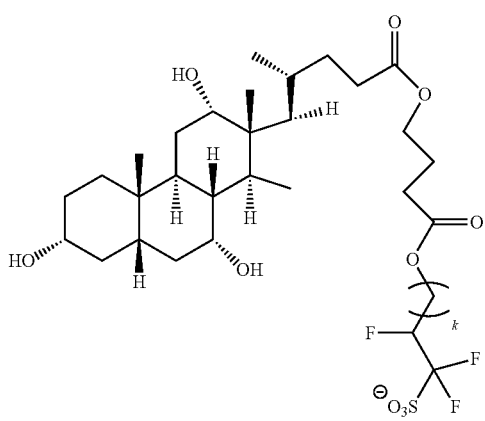
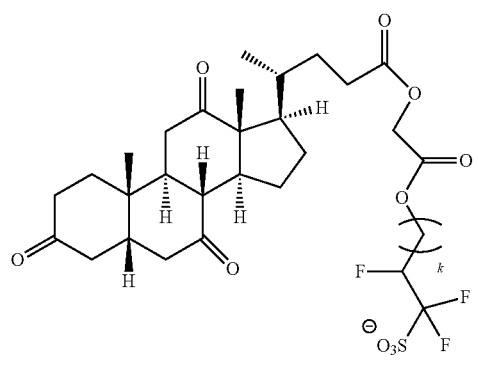
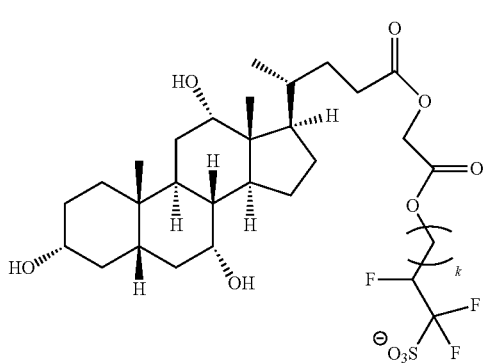
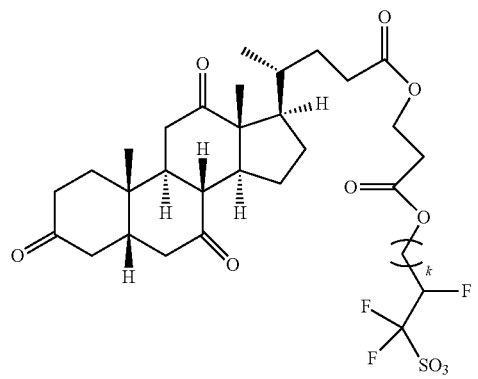

-continued
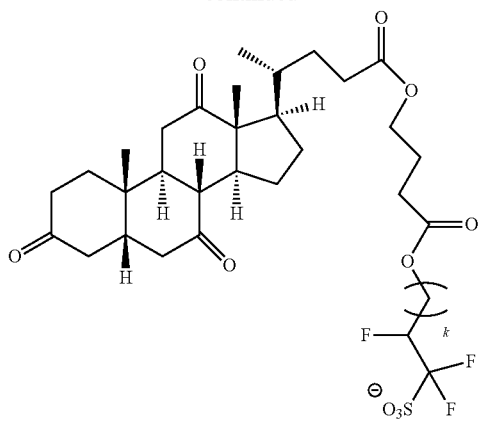
Examples of the sulfonic acid anion containing the 9,10-ethanoanthracene skeleton include sulfonic acid anions represented by the following formulae, and the like.
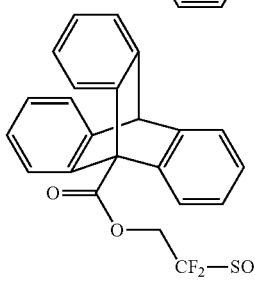
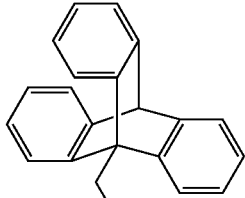
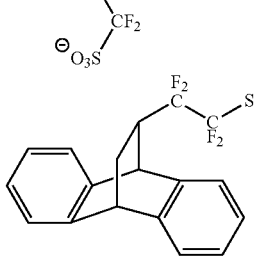
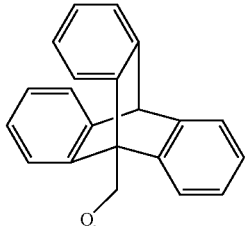
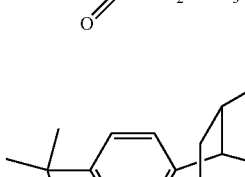
-continued
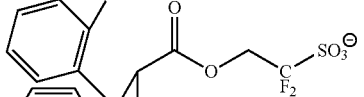
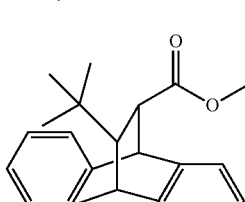
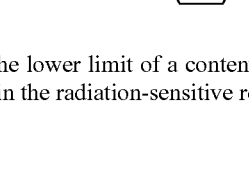
The lower limit of a content of the acid generating agent (B) in the radiation-sensitive resin composition with respect to 100 parts by mass of the polymer (A) is preferably 5 parts by mass, more preferably 10 parts by mass, and still more preferably 15 parts by mass. The upper limit of the content is preferably 60 parts by mass, more preferably 55 parts by mass, and still more preferably 50 parts by mass. When the content of the acid generating agent (B) falls within the above range, the sensitivity to exposure light, the LWR performance, and the sensitivity can be further improved.

(C) Acid Diffusion Control Agent

The acid diffusion control agent (C) is a compound (hereinafter, may be also referred to as "compound (C)") represented by the following formula (2), described later. The compound (C) controls a diffusion phenomenon in the resist film of the acid generated from the acid generating agent (B) and the like upon exposure, thereby having an action of inhibiting unwanted chemical reactions in an unexposed region.

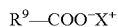  (2)

In the above formula (2), $R^9$ represents a monovalent organic group having 1 to 30 carbon atoms; and $X^+$ represents a monovalent radiation-sensitive onium cation.

The monovalent organic group having 1 to 30 carbon atoms represented by $R^9$ is exemplified by: a monovalent hydrocarbon group having 1 to 30 carbon atoms; a group (hereinafter, may be also referred to as "group (α')") that includes a divalent hetero atom-containing group between two adjacent carbon atoms of the monovalent hydrocarbon group having 1 to 30 carbon atoms; a group (hereinafter, may be also referred to as "group (β')") obtained by substituting with a monovalent hetero atom-containing group, a part or all of hydrogen atoms included in the monovalent hydrocarbon group having 1 to 30 carbon atoms; a group (hereinafter, may be also referred to as "group (γ')") obtained by substituting with a monovalent hetero atom-containing group, a part or all of hydrogen atoms included in the group (α'); and the like. Of these, an aryl group obtained by substitution with at least one type of hetero atom-containing group selected from the group consisting of a hydroxy group, a halogen atom, and a halogenated hydrocarbon group is preferred, and a phenyl group obtained by substitution with at least one type of hetero atom-containing group selected from the group consisting of a hydroxy group, a fluorine atom, an iodine atom, and a trifluoromethyl group is more preferred. Moreover, a monovalent organic group having 7 to carbon atoms and including an aryl group obtained by substitution with at least one type of hetero atom-containing group selected from the group consisting of a hydroxy group, a fluorine atom, an iodine atom, and a trifluoromethyl group is also preferred.

Herein, the part represented by $R^9$—$COO^-$ in the compound (C) represented by the above formula (2) is referred to as a "weak acid anion," and the part represented by $X^+$ is referred to as a "radiation-sensitive onium cation."

Examples of the weak acid anion include anions represented by the following formulae (C1) to (C5), and the like.

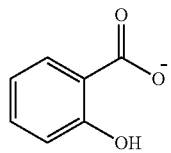  (C1)

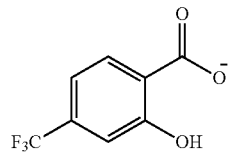  (C2)

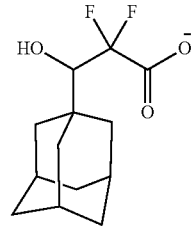  (C3)

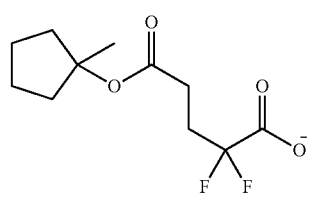  (C4)

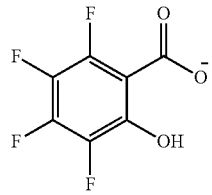  (C5)

Examples of the radiation-sensitive onium cation include a triphenylsulfonium cation, a phenyldibenzothiophenium cation, a 1-naphthyldiphenylsulfonium cation, a 2-naphthyldiphenylsulfonium cation, the radiation-sensitive onium cation in the above formula (1-1), the radiation-sensitive onium cation in the above formula (1-2), and the like.

A compound in which the weak acid anion and the radiation-sensitive onium cation have been appropriately combined may be used as the compound (C).

The lower limit of a proportion of the acid diffusion control agent (C) in the radiation-sensitive resin composition with respect to 100 mol % of the acid generating agent (B) is preferably 1 mol %, more preferably 5 mol %, and still more preferably 10 mol %. The upper limit of the content is preferably 100 mol %, more preferably 50 mol %, and still more preferably 30 mol %. When the content of the acid diffusion control agent (C) falls within the above range, the sensitivity to exposure light, the LWR performance, and the resolution of the resist pattern to be formed by the radiation-sensitive resin composition can be further improved.

(D) Organic Solvent

The radiation-sensitive resin composition typically contains the organic solvent (D). The organic solvent (D) is not particularly limited as long as it is a solvent capable of dissolving or dispersing at least the polymer (A), the acid generating agent (B), and the acid diffusion control agent (C), as well as the optional components) which is/are contained as necessary.

The organic solvent (D) is exemplified by an alcohol solvent, an ether solvent, a ketone solvent, an amide solvent, an ester solvent, a hydrocarbon solvent, and the like. Either one type, or two or more types of the organic solvent (D) may be used.

Examples of the alcohol solvent include:

aliphatic monohydric alcohol solvents having 1 to 18 carbon atoms such as 4-methyl-2-pentanol and n-hexanol;

alicyclic monohydric alcohol solvents having 3 to 18 carbon atoms such as cyclohexanol;

polyhydric alcohol solvents having 2 to 18 carbon atoms such as 1,2-propylene glycol;

polyhydric alcohol partial ether solvents having 3 to 19 carbon atoms such as propylene glycol-1-monomethyl ether; and the like.

Examples of the ether solvent include:

dialkyl ether solvents such as diethyl ether, dipropyl ether, dibutyl ether, dipentyl ether, diisoamyl ether, dihexyl ether, and diheptyl ether;

cyclic ether solvents such as tetrahydrofuran and tetrahydropyran;

aromatic ring-containing ether solvents such as diphenyl ether and anisole; and the like.

Examples of the ketone solvent include:

chain ketone solvents such as acetone, methyl ethyl ketone, methyl-n-propyl ketone, methyl-n-butyl ketone, diethyl ketone, methyl-iso-butyl ketone, 2-heptanone, ethyl-n-butyl ketone, methyl-n-hexyl ketone, di-iso-butyl ketone, and trimethylnonanone;

cyclic ketone solvents such as cyclopentanone, cyclohexanone, cycloheptanone, cyclooctanone, and methylcyclohexanone; 2,4-pentanedione, acetonylacetone, and acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide, and N-methylpropionamide; and the like.

Examples of the ester solvent include:

monocarboxylic acid ester solvents such as n-butyl acetate and ethyl lactate;

lactone solvents such as γ-butyrolactone and δ-valerolactone;

polyhydric alcohol carboxylate solvents such as propylene glycol acetate;

polyhydric alcohol partial ether carboxylate solvents such as propylene glycol monomethyl ether acetate;

polyhydric carboxylic acid diester solvents such as diethyl oxalate;

carbonate solvents such as dimethyl carbonate and diethyl carbonate; and the like.

Examples of the hydrocarbon solvent include:

aliphatic hydrocarbon solvents having 5 to 12 carbon atoms such as n-pentane and n-hexane;

aromatic hydrocarbon solvents having 6 to 16 carbon atoms such as toluene and xylene; and the like.

The organic solvent (D) is preferably the alcohol solvent and/or the ester solvent, more preferably the polyhydric alcohol partial ether solvent having 3 to 19 carbon atoms and/or the polyhydric alcohol partial ether carboxylate solvent, and still more preferably propylene glycol-1-monomethyl ether and/or propylene glycol monomethyl ether acetate.

In the case of the organic solvent (D) being contained in the radiation-sensitive resin composition, the lower limit of a proportion of the organic solvent (D) with respect to all components contained in the radiation-sensitive resin composition is preferably 50% by mass, more preferably 60% by mass, still more preferably 70% by mass, and particularly preferably 80% by mass. The upper limit of the proportion is preferably 99.9% by mass, more preferably 99.5% by mass, and still more preferably 99.0% by mass.

Other Optional Component(s)

The other optional component(s) is/are exemplified by a surfactant and the like. The radiation-sensitive resin composition may contain one, or two or more types each of the other optional component(s).

Resist Pattern-Forming Method

The resist pattern-forming method of the other embodiment of the present invention includes: a step of applying the radiation-sensitive resin composition of the one embodiment of the invention directly or indirectly on a substrate (hereinafter, may be also referred to as "applying step"); a step of exposing a resist film formed by the applying step (hereinafter, may be also referred to as "exposing step"); and a step of developing the resist film exposed (hereinafter, may be also referred to as "developing step").

According to the resist pattern-forming method, due to using the radiation-sensitive resin composition of the one embodiment of the present invention as the radiation-sensitive resin composition in the applying step, formation of a resist pattern having favorable sensitivity to exposure light and superiority with regard to both of the LWR performance and the sensitivity is enabled.

Each step included in the resist pattern-forming method will be described below.

Applying Step

In this step, the radiation-sensitive resin composition is applied directly or indirectly on the substrate. By this step, the resist film is directly or indirectly formed on the substrate.

In this step, the radiation-sensitive resin composition of the one embodiment of the present invention is used as the radiation-sensitive resin composition.

The substrate is exemplified by a conventionally well-known substrate such as a silicon wafer, a wafer coated with silicon dioxide or aluminum, and the like. Furthermore, the case of indirectly applying the radiation-sensitive resin composition on the substrate is exemplified by a case of applying the radiation-sensitive resin composition on an antireflective film formed on the substrate, and the like. Examples of such an antireflective film include an organic or inorganic antireflective film disclosed in Japanese Examined Patent Application, Publication No. H6-12452, Japanese Unexamined Patent Application, Publication No. S59-93448, and the like.

An application procedure is exemplified by spin-coating, cast coating, roll-coating, and the like. After the application, prebaking (hereinafter, may be also referred to as "PB") may be carried out as needed for evaporating the solvent remaining in the coating film. The lower limit of a PB temperature is preferably 60° C., and more preferably 80° C. The upper limit of the PB temperature is preferably 150° C., and more preferably 140° C. The lower limit of a PB time period is preferably 5 sec, and more preferably 10 sec. The upper limit of the PB time period is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm.

Exposing Step

In this step, the resist film formed by the applying step is exposed. This exposure is carried out by irradiation with exposure light through a photomask (through a liquid immersion medium such as water, as the case may be). Examples of the exposure light include: electromagnetic waves such as visible light rays, ultraviolet rays, far ultraviolet rays, extreme ultraviolet rays (EUV), X-rays, and γ-rays; charged particle rays such as electron beams and α-rays; and the like, which may be selected in accordance with a line width and the like of the intended pattern. Of these, far ultraviolet rays, EUV, or electron beams are preferred; an ArF excimer laser beam (wavelength: 193 nm), a KrF excimer laser beam (wavelength: 248 nm), EUV (wavelength: 13.5 nm), or an electron beam is more preferred; an ArF excimer laser beam, EUV, or an electron beam is still more preferred; and EUV or an electron beam is particularly preferred.

It is preferred that post exposure baking (hereinafter, may be also referred to as "PEB") is carried out after the exposure to promote dissociation of the acid-labile group included in the polymer (A), etc. mediated by the acid generated from the acid generating agent (B), etc. upon the exposure in exposed regions of the resist film. This PEB enables an increase in a difference in solubility of the resist film in a developer solution between the light-exposed regions and light-unexposed regions. The lower limit of a PEB temperature is preferably 50° C., more preferably 80° C., and still more preferably 100° C. The upper limit of the PEB temperature is preferably 180° C., and more preferably 130° C. The lower limit of a PEB time period is preferably 5 sec, more preferably 10 sec, and still more preferably 30 sec. The upper limit of the PEB time period is preferably 600 sec, more preferably 300 sec, and still more preferably 100 sec.

Developing Step

In this step, the resist film exposed is developed. Consequently, formation of a predetermined resist pattern is enabled. The development is typically followed by washing with a rinse agent such as water or an alcohol and then drying. The development procedure in the developing step may be carried out by either development with an alkali, or development with an organic solvent.

In the case of the development with an alkali, the developer solution for use in the development is exemplified by: alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (hereinafter, may be also referred to as "TMAH"), pyrrole, piperidine, choline, 1,8-diazabicyclo-[5.4.0]-7-undecene, and 1,5-diazabicyclo-[4.3.0]-5-nonene; and the like. Of these, an aqueous TMAH solution is preferred, and a 2.38% by mass aqueous TMAH solution is more preferred.

In the case of the development with an organic solvent, the developer solution is exemplified by: an organic solvent such as a hydrocarbon solvent, an ether solvent, an ester solvent, a ketone solvent, and an alcohol solvent; a solution containing the organic solvent; and the like. An exemplary organic solvent includes one, or two or more types of the solvents exemplified as the organic solvent (D) in the radiation-sensitive resin composition of the one embodiment of the present invention, and the like. Of these, the ester solvent or the ketone solvent is preferred. The ester solvent is preferably an acetic acid ester solvent, and more preferably n-butyl acetate. The ketone solvent is preferably a chain ketone, and more preferably 2-heptanone. The lower limit of a content of the organic solvent in the developer solution is preferably 80% by mass, more preferably 90% by mass, still more preferably 95% by mass, and particularly preferably 99% by mass. Components other than the organic solvent in the developer solution are exemplified by water, silicone oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate, which is rotated at a constant speed, while scanning with a developer solution-application nozzle at a constant speed; and the like.

The resist pattern to be formed according to the resist pattern-forming method is exemplified by a line-and-space pattern, a hole pattern, and the like.

EXAMPLES

Hereinafter, the present invention is explained in detail by way of Examples, but the present invention is not in any way limited to these Examples. Physical property values in the Examples were measured as described below.

Weight Average Molecular Weight (Mw), Number Average Molecular Weight (Mn), and Dispersity Index (Mw/Mn)

Measurements of the weight average molecular weight (Mw) and the number average molecular weight (Mn) of the polymer were carried out by gel permeation chromatography (GPC) using GPC columns available from Tosoh Corporation ("G2000 HXL"×2, "G3000 HXL"×1, and "G4000 HXL"×1) under the following analytical conditions. Furthermore a dispersity index (Mw/Mn) was calculated according to measurement results of the Mw and the Mn.

elution solvent: tetrahydrofuran flow rate: 1.0 mL/min sample concentration: 1.0% by mass amount of injected sample: 100 uL column temperature: 40° C.

detector: differential refractometer standard substance: mono-dispersed polystyrene Proportions of Structural Units Proportions of each structural unit in the polymers were determined by a $^{13}$C-NMR analysis using a nuclear magnetic resonance apparatus ("JNM-Delta400," available from JEOL, Ltd.).

Synthesis of Polymer (A)

Monomers (hereinafter, may be also referred to as "monomers (M-1) to (M-11)") represented by the following formulae (M-1) to (M-11) were used in synthesizing the polymer (A). In the following Synthesis Examples, unless otherwise specified particularly, "parts by mass" means a value, provided that the total mass of the monomers used was 100 parts by mass, and "mol %" means a value, provided that the total mol number of the monomers used was 100 mol %.

(M-1) 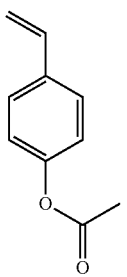
(M-2) 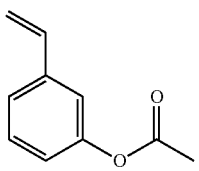
(M-3) 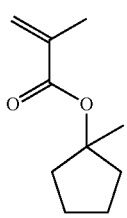
(M-4) 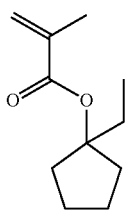
(M-5) 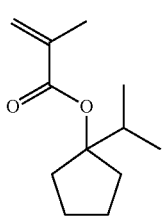
(M-6) 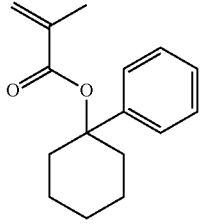
-continued
(M-7) 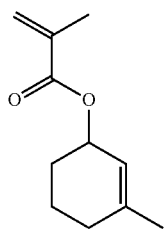
(M-8) 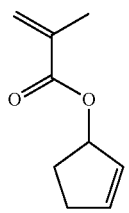
(M-9) 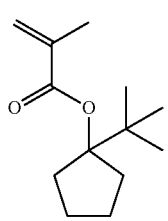
(M-10) 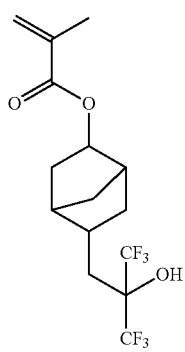
(M-11) 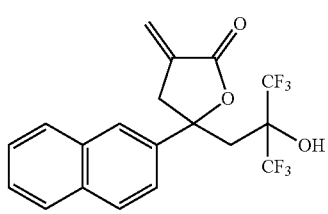
Synthesis Example 1: Synthesis of Polymer (A-1)
The monomer (M-1) and the monomer (M-3) were dissolved in 1-methoxy-2-propanol (200 parts by mass) such that the molar ratio became 40/60. Next, a monomer solution was prepared by adding 6 mol % azobisisobutyronitrile as an initiator. Meanwhile, to an empty reaction vessel were charged 100 parts by mass of 1-methoxy-2-propanol, which were then heated to 85° C. with stirring. Next, the monomer solution prepared as described above was added dropwise over 3 hrs, and a thus resulting solution was further heated for 3 hrs at 85° C., whereby a polymerization reaction was allowed for 6 hrs in total. After completion of the polymerization reaction, the polymerization solution was cooled to room temperature.

The polymerization solution thus cooled was charged into 500 parts by mass of hexane with respect to the polymerization solution, and a thus precipitated white powder was filtered off. The white powder obtained by the filtration was washed twice with 100 parts by mass of hexane with respect to the polymerization solution, followed by filtering off and dissolution in 300 parts by mass of 1-methoxy-2-propanol. Next, 500 parts by mass of methanol, 50 parts by mass of triethylamine, and 10 parts by mass of ultra-pure water were added to a resulting solution, and a hydrolysis reaction was performed at 70° C. for 6 hrs with stirring. After completion of the hydrolysis reaction, the remaining solvent was distilled away and the solid thus obtained was dissolved in 100 parts by mass of acetone. The solution was added dropwise to 500 parts by mass of water to permit coagulation of the resin, a solid thus obtained was filtered off, and drying at 50° C. for 12 hrs gave a white powdery polymer (A-1).

The Mw of the polymer (A-1) was 5,700, and the Mw/Mn was 1.61. Furthermore, as a result of the $^{13}$C-NMR analysis, the proportions of the structural units derived from the monomer (M-1) and the monomer (M-3) in the polymer (A-1) were 41.2 mol % and 58.8 mol %, respectively.

Synthesis Examples 2 to 9: Synthesis of Polymer (A-2) to Polymer (A-9)

Polymers (A-2) to (A-9) were synthesized by a similar operation to that of Synthesis Example 1 except that each monomer of the type and in the proportion shown in Table 1 below was used.

Synthesis of Acid Generating Agent (B)

Synthesis Example 10: Synthesis of Acid Generating Agent (B-1)

Into a reaction vessel were charged 40.3 mmol of bis(4-fluorophenyl)sulfoxide and 290 g of tetrahydrofuran. After stirring a resultant mixture at 0° C., 121 mmol of chlorotrimethylsilane was added thereto by dropwise addition, followed by dropwise addition of 121 mmol of 4-fluorophenylmagnesium bromide. After stirring a resultant mixture for 1 hour at room temperature, an aqueous 2 M solution of hydrochloric acid was added, and then an aqueous layer was separated. The aqueous layer thus obtained was washed with diethyl ether, and an organic layer was extracted with dichloromethane. After drying over sodium sulfate, the solvent was distilled away, and then, by purifying by column chromatography, a compound (hereinafter, may be also referred to as "bromide salt (S-1)") represented by the following formula (S-1) was obtained.

Into a reaction vessel were charged 20.0 mmol of the bromide salt (S-1) obtained as described above, 20.0 mmol of an ammonium salt represented by the following formula (P-1), 150 g of dichloromethane, and 150 g of ultra pure water. After stirring a resultant mixture for 2 hrs at room temperature, an organic layer was separated. The organic layer thus obtained was washed with ultra pure water. After drying over sodium sulfate, the solvent was distilled away, and then, by purifying by column chromatography, a compound (hereinafter, may be also referred to as "acid generating agent (B-1)") represented by the following formula (B-1) was obtained.

A synthesis scheme of the acid generating agent (B-1) is shown below.

TABLE 1

|  | Polymer | Monomer that gives structural unit (I) | | Monomer that gives structural unit (II) | | Monomer that gives structural unit (III) | | Mw | Mw/Mn |
|---|---|---|---|---|---|---|---|---|---|
|  |  | type | amount used (mol %) | proportion of structural unit (mol %) | Type | amount used (mol %) | proportion of structural unit (mol %) | type | amount used (mol %) | proportion of structural unit (mol %) | Mw | Mw/Mn |

| | Polymer | type | amount used (mol %) | proportion of structural unit (mol %) | Type | amount used (mol %) | proportion of structural unit (mol %) | type | amount used (mol %) | proportion of structural unit (mol %) | Mw | Mw/Mn |
|---|---|---|---|---|---|---|---|---|---|---|---|---|---|
| Synthesis | A-1 | M-1$^a$ | 40 | 41.2 | M-3 | 60 | 58.8 | — | — | — | 5,700 | 1.61 |
| Examples | A-2 | M-1$^a$ | 40 | 42.3 | M-4 | 60 | 57.7 | — | — | — | 5,800 | 1.64 |
| | A-3 | M-1$^a$ | 30 | 33.1 | M-5 | 60 | 56.8 | — | — | — | 6,100 | 1.65 |
| | | M-2$^a$ | 10 | 10.1 | | | | | | | | |
| | A-4 | M-1$^a$ | 40 | 41.9 | M-6 | 60 | 58.1 | — | — | — | 6,200 | 1.50 |
| | A-5 | M-1$^a$ | 40 | 39.9 | M-7 | 60 | 60.1 | — | — | — | 5,500 | 1.54 |
| | A-6 | M-1$^a$ | 40 | 40.1 | M-8 | 60 | 59.9 | — | — | — | 5,400 | 1.53 |
| | A-7 | M-1$^a$ | 40 | 43.2 | M-9 | 60 | 56.8 | — | — | — | 6,000 | 1.67 |
| | A-8 | M-1$^a$ | 30 | 30.4 | M-3 | 60 | 58.2 | M-10 | 10 | 11.4 | 6,900 | 1.70 |
| | A-9 | M-1$^a$ | 30 | 30.2 | M-3 | 60 | 59.1 | M-11 | 10 | 10.7 | 6,800 | 1.65 |

$^a$present as a hydroxystyrene unit

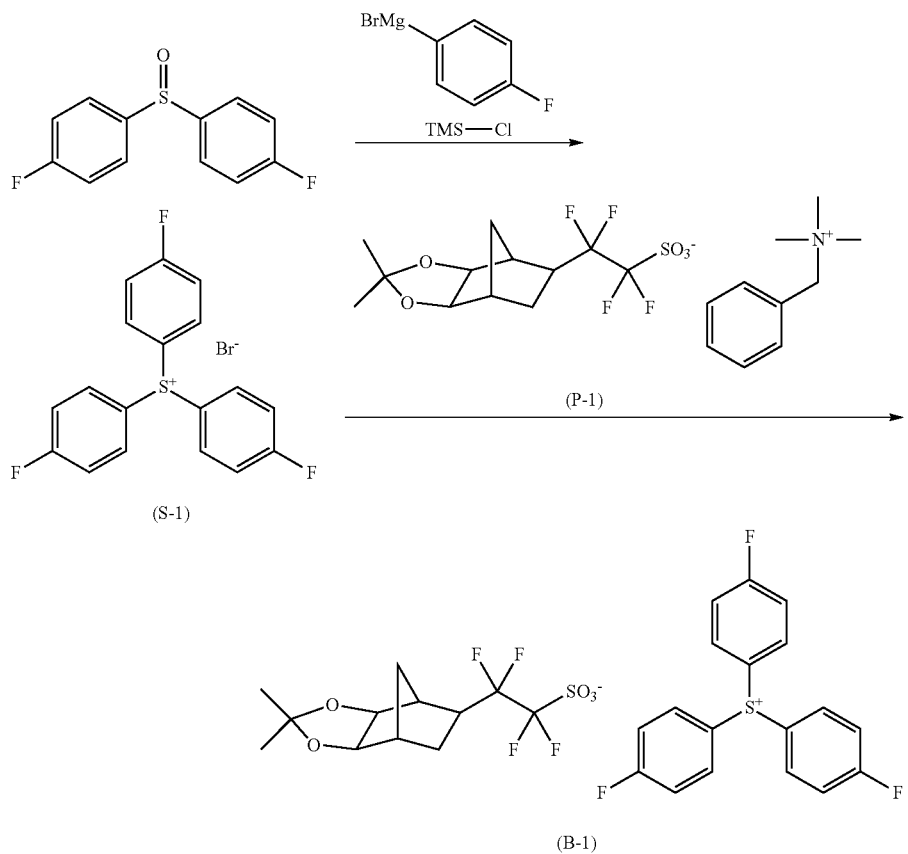
Synthesis Examples 11-34: Synthesis of Acid Generating Agents (B-2) to (B-25)
Compounds (hereinafter, may be also referred to as "acid generating agents (B-2) to (B-25)") represented by the following formulae (B-2) to (B-25) were synthesized by a similar operation to that of Synthesis Example 10 except that each precursor was selected as appropriate.
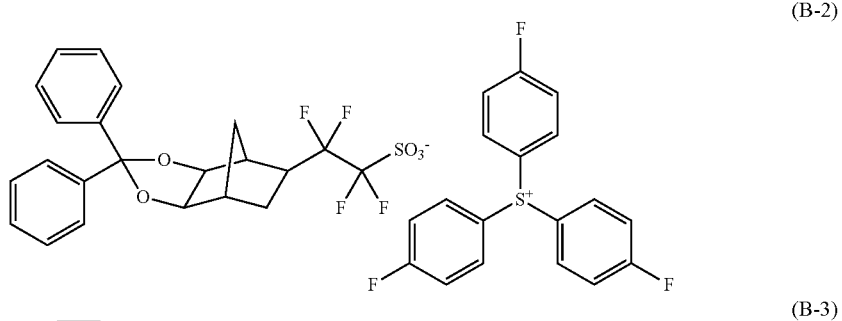
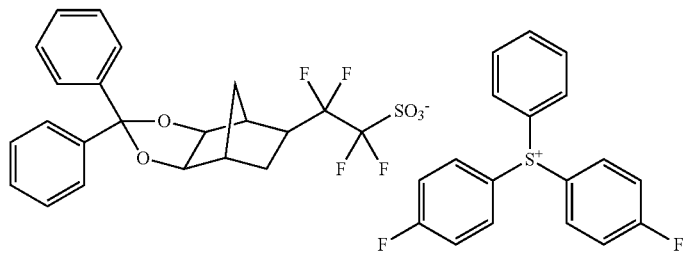

-continued
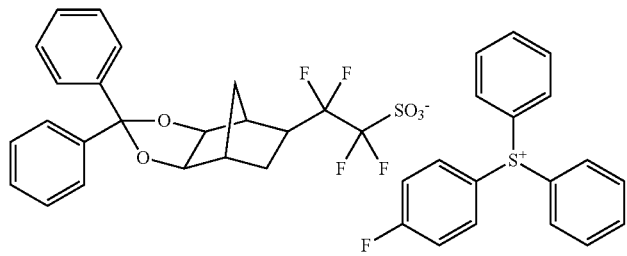
(B-4)
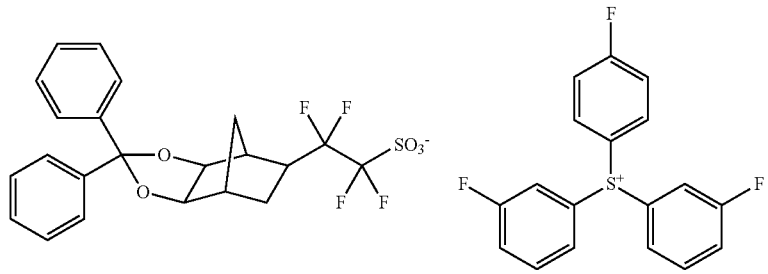
(B-5)
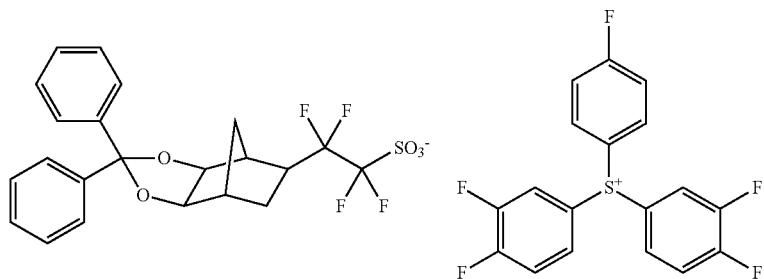
(B-6)
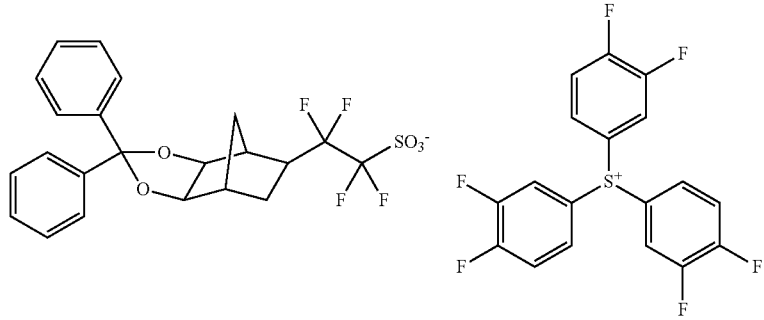
(B-7)
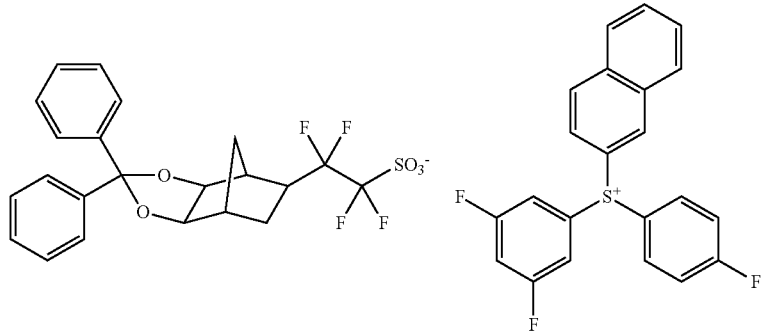
(B-8)

-continued
(B-9)
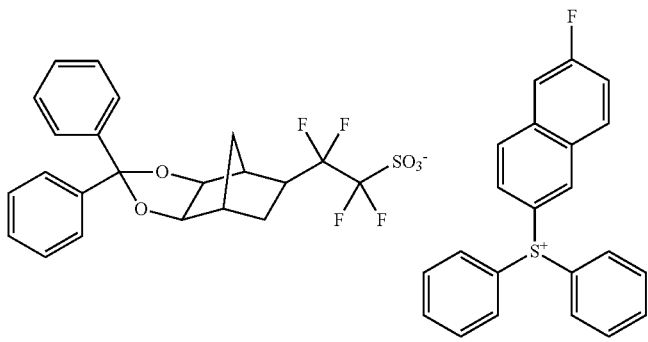
(B-10)
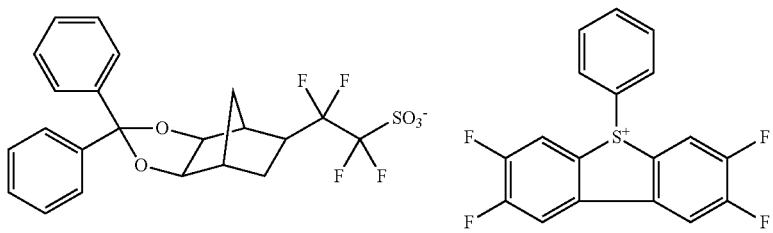
(B-11)
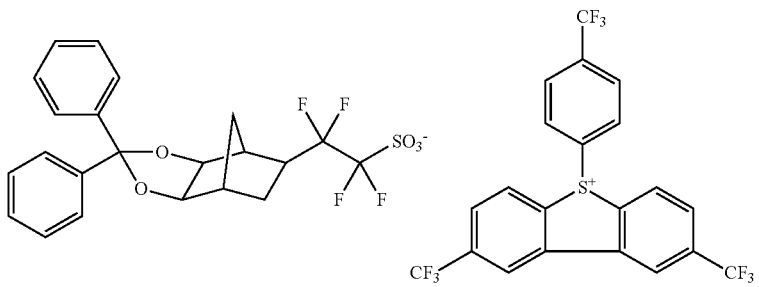
(B-12)
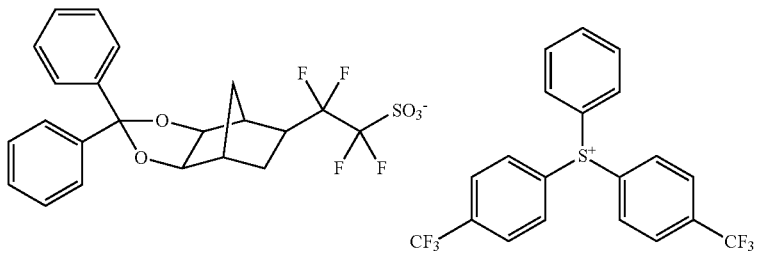
(B-13)
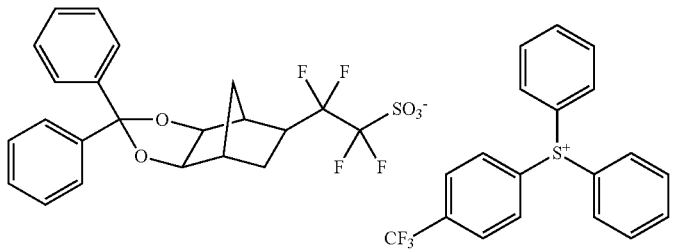

-continued
(B-14)
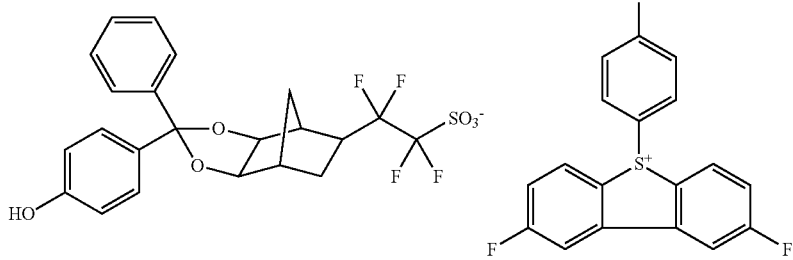
(B-15)
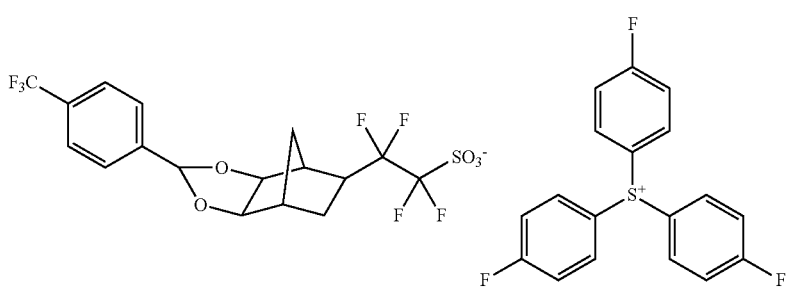
(B-16)
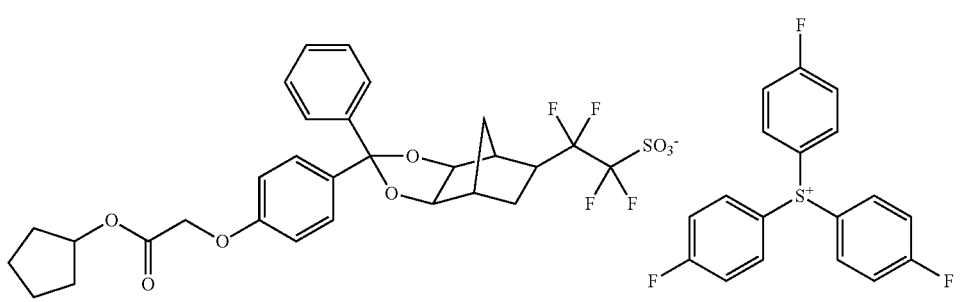
(B-17)
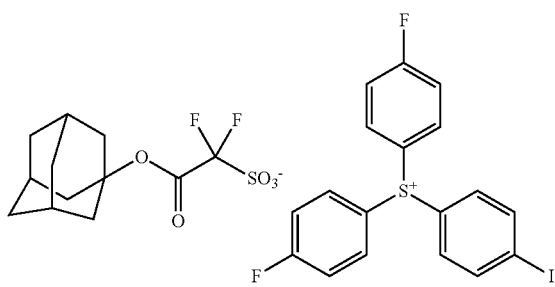
(B-18)
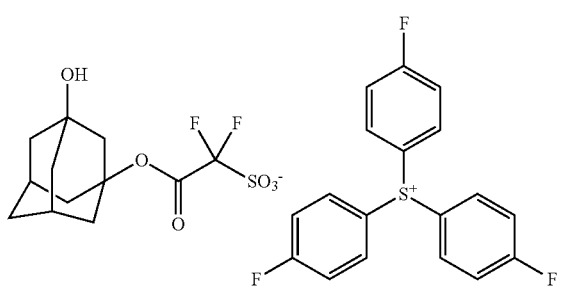

-continued
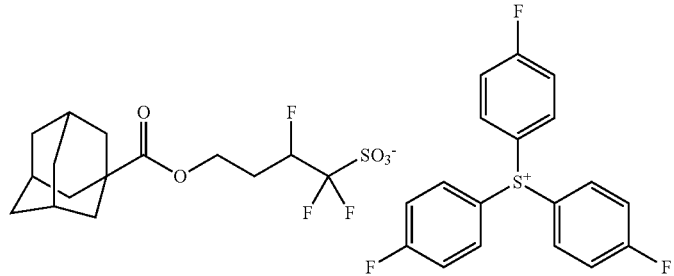
(B-19)
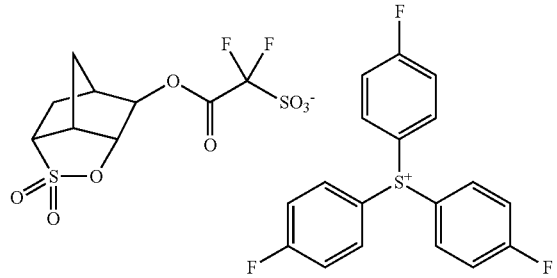
(B-20)
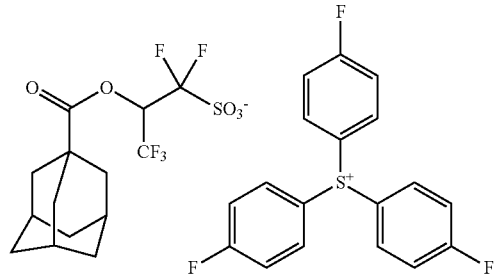
(B-21)
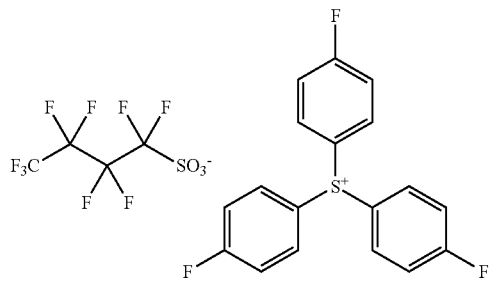
(B-22)
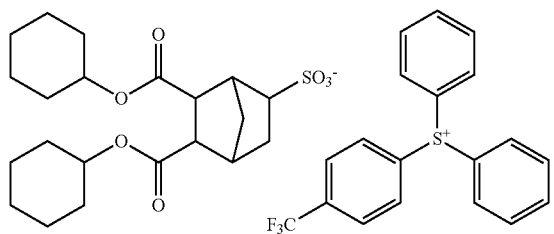
(B-23)

-continued (B-24)

(B-25)

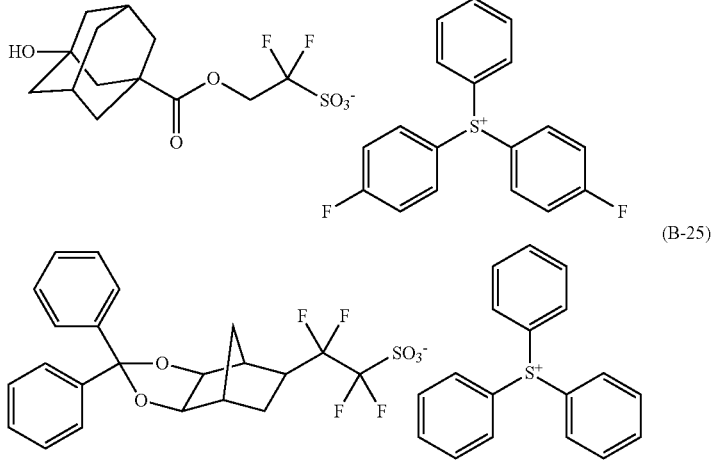

Preparation of Radiation-Sensitive Resin Composition

The acid diffusion control agent (C) and the organic solvent (D) used in preparing each radiation-sensitive resin composition are shown below. It is to be noted that in the following Examples and Comparative Examples, unless otherwise specified particularly, "parts by mass" means a value, provided that the mass of the polymer (A) used was 100 parts by mass, and "mol %" means a value, provided that the mol number of the acid generating agent (B) used was 100 mol %.

(C) Acid Diffusion Control Agent (C-1) To (C-10): Compounds Represented by Following Formulae (C-1) to (C-10)

(C-1)

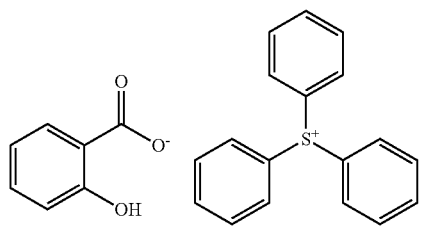

(C-2)

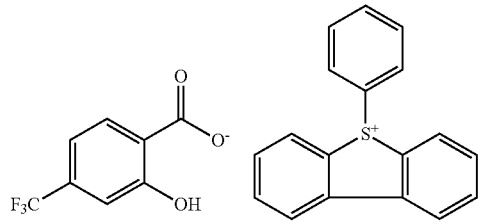

(C-3)

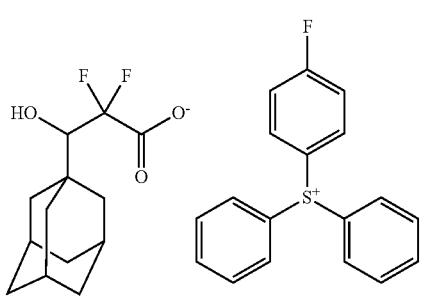

(C-4)

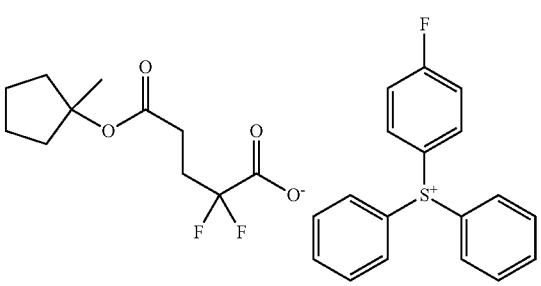

(C-5)

-continued

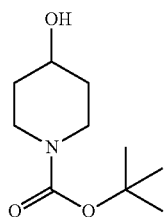
(C-6)

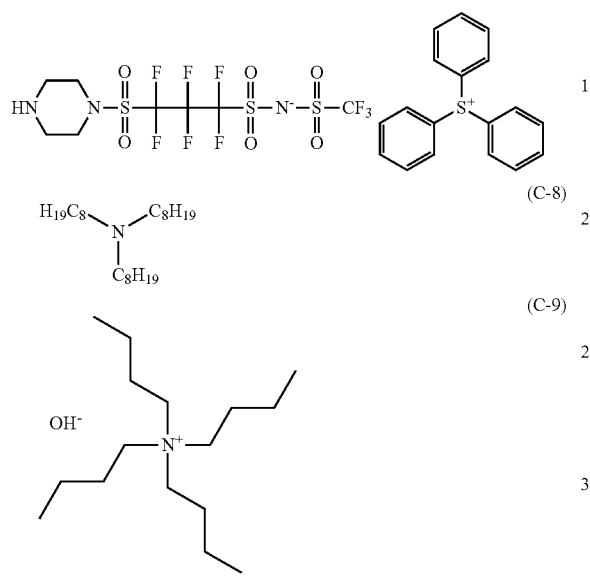
(C-7)

(C-8)

(C-9)

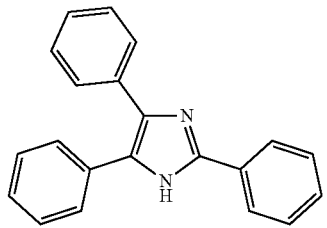
(C-10)

(D) Organic Solvent (D-1): propylene glycol monomethyl ether acetate (D-2): propylene glycol-1-monomethyl ether Example 1: Preparation of Radiation-Sensitive Resin Composition (R-1)

A radiation-sensitive resin composition (R-1) was prepared by: blending 100 parts by mass of (A-1) as the polymer (A), 20 parts by mass of (B-1) as the acid generating agent (B), 20 mol % of (C-1) as the acid diffusion control agent (C) with respect to 100 mol % (B-1), and 4,800 parts by mass of (D-1) and 2,000 parts by mass of (D-2) as the organic solvent (D).

Examples 2 to 39 and Comparative Examples 1 to 15: Preparation of Radiation-Sensitive Resin Compositions (R-2) to (R-39) and (CR-1) to (CR-15) Radiation-sensitive resin compositions (R-2) to (R-39) and (CR-1) to (CR-15) were prepared in a similar manner to Example 1, except that each component of the type and in the content shown in Table 2 below was used.

TABLE 2

| | Radiation-sensitive resin composition | (A) Polymer type | content (parts by mass) | (B) Acid generating agent type | content (parts by mass) | (C) Acid diffusion control agent type | proportion (mol %) | (D) Solvent solvent | parts by mass |
|---|---|---|---|---|---|---|---|---|---|
| Example 1 | R-1 | A-1 | 100 | B-1 | 20 | C-1 | 20 | D-1/D-2 | 4,800/2,000 |
| Example 2 | R-2 | A-1 | 100 | B-2 | 20 | C-1 | 20 | D-1/D-2 | 4,800/2,000 |
| Example 3 | R-3 | A-1 | 100 | B-3 | 20 | C-1 | 20 | D-1/D-2 | 4,800/2,000 |
| Example 4 | R-4 | A-1 | 100 | B-4 | 20 | C-1 | 20 | D-1/D-2 | 4,800/2,000 |
| Example 5 | R-5 | A-1 | 100 | B-5 | 20 | C-1 | 20 | D-1/D-2 | 4,800/2,000 |
| Example 6 | R-6 | A-1 | 100 | B-6 | 20 | C-1 | 20 | D-1/D-2 | 4,800/2,000 |
| Example 7 | R-7 | A-1 | 100 | B-7 | 20 | C-1 | 20 | D-1/D-2 | 4,800/2,000 |
| Example 8 | R-8 | A-1 | 100 | B-8 | 20 | C-1 | 20 | D-1/D-2 | 4,800/2,000 |
| Example 9 | R-9 | A-1 | 100 | B-9 | 20 | C-1 | 20 | D-1/D-2 | 4,800/2,000 |
| Example 10 | R-10 | A-1 | 100 | B-10 | 20 | C-1 | 20 | D-1/D-2 | 4,800/2,000 |
| Example 11 | R-11 | A-1 | 100 | B-11 | 20 | C-1 | 20 | D-1/D-2 | 4,800/2,000 |
| Example 12 | R-12 | A-1 | 100 | B-12 | 20 | C-1 | 20 | D-1/D-2 | 4,800/2,000 |
| Example 13 | R-13 | A-1 | 100 | B-13 | 20 | C-1 | 20 | D-1/D-2 | 4,800/2,000 |
| Example 14 | R-14 | A-1 | 100 | B-14 | 20 | C-1 | 20 | D-1/D-2 | 4,800/2,000 |
| Example 15 | R-15 | A-1 | 100 | B-15 | 20 | C-1 | 20 | D-1/D-2 | 4,800/2,000 |
| Example 16 | R-16 | A-1 | 100 | B-16 | 20 | C-1 | 20 | D-1/D-2 | 4,800/2,000 |
| Example 17 | R-17 | A-1 | 100 | B-17 | 20 | C-1 | 20 | D-1/D-2 | 4,800/2,000 |
| Example 18 | R-18 | A-1 | 100 | B-18 | 20 | C-1 | 20 | D-1/D-2 | 4,800/2,000 |
| Example 19 | R-19 | A-1 | 100 | B-19 | 20 | C-1 | 20 | D-1/D-2 | 4,800/2,000 |
| Example 20 | R-20 | A-1 | 100 | B-20 | 20 | C-1 | 20 | D-1/D-2 | 4,800/2,000 |
| Example 21 | R-21 | A-1 | 100 | B-21 | 20 | C-1 | 20 | D-1/D-2 | 4,800/2,000 |
| Example 22 | R-22 | A-1 | 100 | B-22 | 20 | C-1 | 20 | D-1/D-2 | 4,800/2,000 |
| Example 23 | R-23 | A-1 | 100 | B-23 | 20 | C-1 | 20 | D-1/D-2 | 4,800/2,000 |
| Example 24 | R-24 | A-1 | 100 | B-24 | 20 | C-1 | 20 | D-1/D-2 | 4,800/2,000 |
| Example 25 | R-25 | A-1 | 100 | B-2 | 40 | C-1 | 20 | D-1/D-2 | 4,800/2,000 |
| Example 26 | R-26 | A-1 | 100 | B-2 | 30 | C-1 | 20 | D-1/D-2 | 4,800/2,000 |
| Example 27 | R-27 | A-1 | 100 | B-2 | 15 | C-1 | 20 | D-1/D-2 | 4,800/2,000 |
| Example 28 | R-28 | A-1 | 100 | B-2 | 20 | C-2 | 20 | D-1/D-2 | 4,800/2,000 |
| Example 29 | R-29 | A-1 | 100 | B-2 | 20 | C-3 | 20 | D-1/D-2 | 4,800/2,000 |
| Example 30 | R-30 | A-1 | 100 | B-2 | 20 | C-4 | 20 | D-1/D-2 | 4,800/2,000 |

TABLE 2-continued

| | Radiation-sensitive resin composition | (A) Polymer type | content (parts by mass) | (B) Acid generating agent type | content (parts by mass) | (C) Acid diffusion control agent type | proportion (mol %) | (D) Solvent solvent | parts by mass |
|---|---|---|---|---|---|---|---|---|---|
| Example 31 | R-31 | A-1 | 100 | B-2 | 20 | C-5 | 20 | D-1/D-2 | 4,800/2,000 |
| Example 32 | R-32 | A-2 | 100 | B-2 | 20 | C-1 | 20 | D-1/D-2 | 4,800/2,000 |
| Example 33 | R-33 | A-3 | 100 | B-2 | 20 | C-1 | 20 | D-1/D-2 | 4,800/2,000 |
| Example 34 | R-34 | A-4 | 100 | B-2 | 20 | C-1 | 20 | D-1/D-2 | 4,800/2,000 |
| Example 35 | R-35 | A-5 | 100 | B-2 | 20 | C-1 | 20 | D-1/D-2 | 4,800/2,000 |
| Example 36 | R-36 | A-6 | 100 | B-2 | 20 | C-1 | 20 | D-1/D-2 | 4,800/2,000 |
| Example 37 | R-37 | A-7 | 100 | B-2 | 20 | C-1 | 20 | D-1/D-2 | 4,800/2,000 |
| Example 38 | R-38 | A-8 | 100 | B-2 | 20 | C-1 | 20 | D-1/D-2 | 4,800/2,000 |
| Example 39 | R-39 | A-9 | 100 | B-2 | 20 | C-1 | 20 | D-1/D-2 | 4,800/2,000 |
| Comparative Example 1 | CR-1 | A-1 | 100 | B-25 | 20 | C-6 | 20 | D-1/D-2 | 4,800/2,000 |
| Comparative Example 2 | CR-2 | A-1 | 100 | B-25 | 20 | C-7 | 20 | D-1/D-2 | 4,800/2,000 |
| Comparative Example 3 | CR-3 | A-1 | 100 | B-25 | 20 | C-8 | 20 | D-1/D-2 | 4,800/2,000 |
| Comparative Example 4 | CR-4 | A-1 | 100 | B-25 | 20 | C-9 | 20 | D-1/D-2 | 4,800/2,000 |
| Comparative Example 5 | CR-5 | A-1 | 100 | B-25 | 20 | C-10 | 20 | D-1/D-2 | 4,800/2,000 |
| Comparative Example 6 | CR-6 | A-1 | 100 | B-25 | 20 | C-1 | 20 | D-1/D-2 | 4,800/2,000 |
| Comparative Example 7 | CR-7 | A-1 | 100 | B-25 | 20 | C-2 | 20 | D-1/D-2 | 4,800/2,000 |
| Comparative Example 8 | CR-8 | A-1 | 100 | B-25 | 20 | C-3 | 20 | D-1/D-2 | 4,800/2,000 |
| Comparative Example 9 | CR-9 | A-1 | 100 | B-25 | 20 | C-4 | 20 | D-1/D-2 | 4,800/2,000 |
| Comparative Example 10 | CR-10 | A-1 | 100 | B-25 | 20 | C-5 | 20 | D-1/D-2 | 4,800/2,000 |
| Comparative Example 11 | CR-11 | A-1 | 100 | B-1 | 20 | C-6 | 20 | D-1/D-2 | 4,800/2,000 |
| Comparative Example 12 | CR-12 | A-1 | 100 | B-1 | 20 | C-7 | 20 | D-1/D-2 | 4,800/2,000 |
| Comparative Example 13 | CR-13 | A-1 | 100 | B-1 | 20 | C-8 | 20 | D-1/D-2 | 4,800/2,000 |
| Comparative Example 14 | CR-14 | A-1 | 100 | B-1 | 20 | C-9 | 20 | D-1/D-2 | 4,800/2,000 |
| Comparative Example 15 | CR-15 | A-1 | 100 | B-1 | 20 | C-10 | 20 | D-1/D-2 | 4,800/2,000 |

Resist Pattern Formation

Using a spin coater ("CLEAN TRACK ACT12," available from Tokyo Electron Limited), the radiation-sensitive resin compositions prepared as described above were each applied on a surface of a 12-inch silicon wafer with an underlayer film ("AL412," available from Brewer Science, Inc.) having an average thickness of 20 nm being provided thereon, and soft baking (SB) was conducted at 130° C. for 60 sec. Thereafter, by cooling at 23° C. for 30 sec, a resist film having an average thickness of 50 nm was formed. Next, the resist film was irradiated with EUV using an EUV scanner (model "NXE3300," available from ASML Co., with NA of 0.33 under an illumination condition of Conventional s=0.89, and with a mask of imecDEFECT32FFR02). After the irradiation, the resist film was subjected to post-exposure baking (PEB) at 130° C. for 60 sec. Thereafter, the resist film was developed at 23° C. for 30 sec by using a 2.38% by mass aqueous TMAH solution to form a positive-tone resist pattern (32 nm line-and-space pattern).

Evaluations

With regard to the resist patterns formed as described above, each radiation-sensitive resin composition was evaluated on the sensitivity, the LWR performance, and the resolution thereof in accordance with the following method. It is to be noted that a scanning electron microscope ("CG-4100," available from Hitachi High-Technologies Corporation) was used for line-width measurement of the resist patterns. The results of the evaluations are shown in Table 3 below.

Sensitivity

An exposure dose at which a 32 nm line-and-space pattern was formed in the aforementioned resist pattern formation was defined as an optimum exposure dose, and this optimum exposure dose was adopted as Eop (unit: mJ/cm$^2$). The sensitivity was evaluated to be: "favorable" in a case of the Eop being no greater than 30 mJ/cm$^2$; and "unfavorable" in a case of the Eop being greater than 30 mJ/cm$^2$.

LWR Performance

The resist patterns were observed from above using the scanning electron microscope. Line widths were measured at 50 arbitrary sites, and then a 3 Sigma value was determined from distribution of the measurements and defined as "LWR" (unit: nm). The value being smaller reveals less line rattling, indicating better LWR performance. The LWR performance was evaluated to be: "favorable" in a case of the LWR being no greater than 4.0 nm; and "unfavorable" in a case of the LWR being greater than 4.0 nm.

Resolution

A dimension of a minimum resist pattern being resolved at the optimum exposure dose was measured when the mask pattern size for forming the line-and-space (1L/1S) was changed, and the measurement value was defined as "resolution" (unit: nm). The value being smaller enables formation of a finer pattern, indicating a more favorable resolution. The resolution was evaluated to be: "favorable" in a case of the resolution being no greater than 25 nm; and "unfavorable" in a case of the resolution being greater than 25 nm.

TABLE 3

| | Radiation-sensitive resin composition | Eop (mJ/cm$^2$) | LWR (nm) | Resolution (nm) |
|---|---|---|---|---|
| Example 1 | R-1 | 25 | 3.7 | 24 |
| Example 2 | R-2 | 26 | 3.5 | 22 |
| Example 3 | R-3 | 27 | 3.6 | 23 |
| Example 4 | R-4 | 28 | 3.7 | 24 |
| Example 5 | R-5 | 26 | 3.5 | 23 |
| Example 6 | R-6 | 26 | 3.5 | 22 |
| Example 7 | R-7 | 26 | 3.5 | 23 |
| Example 8 | R-8 | 27 | 3.5 | 23 |
| Example 9 | R-9 | 28 | 3.5 | 23 |
| Example 10 | R-10 | 27 | 3.4 | 22 |
| Example 11 | R-11 | 25 | 3.4 | 23 |
| Example 12 | R-12 | 25 | 3.4 | 22 |
| Example 13 | R-13 | 26 | 3.5 | 22 |
| Example 14 | R-14 | 27 | 3.5 | 22 |
| Example 15 | R-15 | 25 | 3.4 | 23 |
| Example 16 | R-16 | 25 | 3.4 | 21 |
| Example 17 | R-17 | 27 | 3.7 | 23 |
| Example 18 | R-18 | 28 | 3.8 | 24 |
| Example 19 | R-19 | 27 | 3.7 | 23 |
| Example 20 | R-20 | 27 | 3.6 | 23 |
| Example 21 | R-21 | 28 | 3.7 | 23 |
| Example 22 | R-22 | 27 | 3.9 | 24 |
| Example 23 | R-23 | 29 | 3.9 | 24 |
| Example 24 | R-24 | 27 | 3.7 | 23 |
| Example 25 | R-25 | 25 | 3.3 | 22 |
| Example 26 | R-26 | 26 | 3.4 | 22 |
| Example 27 | R-27 | 28 | 3.8 | 24 |
| Example 28 | R-28 | 25 | 3.6 | 22 |
| Example 29 | R-29 | 26 | 3.7 | 23 |
| Example 30 | R-30 | 24 | 3.5 | 23 |
| Example 31 | R-31 | 27 | 3.5 | 23 |
| Example 32 | R-32 | 27 | 3.4 | 22 |
| Example 33 | R-33 | 27 | 3.5 | 22 |
| Example 34 | R-34 | 28 | 3.7 | 23 |
| Example 35 | R-35 | 28 | 3.6 | 23 |
| Example 36 | R-36 | 28 | 3.7 | 23 |
| Example 37 | R-37 | 28 | 3.8 | 24 |
| Example 38 | R-38 | 25 | 3.4 | 21 |
| Example 39 | R-39 | 26 | 3.4 | 22 |
| Comparative Example 1 | CR-1 | 34 | 4.2 | 28 |
| Comparative Example 2 | CR-2 | 32 | 3.9 | 27 |
| Comparative Example 3 | CR-3 | 35 | 4.3 | 29 |
| Comparative Example 4 | CR-4 | 35 | 4.4 | 28 |
| Comparative Example 5 | CR-5 | 34 | 4.2 | 29 |
| Comparative Example 6 | CR-6 | 31 | 3.8 | 27 |
| Comparative Example 7 | CR-7 | 30 | 3.9 | 26 |
| Comparative Example 8 | CR-8 | 32 | 4.1 | 25 |
| Comparative Example 9 | CR-9 | 32 | 3.9 | 26 |
| Comparative Example 10 | CR-10 | 31 | 4.0 | 28 |

TABLE 3-continued

| | Radiation-sensitive resin composition | Eop (mJ/cm$^2$) | LWR (nm) | Resolution (nm) |
|---|---|---|---|---|
| Comparative Example 11 | CR-11 | 33 | 4.3 | 28 |
| Comparative Example 12 | CR-12 | 32 | 4.3 | 27 |
| Comparative Example 13 | CR-13 | 29 | 4.2 | 29 |
| Comparative Example 14 | CR-14 | 31 | 4.1 | 26 |
| Comparative Example 15 | CR-15 | 33 | 4.5 | 28 |

As is clear from the results shown in Table 3, for all of the radiation-sensitive resin compositions of the Examples, the sensitivity, the LWR performance, and the resolution were favorable when compared to the radiation-sensitive resin compositions of the Comparative Examples.

Example 40: Preparation of Radiation-Sensitive Resin Composition (R-40)

A radiation-sensitive resin composition (R-40) was prepared in a similar manner to Example 1, except that a compound (acid generating agent (B-26)) represented by the following formula was used in place of the acid generating agent (B-1). Next, a resist pattern was formed in a similar manner to that described above, and the sensitivity, the LWR performance, and the resolution were evaluated. As a result, the sensitivity, the LWR performance, and the resolution of the radiation-sensitive resin composition (R-40) were favorable when compared to the radiation-sensitive resin compositions of the Comparative Examples.

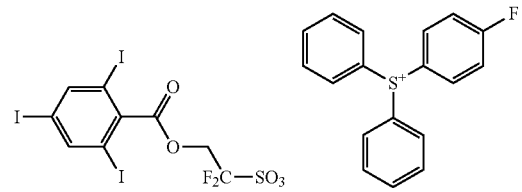

Example 41: Preparation of Radiation-Sensitive Resin Composition (R-41)

A radiation-sensitive resin composition (R-41) was prepared in a similar manner to Example 1, except that a compound (acid generating agent (B-27)) represented by the following formula was used in place of the acid generating agent (B-1). Next, a resist pattern was formed in a similar manner to that described above, and the sensitivity, the LWR performance, and the resolution were evaluated. As a result, the sensitivity, the LWR performance, and the resolution of the radiation-sensitive resin composition (R-41) were favorable when compared to the radiation-sensitive resin compositions of the Comparative Examples.

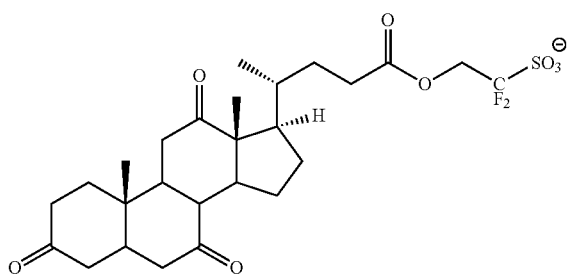
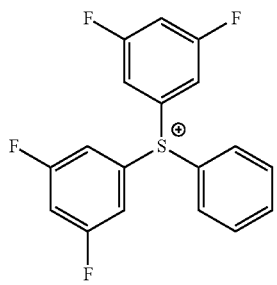

Example 42: Preparation of Radiation-Sensitive Resin Composition (R-42)

A radiation-sensitive resin composition (R-42) was prepared in a similar manner to Example 1, except that a compound (acid generating agent (B-28)) represented by the following formula was used in place of the acid generating agent (B-1). Next, a resist pattern was formed in a similar manner to that described above, and the sensitivity, the LWR performance, and the resolution were evaluated. As a result, the sensitivity, the LWR performance, and the resolution of the radiation-sensitive resin composition (R-42) were favorable when compared to the radiation-sensitive resin compositions of the Comparative Examples.

Example 44: Preparation of Radiation-Sensitive Resin Composition (R-44)

A polymer (A-11) was synthesized in a similar manner to Synthesis Example 4, except that a monomer (monomer (M-13)) represented by the following formula was used in place of the monomer (M-4). Next, a radiation-sensitive resin composition (R-44) was prepared in a similar manner to Example 32, except that the polymer (A-11) was used in place of the polymer (A-2); thereafter, a resist pattern was formed in a similar manner to that described above, and the sensitivity, the LWR performance, and the resolution were evaluated. As a result, the sensitivity, the LWR performance, and the resolution of the radiation-sensitive resin composition (R-44) were favorable when compared to the radiation-sensitive resin compositions of the Comparative Examples.

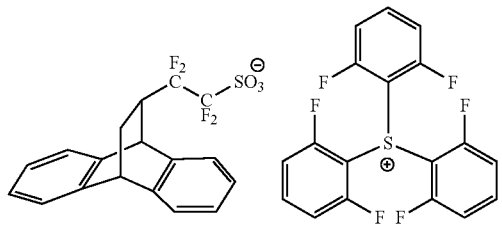
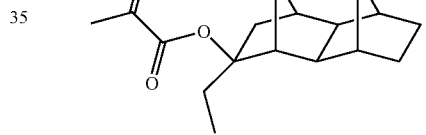

Example 43: Preparation of Radiation-Sensitive Resin Composition (R-43)

A polymer (A-10) was synthesized in a similar manner to Synthesis Example 4, except that a monomer (monomer (M-12)) represented by the following formula was used in place of the monomer (M-6). Next, a radiation-sensitive resin composition (R-43) was prepared in a similar manner to Example 34, except that the polymer (A-10) was used in place of the polymer (A-4); thereafter, a resist pattern was formed in a similar manner to that described above, and the sensitivity, the LWR performance, and the resolution were evaluated. As a result, the sensitivity, the LWR performance, and the resolution of the radiation-sensitive resin composition (R-43) were favorable when compared to the radiation-sensitive resin compositions of the Comparative Examples.

Example 45: Preparation of Radiation-Sensitive Resin Composition (R-45)

A polymer (A-12) was synthesized in a similar manner to Synthesis Example 4, except that a monomer (monomer (M-14)) represented by the following formula was used in place of the monomer (M-6). Next, a radiation-sensitive resin composition (R-45) was prepared in a similar manner to Example 34, except that the polymer (A-12) was used in place of the polymer (A-4); thereafter, a resist pattern was formed in a similar manner to that described above, and the sensitivity, the LWR performance, and the resolution were evaluated. As a result, the sensitivity, the LWR performance, and the resolution of the radiation-sensitive resin composition (R-45) were favorable when compared to the radiation-sensitive resin compositions of the Comparative Examples.

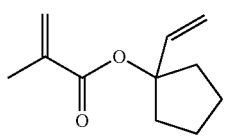
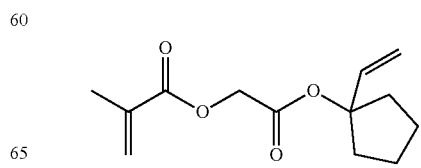

Example 46: Preparation of Radiation-Sensitive Resin Composition (R-46)

A polymer (A-13) was synthesized in a similar manner to Synthesis Example 1, except that the monomers (M-1) and (M-3), and a monomer (monomer (M-15)) represented by the following formula were used such that the molar ratio became 30/55/15. Next, a radiation-sensitive resin composition (R-46) was prepared in a similar manner to Example 1, except that the polymer (A-13) was used in place of the polymer (A-1); thereafter, a resist pattern was formed in a similar manner to that described above, and the sensitivity, the LWR performance, and the resolution were evaluated. As a result, the sensitivity, the LWR performance, and the resolution of the radiation-sensitive resin composition (R-46) were favorable when compared to the radiation-sensitive resin compositions of the Comparative Examples.

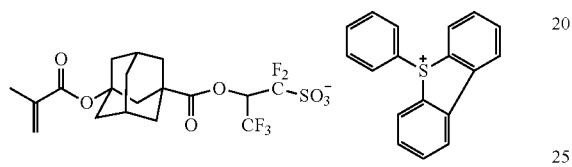

The radiation-sensitive resin composition and the resist pattern-forming method of the embodiments of the present invention enable a resist pattern to be formed with favorable sensitivity to exposure light, and superiority with regard to each of LWR performance and resolution. Therefore, these can be suitably used for formation of fine resist patterns in lithography steps of various types of electronic devices such as semiconductor devices and liquid crystal devices.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising:
   a polymer comprising a first structural unit represented by at least one formula selected from the group consisting of formula (I-1), formula (I-2), formula (I-3), formula (I-4), formula (I-5), formula (I-6), formula (I-7), formula (I-8), formula (I-9), formula (I-10), formula (I-11), formula (I-12), formula (I-13), and formula (I-14) and a second structural unit comprising an acid-labile group which is dissociated by an action of an acid to give a carboxy group;
   a first compound represented by formula (1-1) or formula (1-2); and
   a second compound represented by formula (2):

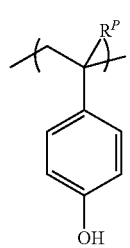 (I-1)

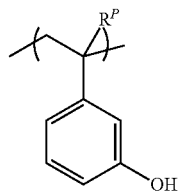 (I-2)

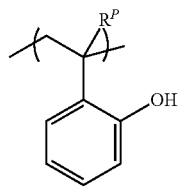 (I-3)

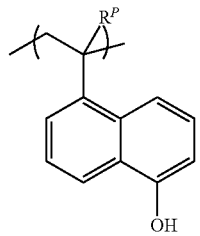 (I-4)

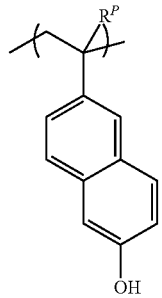 (I-5)

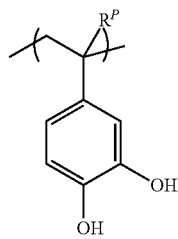 (I-6)

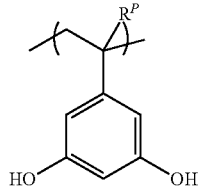 (I-7)

(I-8) 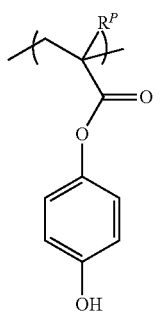

(I-9) 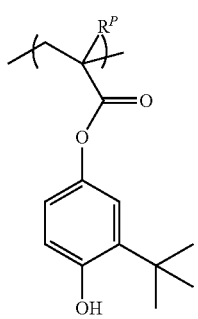

(I-10) 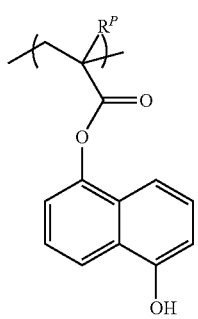

(I-11) 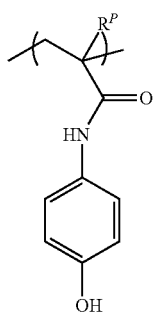

(I-12) 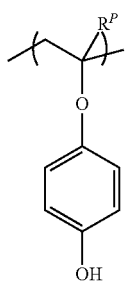

(I-13) 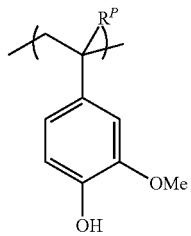

(I-14) 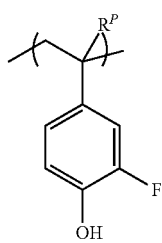

wherein
in each of the formulae (I-1) to (I-14), $R^P$ represents a hydrogen atom, a fluorine atom, a methyl group, or a trifluoromethyl group, (1-1) 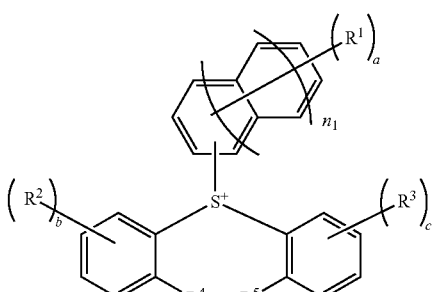

(1-2) 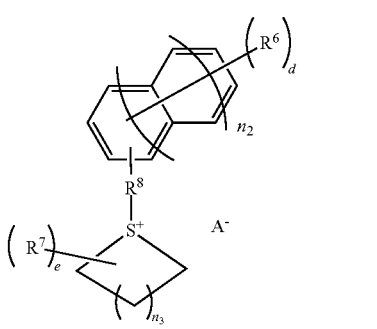

wherein
in each of the formula (1-1) and the formula (1-2), $A^-$ represents a monovalent sulfonic acid anion,
in the formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^1$, $R^2$, and $R^3$ represents a fluorine atom or a monovalent fluorinated hydrocarbon group having 1 to 10 carbon atoms, in a case in which a is no less than 2, a plurality of $R^1$s are identical or different, in a case in which b is no less than 2, a plurality of $R^2$s are identical or different, and in a case in which c is no less than 2, a plurality of $R^3$s are identical or different; ni is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond, in the formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; $n_2$ is 0 or 1; and $n_3$ is an integer of 0 to 3, and $$R^9\text{—COO}^-X^+ \qquad (2)$$

in the formula (2), $R^9$ represents a monovalent organic group having 1 to 30 carbon atoms; and $X^+$ represents a monovalent radiation-sensitive onium cation, and wherein a molar amount of the first structural unit relative to a total molar amount of structural units constituting the polymer is 25 mol % or more, and a molar amount of the second structural unit relative to the total molar amount of the structural units constituting the polymer is 30 mol % or more.

2. The radiation-sensitive resin composition according to claim 1, wherein the monovalent sulfonic acid anion comprises a ring structure.

3. The radiation-sensitive resin composition according to claim 2, wherein the ring structure is at least one selected from a norbornane structure, an adamantane structure, and a sultone structure.

4. The radiation-sensitive resin composition according to claim 2, wherein the ring structure is an aromatic ring structure comprising at least one iodine atom as a substituent.

5. The radiation-sensitive resin composition according to claim 2, wherein the ring structure comprises a steroid skeleton or a 9,10-ethanoanthracene skeleton.

6. The radiation-sensitive resin composition according to claim 1, wherein the monovalent sulfonic acid anion comprises a partial structure represented by formula (3),

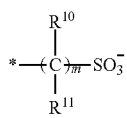

(3)

wherein in the formula (3), $R^{10}$ and $R^{11}$ each independently represent a hydrogen atom, a fluorine atom, a monovalent hydrocarbon group having 1 to 20 carbon atoms, or a monovalent fluorinated hydrocarbon group having 1 to 20 carbon atoms, wherein at least one of $R^{10}$ and $R^{11}$ represents a fluorine atom or a monovalent fluorinated hydrocarbon group having 1 to 20 carbon atoms; m is an integer of 1 to 10, wherein in a case in which m is no less than 2, a plurality of $R^{10}$s are identical or different and a plurality of $R^{11}$s are identical or different; and * denotes a binding site to a part other than the partial structure represented by the formula (3) in the monovalent sulfonic acid anion.

7. The radiation-sensitive resin composition according to claim 6, wherein in the formula (3), $R^{10}$ and $R^{11}$ each independently represent a fluorine atom, a monovalent hydrocarbon group having 1 to 20 carbon atoms, or a monovalent fluorinated hydrocarbon group having 1 to 20 carbon atoms, wherein at least one of $R^{10}$ and $R^{11}$ represents a fluorine atom or a monovalent fluorinated hydrocarbon group having 1 to 20 carbon atoms; m is an integer of 2 to 10, wherein a plurality of $R^{10}$s are identical or different and a plurality of $R^{11}$s are identical or different.

8. The radiation-sensitive resin composition according to claim 1, wherein the second structural unit is represented by formula (4-1), formula (4-2), or formula (4-3),

(4-1)

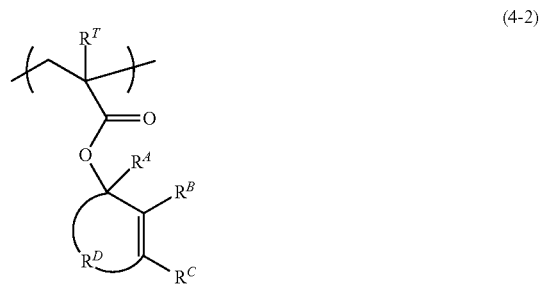

(4-2)

(4-3)

wherein in each of the formulae (4-1) to (4-3), each $R^T$ independently represents a hydrogen atom, a fluorine atom, a methyl group, or a trifluoromethyl group, in the formula (4-1), $R^X$ represents a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent an alicyclic structure having 3 to 20 ring atoms, together with the carbon atom to which $R^Y$ and $R^Z$ bond, in the formula (4-2), $R^A$ represents a hydrogen atom; $R^B$ and $R^C$ each independently represent a hydrogen atom or a monovalent hydrocarbon group having 1 to 20 carbon atoms; and $R^D$ represents a divalent hydrocarbon group having 1 to 20 carbon atoms constituting an unsaturated alicyclic structure having 4 to 20 ring atoms together with the carbon atom to which each of $R^A$, $R^B$, and $R^C$ bonds, and in the formula (4-3), $R^U$ and $R^V$ each independently represent a hydrogen atom or a monovalent hydrocarbon group having 1 to 20 carbon atoms, and $R^W$ represents a monovalent hydrocarbon group having 1 to 20 carbon atoms, and $R^U$ and $R^V$ optionally taken together represent an alicyclic structure having 3 to 20 ring atoms, together with the carbon atom to which $R^U$ and $R^V$ bond, and $R^U$ and $R^W$ optionally taken together represent an alicyclic heterocyclic structure having 5 to 20 ring atoms, together with the carbon atom to which $R^U$ bonds and the oxygen atom to which $R^W$ bonds.

9. The radiation-sensitive resin composition according to claim 8, wherein in the formula (4-1), $R^X$ represents an alkyl group, an ethenyl group, or a phenyl group; and $R^Y$ and $R^Z$ taken together represent an alicyclic structure having 3 to 20 ring atoms, together with the carbon atom to which $R^Y$ and $R^Z$ bond.

10. The radiation-sensitive resin composition according to claim 9, wherein the alicyclic structure represented by $R^Y$ and $R^Z$ comprises a norbornane skeleton.

11. The radiation-sensitive resin composition according to claim 1, wherein in the second structural unit, the acid-labile group is at least five atoms away, in terms of a number of atoms, from a main chain of the polymer.

12. The radiation-sensitive resin composition according to claim 1, wherein the polymer further comprises a structural unit comprising a partial structure represented by formula (5),

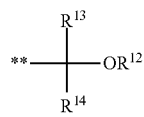
(5)

wherein in the formula (5), $R^{12}$ represents a hydrogen atom or a monovalent organic group having 1 to 20 carbon atoms; $R^{13}$ and $R^{14}$ each independently represent a fluorine atom or a monovalent fluorinated hydrocarbon group having 1 to 10 carbon atoms; and ** denotes a binding site to a part other than the partial structure represented by the formula (5) in the structural unit.

13. The radiation-sensitive resin composition according to claim 1, wherein the polymer further comprises a structural unit comprising a partial structure which generates a sulfonic acid upon exposure.

14. The radiation-sensitive resin composition according to claim 1, wherein the first compound is represented by the formula (1-1), and in the formula (1-1), the sum of a, b, and c is an integer of 2 to 6.

15. A resist pattern-forming method comprising:
applying a radiation-sensitive resin composition directly or indirectly on a substrate to form a resist film;
exposing the resist film; and
developing the resist film exposed, wherein
the radiation-sensitive resin composition comprises:
a polymer comprising a first structural unit represented by at least one formula selected from the group consisting of formula (I-1), formula (I-2), formula (I-3), formula (I-4), formula (I-5), formula (I-6), formula (I-7), formula (I-8), formula (I-9), formula (I-10), formula (I-11), formula (I-12), formula (I-13), and formula (I-14) and a second structural unit comprising an acid-labile group which is dissociated by an action of an acid to give a carboxy group;

a first compound represented by formula (1-1) or formula (1-2); and a second compound represented by formula (2);

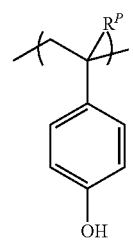
(I-1)

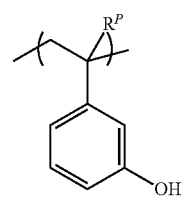
(I-2)

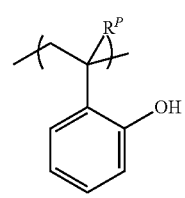
(I-3)

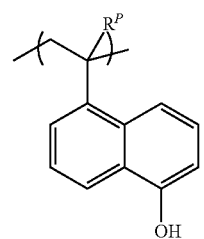
(I-4)

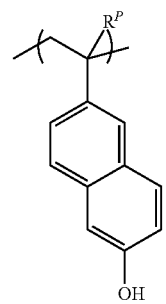
(I-5)

(I-6) 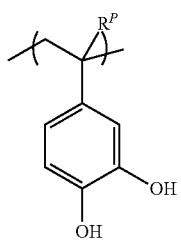
(I-7) 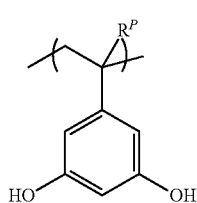
(I-8) 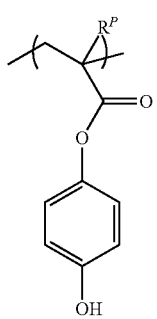
(I-9) 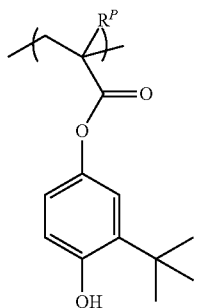
(I-10) 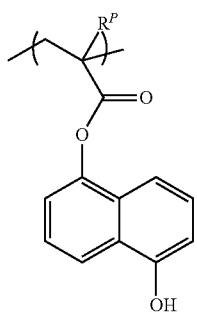
(I-11) 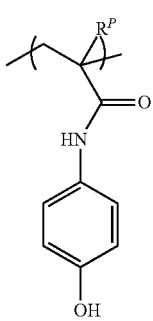
(I-12) 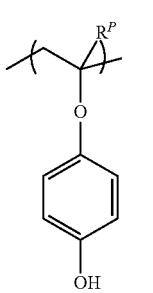
(I-13) 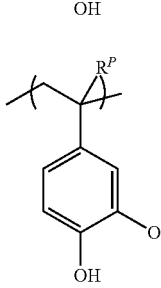
(I-14) 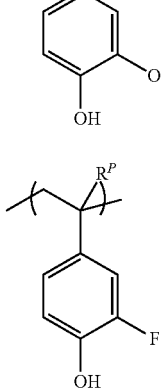
wherein
in each of the formulae (I-1) to (I-14), $R^P$ represents a hydrogen atom, a fluorine atom, a methyl group, or a trifluoromethyl group,
(1-1) 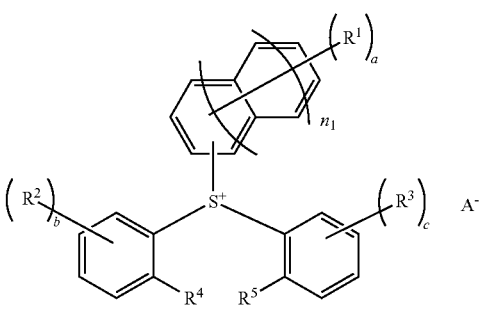

(1-2)

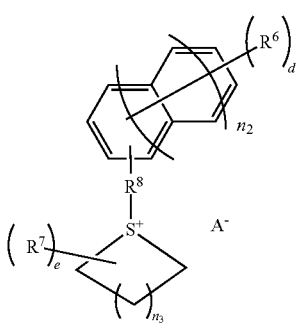

wherein in each of the formula (1-1) and the formula (1-2), A⁻ represents a monovalent sulfonic acid anion, in the formula (1-1), a is an integer of 0 to 11, b is an integer of 0 to 4, and c is an integer of 0 to 4, wherein a sum of a, b, and c is no less than 1; $R^1$, $R^2$, and $R^3$ each independently represent a hydroxy group, a nitro group, a halogen atom, or a monovalent organic group having 1 to 20 carbon atoms, wherein at least one of $R^e$, $R^2$, and $R^3$ represents a fluorine atom or a monovalent fluorinated hydrocarbon group having 1 to 10 carbon atoms, in a case in which a is no less than 2, a plurality of $R^1$s are identical or different, in a case in which b is no less than 2, a plurality of $R^2$s are identical or different, and in a case in which c is no less than 2, a plurality of $R^3$s are identical or different; $n_1$ is 0 or 1; and $R^4$ and $R^5$ each independently represent a hydrogen atom, a fluorine atom, or a monovalent fluorinated hydrocarbon group having 1 to 10 carbon atoms, or $R^4$ and $R^5$ taken together represent a single bond, in the formula (1-2), d is an integer of 1 to 11 and e is an integer of 0 to 10, wherein in a case in which d is 1, $R^6$ represents a fluorine atom or a monovalent fluorinated hydrocarbon group having 1 to 10 carbon atoms, and in a case in which d is no less than 2, a plurality of $R^6$s are identical or different, and each $R^6$ represents a hydroxy group, a nitro group, a halogen atom, or a monovalent organic group having 1 to 20 carbon atoms, wherein at least one of the plurality of $R^6$s represents a fluorine atom or a monovalent fluorinated hydrocarbon group having 1 to 10 carbon atoms; $R^7$ represents a hydroxy group, a nitro group, a halogen atom, or a monovalent organic group having 1 to 20 carbon atoms, wherein in a case in which e is no less than 2, a plurality of $R^7$s are identical or different; $R^8$ represents a single bond or a divalent organic group having 1 to 20 carbon atoms; nz is 0 or 1;

and $n_3$ is an integer of 0 to 3, and $$R^9—COO^-X^+ \quad (2)$$

in the formula (2), $R^9$ represents a monovalent organic group having 1 to 30 carbon atoms; and $X^+$ represents a monovalent radiation-sensitive onium cation, and wherein a molar amount of the first structural unit relative to a total molar amount of structural units constituting the polymer is 25 mol % or more, and a molar amount of the second structural unit relative to the total molar amount of the structural units constituting the polymer is 30 mol % or more.

16. The resist pattern-forming method according to claim 15, wherein the monovalent sulfonic acid anion comprises a partial structure represented by formula (3),

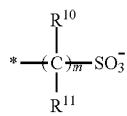

wherein in the formula (3), $R^{10}$ and $R^{11}$ each independently represent a hydrogen atom, a fluorine atom, a monovalent hydrocarbon group having 1 to 20 carbon atoms, or a monovalent fluorinated hydrocarbon group having 1 to 20 carbon atoms, wherein at least one of $R^{10}$ and $R^{11}$ represents a fluorine atom or a monovalent fluorinated hydrocarbon group having 1 to 20 carbon atoms; m is an integer of 1 to 10, wherein in a case in which m is no less than 2, a plurality of $R^{10}$s are identical or different and a plurality of $R^{11}$s are identical or different; and * denotes a binding site to a part other than the partial structure represented by the formula (3) in the monovalent sulfonic acid anion.

17. The resist pattern-forming method according to claim 16, wherein in the formula (3), $R^{10}$ and $R^{11}$ each independently represent a fluorine atom, a monovalent hydrocarbon group having 1 to 20 carbon atoms, or a monovalent fluorinated hydrocarbon group having 1 to 20 carbon atoms, wherein at least one of $R^{10}$ and $R^{11}$ represents a fluorine atom or a monovalent fluorinated hydrocarbon group having 1 to 20 carbon atoms; m is an integer of 2 to 10, wherein a plurality of $R^{10}$s are identical or different and a plurality of $R^{11}$s are identical or different.

18. The resist pattern-forming method according to claim 15, wherein the first compound is represented by the formula (1-1), and in the formula (1-1), the sum of a, b, and c is an integer of 2 to 6.

* * * * *

UNITED STATES PATENT AND TRADEMARK OFFICE
CERTIFICATE OF CORRECTION

| | | |
|---|---|---|
| PATENT NO. | : 11,609,495 B2 | Page 1 of 1 |
| APPLICATION NO. | : 17/081000 | |
| DATED | : March 21, 2023 | |
| INVENTOR(S) | : Katsuaki Nishikori et al. | |

It is certified that error appears in the above-identified patent and that said Letters Patent is hereby corrected as shown below:

In the Claims

In Line 1 of Column 98 in Claim 15:
"nz"
Should read:
--$n_2$--

Signed and Sealed this
Twenty-third Day of May, 2023

*Katherine Kelly Vidal*

Katherine Kelly Vidal
*Director of the United States Patent and Trademark Office*